(12) United States Patent
Rogers et al.

(10) Patent No.: US 9,875,974 B2
(45) Date of Patent: Jan. 23, 2018

(54) PROCESSING TECHNIQUES FOR SILICON-BASED TRANSIENT DEVICES

(71) Applicant: THE BOARD OF TRUSTEES OF THE UNIVERSITY OF ILLINOIS, Urbana, IL (US)

(72) Inventors: John A. Rogers, Champaign, IL (US); SukWon Hwang, Urbana, IL (US); Xian Huang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/772,354

(22) PCT Filed: Mar. 6, 2014

(86) PCT No.: PCT/US2014/021371
§ 371 (c)(1),
(2) Date: Sep. 2, 2015

(87) PCT Pub. No.: WO2014/138465
PCT Pub. Date: Sep. 12, 2014

(65) Prior Publication Data
US 2016/0005700 A1    Jan. 7, 2016

Related U.S. Application Data

(60) Provisional application No. 61/775,325, filed on Mar. 8, 2013, provisional application No. 61/828,758, filed on May 30, 2013.

(51) Int. Cl.
*H01L 21/00* (2006.01)
*H01L 23/00* (2006.01)
(Continued)

(52) U.S. Cl.
CPC ............ *H01L 23/564* (2013.01); *H01L 21/28* (2013.01); *H01L 21/30604* (2013.01);
(Continued)

(58) Field of Classification Search
CPC ............... H01L 23/53257; H01L 24/96; H01L 25/0655; H01L 25/16; H01L 25/50;
(Continued)

(56) References Cited

U.S. PATENT DOCUMENTS

| 7,195,733 B2 | 3/2007 | Rogers et al. |
| 7,521,292 B2 | 4/2009 | Rogers et al. |

(Continued)

FOREIGN PATENT DOCUMENTS

| WO | WO 2008/085904 | 7/2008 |
| WO | WO 2008/108838 | 9/2008 |

OTHER PUBLICATIONS

Ahn et al. (2006) "Heterogeneous three-dimensional electronics by use of printed semiconductor nanomaterials," Science. 314:1754-1757.
(Continued)

*Primary Examiner* — Richard Booth
(74) *Attorney, Agent, or Firm* — Lathrop Gage LLP

(57) ABSTRACT

Provided are methods of making a transient electronic device by fabricating one or more inorganic semiconductor components, one or more metallic conductor components or one or more inorganic semiconductor components and one or more metallic conductor components supported by a mother substrate. The components may independently comprise a selectively transformable material and, optionally, further have a preselected transience profile. The components are transfer printed, thereby decoupling the component fabrication step from additional processing to provide desired device functionality and transient properties. A sub- (Continued)

strate layer is provided on top of the components and used to facilitate handling, processing, and/or device functionality.

58 Claims, 35 Drawing Sheets

(51) Int. Cl.
| | |
|---|---|
| H01L 21/8238 | (2006.01) |
| H01L 21/28 | (2006.01) |
| H01L 21/306 | (2006.01) |
| H01L 21/56 | (2006.01) |
| H01L 21/683 | (2006.01) |
| H01L 21/768 | (2006.01) |
| H01L 21/78 | (2006.01) |
| H01L 21/84 | (2006.01) |
| H01L 23/532 | (2006.01) |
| H01L 25/065 | (2006.01) |
| H01L 25/16 | (2006.01) |
| H01L 25/00 | (2006.01) |
| G01N 27/22 | (2006.01) |

(52) U.S. Cl.
CPC ........ *H01L 21/561* (2013.01); *H01L 21/6835* (2013.01); *H01L 21/768* (2013.01); *H01L 21/78* (2013.01); *H01L 21/8238* (2013.01); *H01L 21/84* (2013.01); *H01L 23/53257* (2013.01); *H01L 24/96* (2013.01); *H01L 25/0655* (2013.01); *H01L 25/16* (2013.01); *H01L 25/50* (2013.01); *G01N 27/22* (2013.01); *H01L 2221/68368* (2013.01); *H01L 2221/68372* (2013.01); *H01L 2221/68381* (2013.01); *H01L 2924/0103* (2013.01); *H01L 2924/01012* (2013.01); *H01L 2924/01026* (2013.01); *H01L 2924/01042* (2013.01); *H01L 2924/01074* (2013.01); *H01L 2924/1203* (2013.01); *H01L 2924/1205* (2013.01); *H01L 2924/12043* (2013.01); *H01L 2924/13091* (2013.01)

(58) Field of Classification Search
CPC ... H01L 23/564; H01L 21/8238; H01L 21/28; H01L 21/30604; H01L 21/561; H01L 21/6835; H01L 21/768; H01L 21/78; H01L 21/84
See application file for complete search history.

(56) References Cited

U.S. PATENT DOCUMENTS

| | | | |
|---|---|---|---|
| 7,557,367 B2 | 7/2009 | Rogers et al. | |
| 7,604,663 B1 | 10/2009 | Reimink | |
| 7,622,367 B1 | 11/2009 | Nuzzo et al. | |
| 7,704,684 B2 | 4/2010 | Rogers et al. | |
| 7,705,280 B2 | 4/2010 | Nuzzo et al. | |
| 7,799,699 B2 | 9/2010 | Nuzzo et al. | |
| 7,932,123 B2 | 4/2011 | Rogers et al. | |
| 7,943,491 B2 | 5/2011 | Nuzzo et al. | |
| 7,972,875 B2 | 7/2011 | Rogers et al. | |
| 7,982,296 B2 | 7/2011 | Nuzzo et al. | |
| 8,039,847 B2 | 10/2011 | Nuzzo et al. | |
| 8,198,621 B2 | 6/2012 | Rogers et al. | |
| 8,217,381 B2 | 7/2012 | Rogers et al. | |
| 8,327,532 B2 | 12/2012 | Xu et al. | |
| 8,367,035 B2 | 2/2013 | Rogers et al. | |
| 8,394,706 B2 | 3/2013 | Nuzzo et al. | |
| 8,440,546 B2 | 5/2013 | Nuzzo et al. | |
| 8,470,701 B2 | 6/2013 | Rogers et al. | |
| 8,552,299 B2 | 10/2013 | Rogers et al. | |
| 8,562,095 B2 | 10/2013 | Alleyene et al. | |
| 8,664,699 B2 | 3/2014 | Nuzzo et al. | |
| 8,666,471 B2 | 3/2014 | Rogers et al. | |
| 8,679,888 B2 | 3/2014 | Rogers et al. | |
| 8,722,458 B2 | 5/2014 | Rogers et al. | |
| 8,729,524 B2 | 5/2014 | Rogers et al. | |
| 8,754,396 B2 | 6/2014 | Rogers et al. | |
| 8,865,489 B2 | 10/2014 | Rogers et al. | |
| 8,895,406 B2 | 11/2014 | Rogers et al. | |
| 8,934,965 B2 | 1/2015 | Rogers et al. | |
| 8,946,683 B2 | 2/2015 | Rogers et al. | |
| 9,057,994 B2 | 6/2015 | Rogers et al. | |
| 9,061,494 B2 | 6/2015 | Rogers et al. | |
| 9,105,555 B2 | 8/2015 | Rogers et al. | |
| 9,105,782 B2 | 8/2015 | Rogers et al. | |
| 9,117,940 B2 | 8/2015 | Rogers et al. | |
| 2008/0055581 A1 | 3/2008 | Rogers et al. | |
| 2008/0090097 A1 | 4/2008 | Shaw et al. | |
| 2008/0306359 A1 | 12/2008 | Zdeblick et al. | |
| 2011/0230747 A1 | 9/2011 | Rogers et al. | |
| 2011/0316120 A1 | 12/2011 | Rogers et al. | |
| 2012/0157804 A1 | 6/2012 | Rogers et al. | |
| 2012/0165759 A1 | 6/2012 | Rogers et al. | |
| 2012/0223293 A1 | 9/2012 | Borenstein et al. | |
| 2012/0261551 A1 | 10/2012 | Rogers et al. | |
| 2012/0320581 A1 | 12/2012 | Rogers et al. | |
| 2013/0036928 A1 | 2/2013 | Rogers et al. | |
| 2013/0041235 A1 | 2/2013 | Rogers et al. | |
| 2013/0140649 A1 | 6/2013 | Rogers et al. | |
| 2013/0333094 A1 | 12/2013 | Rogers et al. | |
| 2014/0163390 A1 | 6/2014 | Rogers et al. | |
| 2014/0191236 A1 | 7/2014 | Nuzzo et al. | |
| 2014/0220422 A1 | 8/2014 | Rogers et al. | |
| 2014/0305900 A1 | 10/2014 | Rogers et al. | |
| 2014/0323968 A1 | 10/2014 | Rogers et al. | |
| 2014/0361409 A1 | 12/2014 | Rogers et al. | |
| 2014/0374872 A1 | 12/2014 | Rogers et al. | |
| 2015/0001462 A1 | 1/2015 | Rogers et al. | |
| 2015/0080695 A1 | 3/2015 | Rogers et al. | |
| 2015/0132873 A1 | 5/2015 | Rogers et al. | |
| 2015/0141767 A1 | 5/2015 | Rogers et al. | |
| 2015/0181700 A1 | 6/2015 | Rogers et al. | |
| 2015/0207012 A1 | 7/2015 | Rogers et al. | |
| 2015/0237711 A1 | 8/2015 | Rogers et al. | |
| 2015/0290938 A1 | 10/2015 | Rogers et al. | |
| 2015/0373831 A1 | 12/2015 | Rogers et al. | |
| 2015/0380355 A1 | 12/2015 | Rogers et al. | |
| 2016/0005700 A1 | 1/2016 | Rogers et al. | |
| 2016/0027737 A1 | 1/2016 | Rogers et al. | |

OTHER PUBLICATIONS

Ahn et al. (2006) "High-speed mechanically flexible single-crystal silicon thin-film transistors on plastic substrates," IEEE Elect. Dev. Lett. 27:460-462.
Ahn et al. (2007) "Bendable integrated circuits on plastic substrates by use of printed ribbons of single-crystalline silicon," Appl. Phys. Lett. 90:213501.
Ahn et al. (2009) "Omnidirectional Printing of Flexible, Stretchable, and Spanning Silver Microelectrodes," Science. 323:1590-1593.
Al-Hardan et al. (2010) "The effect of oxygen ratio on the crystallography and optical emission properties of reactive RF sputtered ZnO films," Physica B. 405:1081-1085.
Andosca et al. (May 2012) "Experimental and theoretical studies on MEMS piezoelectric vibrational energy harvesters with mass loading," Sensors and Actuators A. 178:76-87.
Angelopoulos et al. (Sep. 17-21, 2012) "Manufacturing aspects of an ultra-thin chip technology," In; The Proceedings of the European Solid-State Device Research Conference (ESSDERC) 2012. Bordeaux, France. Ed.: Yann Deval. pp. 141-144.
APC International, Ltd. (2011) Piezoelectric Ceramics: Principles and Applications. APC International. p. 16.
Arai et al. "Biodegradation of Bombyx mori silk fibroin fibers and films," J. Appl. Polym. 91:2383-2390.
Baca et al. (2007) "Printable Single-Crystal Silicon Micro/Nanoscale Ribbons, Platelets and Bars Generated from Bulk Wafers," Adv. Funct. Mater. 17:3051-3062.

(56) References Cited

OTHER PUBLICATIONS

Barbottin et al. (1989) "Instabilities in Field Effect Transistors," Ch. 15. In; Instabilities in Silicon Devices. vol. 2. Elsevier. Amsterdam, The Netherlands.
Baskoutas et al. (2011) "Transition in the Optical Emission Polarization of ZnO Nanorods," J. Phys. Chem. C. 115:15862-15867.
Bernardini et al. (1997) "Spontaneous polarization and piezoelectric constants of III-V nitrides," Physical Review B. 56:R10024.
Bettinger et al. (2010) "Biomaterials-based organic electronic devices," Polym Int. 59:563-567.
Bettinger et al. (2010) "Organic thin-film transistors fabricated on resorbable biomaterial substrates," Adv. Mater. 22:651-655.
Blom et al. (1990) "Thin-film ZnO as micromechanical actuator at low frequencies," Sensors and Actuators 21:226-228.
Bower et al. (2009) "Transfer-Printed Microscale Integrated Circuits," In; The Proc. $59^{th}$ Elec. Comp. Tech. Conf ($59^{th}$ ECTC). San Diego, California. p. 618.
Briscoe (Aug. 30, 2012) "Measured efficiency of a ZnO nanostructured diode piezoelectric energy harvesting device," App. Phys. Lett. 101:093902.
Buchanan (1999) "Scaling the gate dielectric: Materials, integration, and reliability," IBM J. Res. Develop. 43:245-264.
Burghartz et al. (2009) "A New Fabrication and Assembly Process for Ultrathin Chips," IEEE Trans. Electron Dev. 56:321-327.
Camacho et al. (2011) "Structural, optical and electrical properties of ZnO thin films grown by radio frequency (rf) sputtering in oxygen atmosphere," International Journal of the Physical Sciences. 6:6660-6663.
Carcia et al. (2006) "High-performance ZnO thin-film transistors on gate dielectrics grown by atomic layer deposition," Appl. Phys. Lett. 88:123509.
Carlson et al. (Aug. 31, 2012) "Transfer Printing Techniques for Materials Assembly and Micro/Nanodevice Fabrication," Adv. Mater. 24:5284-5318.
Cavusoglu et al. (2005) "Resorbable plate-screw systems: Clinical applications," Ulus. Travma Acil Cerrahi Derg. 11:43-48.
Chang et al. (2010) "Direct-write piezoelectric polymeric nanogenerator with high energy conversion efficiency," Nano Lett. 10:726-731.
Chen et al. (2003) "Electronic paper: Flexible active-matrix electronic ink display," Nature. 423:136.
Chen et al. (2005) "Humidity Sensors: A Review of Materials and Mechanisms," Sensor Letters. 3:274-295.
Chern et al. (1980) "A new method to determine MOSFET channel length," IEEE Electron. Dev. Lett. 1:170-173.
Chiu et al. (1995) "Effects of polymer degradation on drug released—mechanistic study of morphology and transport properties in 50:50 poly(dl-lactide-co-glycolide)," Int. J. Pharm. 126:169-178.
Choi et al. (2003) "Investigation of Gate-Induced Drain Leakage (GIDL) Current in Thin Body Devices: Single-Gate Ultra-Thin Body, Symmetrical Double-Gate, and Asymmetrical Double-Gate MOSFETs," Jpn. J. Appl. Phys. 42:2073-2076.
Choi et al. (2009) "The effects of rapid thermal annealing on the performance of ZnO thin-film transistors," Journal of the Korean Physical Society. 55:1925-1930.
Choi-Yim et al. (1998) "The effect of silicon on the glass forming ability of the Cu47Ti34Zr11Ni8 bulk metallic glass forming alloy during processing of composites," J. Appl. Phys. 83:7993.
Chung et al. (2011) "Fabrication of Releasable Single-Crystal Silicon-Metal Oxide Field-Effect Devices and Their Deterministic Assembly on Foreign Substrates," Adv. Func. Mater. 21:3029-3036.
Csutak et al. (2002) "CMOS-compatible high-speed planar silicon photodiodes fabricated on SOI substrates," IEEE Journal of Quantum Electronics. 38:193-196.
Czekalla et al. (2008) "Spatial fluctuations of optical emission from single ZnO/MgZnO nanowire quantum wells," Nanotechnology. 19:115202.

Dagdeviren et al. (Apr. 19, 2013) "Transient, Biocompatible Electronics and Energy Harvesters Based on ZnO," Small. 9(20):3398-3404.
Danckwerts (1950) "Absorption by simultaneous diffusion and chemical reaction," Transactions of the Faraday Society. 46:300-304.
David et al. (Apr. 26, 2012) "Dissolution Kinetics and Solubility of ZnO Nanoparticles Followed by AGNES," J. Phys. Chem. 116:11758-11767.
Ducéré et al. (2005) "A capacitive humidity sensor using cross-linked cellulose acetate butyrate," Sensors and Actuators B: Chemical. 106:331-334.
Farra et al. (2012) "First-in-Human Testing of a Wirelessly Controlled Drug Delivery Microchip," Sci. Trans. Med. 4(122). pp. 1-10.
Fink et al. (2002) "Enhancement of device performance in vertical sub-100 nm MOS devices due to local channel doping," Solid State Electron. 46:387-391.
Fukushima et al. (2010) "Surface tension-driven chip self-assembly with load-free hydrogen fluoride-assisted direct bonding at room temperature for three-dimensional integrated circuits," Appl. Phys. Lett. 96:154105.
Fulati et al. (2009) "Miniaturized pH Sensors Based on Zinc Oxide Nanotubes/Nanorods," Sensors. 9:8911-8923.
Gabriel et al. (2006) "The dielectric properties of biological tissues: I. Literature survey," Phys. Med. Biol. 41:2231-2249.
Gabriel et al. (2009) "Electrical conductivity of tissue at frequencies below 1 MHz," Phys. Med. Biol. 54:4863-4878.
Gerischer et al. (1992) "Chemical dissolution of zinc oxide crystals in aqueous electrolytes—An analysis of the kinetics," Electrochimica Acta. 37:827-835.
Gracias et al. (2000) "Forming Electrical Networks in Three Dimensions by Self-Assembly," Science. 289:1170-1172.
Grosjean et al. (2006) "Hydrolysis of Mg-salt and MgH2-salt mixtures prepared by ball milling for hydrogen production," Journal of Alloys and Compounds. 416:296-302.
Gullapalli et al. (2010) "Flexible Piezoelectric ZnO-Paper Nanocomposite Strain Sensor," Small. 6:1641-1646.
Gupta et al. (2010) "Development of gas sensors using ZnO nanostructures," J. Chem. Sci. 122:57-62.
Hamer et al. (2009) "AMOLED Displays Using Transfer-Printed Integrated Circuits," SID 2009 International Symposium Digest of Technical Papers. 15:947-950.
Hoffman et al. (2003) "ZnO-based transparent thin-film transistors," Appl. Phys. Lett. 82:733.
Horan et al. (2005) "In vitro degradation of silk fibroin," Biomaterials. 26:3385-3393.
Huang et al. (2011) "A flexible pH sensor based on the iridium oxide sensing film," Sensors and Actuators A: Physical. 169:1-11.
Huang et al. (Aug. 23, 2012) "Epidermal differential impedance sensor for conformal skin hydration monitoring," Biointerphases. 7:52.
Hudson et al. (2008) "The biocompatibility of mesoporous silicates," Biomaterials. 29:4045-4055.
Hutmacher (2001) "Scaffold design and fabrication technologies for engineering tissues—state of the art and future perspectives," J. Biomater. Sci. Polymer Edn. 12:107-124.
Hwang et al. (Apr. 2012) "A Physically Transient Form of Silicon Electronics," Science 337:1640-1644.
Hwang et al. (Apr. 11, 2013) "Materials and Fabrication Processes for Transient and Bioresorbable High-Performance Electronics," Adv. Funct. Mater. 23(33):4087-4093.
Hwang et al. (May 17, 2013) "Materials for bioresorbable radio frequency electronics," Adv. Mater. 25:3526-3531.
Ilican et al. (2008) "Preparation and characterization of ZnO thin films deposited by sol-gel spin coating method ," Journal of Optoelectronics and Advance Materials. 10:2578-2583.
Im et al. (2007) "Evolution in LTPS AMLCD Manufacturing via Advances in Laser Crystallization Techniques and Systems," Information Display. vol. 23. No. 09.
International Search Report with Written Opinion corresponding to International Patent Application No. PCT/US2014/021371, dated Jun. 25, 2014.

(56) References Cited

OTHER PUBLICATIONS

Irimia-Vladu (2010) "Environmentally sustainable organic field effect transistors," Organic Electronics. 11:1974-1990.
Irimia-Vladu et al. (2010) "Biocompatible and Biodegradable Materials for Organic Field-Effect Transistors," Adv. Funct. Mater. 20:4069-4076.
Jeon et al. (2007) "Low-Voltage Zinc-Oxide Thin-Film Transistors on a Conventional SiO2 Gate Insulator Grown by Radio-Frequency Magnetron Sputtering at Room Temperature," Journal of the Korean Physical Society. 51:1999-2003.
Jeong et al. (2007) "Flexible Full-Color AMOLED on Ultrathin Metal Foil," IEEE Elect. Dev. Lett. 28:389-391.
Kamath et al. (1993) "Biodegradable hydrogels in drug delivery," Adv. Drug Delivery Rev. 11:59-84.
Kanicki et al. (2003) "Hydrogenated Amorphous Silicon Thin-Film Transistors," Ch. 3 In; Thin Film Transistors. Eds.: Kagan, C. R.; Andry, P. Marcel-Dekker. New York, New York. pp. 71-137.
Kerber et al. (2009) "Reliability Challenges for CMOS Technology Qualifications With Hafnium Oxide/Titanium Nitride Gate Stacks," IEEE Trans. Device Mater. Reliab. 9:147-162.
Kim et al. (2008) "Complementary Logic Gates and Ring Oscillators on Plastic Substrates by Use of Printed Ribbons of Single-Crystalline Silicon," IEEE Elect. Dev. Lett. 29:73-76.
Kim et al. (2008) "Stretchable and Foldable Silicon Integrated Circuits," Science. 320:507-511.
Kim et al. (2009) "Electrically interconnected assemblies of microscale device components by printing and molding," Appl. Phys. Lett. 95:214101.
Kim et al. (2009) "Emerging Technologies for the Commercialization of AMOLED TVs," Information Display. vol. 25. No. 09.
Kim et al. (2009) "Self-assembled nanodielectrics and silicon nanomembranes for low voltage, flexible transistors, and logic gates on plastic substrates," Appl. Phys. Lett. 95:183504.
Kim et al. (2009) "Silicon electronics on silk as a path to bioresorbable, implantable devices," Appl. Phys. Lett. 95:133701.
Kim et al. (2010) "Dissolvable films of silk fibroin for ultrathin conformal bio-integrated electronics," Nat. Mater. 9:511-517.
Kim et al. (May 7, 2013) "Deterministic assembly of releasable single crystal silicon-metal oxide field-effect devices formed from bulk wafers," 102:182104.
Knuesel et al. (2010) "Self-assembly of microscopic chiplets at a liquid-liquid-solid interface forming a flexible segmented monocrystalline solar cell," Proc. Natl. Acad. Sci. USA. 107:993-998.
Ko et al. (2006) "Bulk Quantities of Single-Crystal Silicon Micro-/Nanoribbons Generated from Bulk Wafers," Nano Lett. 6:2318-2324.
Ko et al. (2010) "Ultrathin compound semiconductor on insulator layers for high-performance nanoscale transistors," Nature. 468:286-289.
Kozicki et al. (2005) "Programmable metallization cell memory based on Ag—Ge—S and Cu—Ge—S solid electrolytes," Non-Volatile Memory Technology Symposium 2005. pp. 83-89.
Krejčiřík et al. (2007) "Non-Hermitian spectral effects in a PT-symmetric waveguide," Nanotechnology. 18:475-504.
Kringelbach et al. (2007) "Translational principles of deep brain stimulation," Nat. Rev. Neurosci. 8(8):623-635.
Kumar et al. (2006) "Ultrasensitive DNA sequence detection using nanoscale ZnO sensor arrays," Nanotechnology. 17:2875-2881.
Kumar et al. (2011) "ZnO nanoparticle as catalyst for efficient green one-pot synthesis of coumarins through Knoevenagel condensation," J. Chem. Sci. 123:615-621.
Kuo (2004) "Deposition of Dielectric Thin Films for a-Si:H TFT," Ch. 6 In; Thin Film Transistors Materials and Processe. vol. 1. Klewer Academic. Norwell, Massachusetts.
Kurzweil (2009) "Metal Oxides and Ion-Exchanging Surfaces as pH Sensors in Liquids: State-of-the-Art and Outlook," Sensors (Basel). 9:4955-4985.
Lam et al. (2008) "Dynamics of in vitro polymer degradation of polycaprolactone-based scaffolds: accelerated versus simulated physiological conditions," Biomed. Mater. 3:034108.
Laurencin et al. (1999) "Tissue engineering: orthopedic applications," Annu. Rev. Biomed. Eng. 1:19-46.
Lee et al. (2005) "Dielectrophoresis and Chemically Mediated Directed Self-Assembly of Micrometer-Scale Three-Terminal Metal Oxide Semiconductor Field-Effect Transistors," Adv. Mater. 17:2671-2677.
Lee et al. (2010) "Fabrication of microstructured silicon (μs-Si) from a bulk Si wafer and its use in the printing of high-performance thin-film transistors on plastic substrates," J. Micromech. Microeng. 20:075018.
Lee et al. (2010) "Mechanically flexible thin film transistors and logic gates on plastic substrates by use of single-crystal silicon wires from bulk wafers," Appl. Phys. Lett. 96:173501.
Legnani et al. (2008) "Bacterial cellulose membrane as flexible substrate for organic light emitting devices," Thin Solid Films. 517:1016-1020.
Lendlein et al. (2002) "Biodegradable, Elastic Shape-Memory Polymers for Potential Biomedical Applications," Science. 296:1673-1676.
Li et al. (2008) "Cellular Level Biocompatibility and Biosafety of ZnO Nanowires," J. Phys. Chem. C. 112:20114-20117.
Li et al. (Jan. 21, 2013) "An Analytical Model of Reactive Diffusion for Transient Electronics," Advanced Functional Materials. 23:3106-3114.
Luan et al. (1992) "An experimental study of the source/drain parasitic resistance effects in amorphous silicon thin film transistors," J. Appl. Phys. 72:766.
Mack et al. (2006) "Mechanically Flexible Thin-Film Transistors that use Ultrathin Ribbons of Silicon Derived from Bulk Wafers," Appl. Phys. Lett. 88:213101.
Makadia et al. (2011) "Poly Lactic-co-Glycolic Acid (PLGA) as Biodegradable Controlled Drug Delivery Carrier," Polymers. 3:1377-1397.
Mannsfeld et al. (2010) "Highly sensitive flexible pressure sensors with microstructured rubber dielectric layers," Nat. Mater. 9:859-864.
Martinez-Boubeta et al. (2010) "Self-assembled multifunctional Fe/MgO nanospheres for magnetic resonance imaging and hyperthermia," Nanomedicine: Nanotechnology, Biology, and Medicine. 6:362-370.
Mastrangeli et al. (2009) "Self-assembly from milli- to nanoscales: methods and applications," J. Micromech. Microeng. 19:083001.
Masuda et al. (2003) "Transparent thin film transistors using ZnO as an active channel layer and their electrical properties," J. Appl. Phys. 93:1624.
Meitl et al. (2006) "Transfer printing by kinetic control of adhesion to an elastomeric stamp," Nat. Mater. 5:33-38.
Menard et al. (2005) "Bendable single crystal silicon thin film transistors formed by printing on plastic substrates," Appl. Phys. Lett. 86:093507.
Miyamoto et al. (2004) "High-electron-mobility ZnO epilayers grown by plasma-assisted molecular beam epitaxy," Journal of Crystal Growth. 265:34-40.
Momose et al. (2002) "Ultrathin gate oxide CMOS on (111) surface-oriented Si substrate," IEEE Trans. Electron. Dev. 49:1597-1605.
Mondal et al. (2008) "Preparation of Al-Doped ZnO (AZO) Thin Film by SILAR," Journal of Physical Sciences. 12:221-229.
Moore et al. (1959) "II. Diffusion of zinc and oxygen in zinc oxide," Discussions of the Faraday Society. 28:86-93.
Moravej et al. (2011) "Biodegradable Metals for Cardiovascular Stent Application: Interests and New Opportunities," Int. J. Mol. Sci. 12:4250-4270.
Mudunkotuwa et al. (Nov. 28, 2011) "Dissolution of ZnO Nanoparticles at Circumneutral pH: A Study of Size Effects in the Presence and Absence of Citric Acid," Langmuir. 28:396-403.
Ondo-Ndong et al. (2003) "Electrical properties of zinc oxide sputtered thin films," Microelectronics Journal. 34:1087-1092.

(56) References Cited

OTHER PUBLICATIONS

Pang et al. (Jul. 29, 2012) "A flexible and highly sensitive strain-gauge sensor using reversible interlocking of nanofibres," Nat. Mater. 11:795-801.
Panilaitis et al. (2003) "Macrophage responses to silk," Biomaterials. 24:3079-3085.
Park et al. (2007) "High-resolution electrohydrodynamic jet printing," Nat. Mater. 6:782-789.
Park et al. (2008) "Theoretical and Experimental Studies of Bending of Inorganic Electronic Materials on Plastic Substrates," Adv. Funct. Mater. 18:2673-2684.
Park et al. (2010) "Nanoscale, Electrified Liquid Jets for High-Resolution Printing of Charge," Nano Lett. 10:584-591.
Peuster et al. (2001) "A novel approach to temporary stenting: degradable cardiovascular stents produced from corrodible metal—results 6-18 months after implantation into New Zealand white rabbits," Heart. 86:563-569.
Pierret (1996) "Non Ideal MOS," Ch. 18 In; Semiconductor Device Fundamentals. Addison-Wesley. Natick, Massachusetts. pp. 645-690.
Pierret (1996) "MOSFETs—The Essentials," Ch. 17 In; Semiconductor Device Fundamentals. Addison-Wesley. Natick, Massachusetts. pp. 611-645.
Pique et al. (2006) "Embedding electronic circuits by laser direct-write," Microelect. Eng. 83:2527-2533.
Ponnusamy et al. (Apr. 1, 2012) "In vitro degradation and release characteristics of spin coated thin films of PLGA with a 'breath figure' morphology" Biomatter. 2:77-86.
Raicu et al. (2000) "A quantitative approach to the dielectric properties of the skin," Phys. Med. Biol. 45:L1.
Reed et al. (Dec. 9, 2011) "Solubility of nano-zinc oxide in environmentally and biologically important matrices," Environ. Toxicol. Chem. 31:93-99.
Reiner et al. (2010) "Crystalline Oxides on Silicon," Adv. Mater. 22:2919-2938.
Reuss et al. (2006) "Macroelectronics," MRS Bulletin. 31:447-454.
Richter et al. (2008) "Review on Hydrogel-based pH Sensors and Microsensors," Sensors. 8:561-581.
Robertson (2004) "High dielectric constant oxides," Eur. Phys. J. Appl. Phys. 28:265-291.
Robertson (2006) "High dielectric constant gate oxides for metal oxide Si transistor," Rep. Prog. Phys. 69:327-396.
Robertson (2008) "Maximizing performance for higher K gate dielectrics," J. Appl. Phys. 104:124111.
Rogers et al. (2011) "Synthesis, assembly and applications of semiconductor nanomembranes," Nature. 477:45-53.
Saad et al. (2008) "Characterization of various zinc oxide catalysts and their activity in the dehydration-dehyrogenation of isobutanol," J. Serb. Chem. Soc. 73:997-1009.
Sabir et al. (2009) "A review on biodegradable polymeric materials for bone tissue," J. Mater. Sci. 44:5713-5724.
Sato et al. (1999) "Anisotropic etching rates of single-crystal silicon for TMAH water solution as a function of crystallographic orientation," Sens. Actuators A. 73:131-137.
Schlom et al. (2008) "Gate Oxides Beyond $SiO_2$," MRS Bulletin. 33:1017-1025.
Schoenfeld (2007) "Contemporary Pacemakers and Defibrillator Device Therapy," Circulation.115:638-653.
Schroder (2006) "Mobility," Ch. 8 In; Semiconductor Materials and Device Characterization. $3^{rd}$ Ed. Wiley. Hoboken, New Jersey.
Seidel et al. (1990) "Anisotropic Etching of Crystalline Silicon in Alkaline Solutions II. Influence of Dopants," J. Electrochem. Soc. 737:3626-3632.
Sekitani et al. (2008) "Organic transistors manufactured using inkjet technology with subfemtoliter accuracy," Proc. Nat. Acad. Sci. 105:4976-4980.
Sekitani et al. (Mar. 2012) "Stretchable organic integrated circuits for large-area electronic skin surface," MRS Bull. 37:236-245.
Semprius.com (2014) "Semprius," Semprius, Inc. Accessible on the Internet at URL: http://www.semprius.com/. [Last Accessed Dec. 9, 2015].
Shahrjerdi et al. (Dec. 18, 2012) "Extremely Flexible Nanoscale Ultrathin Body Silicon Integrated Circuits on Plastic," Nano Lett. 13:315-320.
Shen et al. (2007) "Submicron particles of SBA-15 modified with MgO as carriers for controlled drug delivery," Chem. Pharm. Bull. 55:985-991.
Shimizu et al. (Jun. 2012) "Zinc Oxide Paste as Sunscreen in the Postoperative Period," Dermatologic Surgery. 38:965-966.
Singhal et al. (1998) "Absorbable Suture Materials: Preparation and Properties," Polym. Rev. 28:475-502.
Solorio et al. (Nov. 8, 2012) "Noninvasive characterization of the effect of varying PLGA molecular weight blends on in situ forming implant behavior using ultrasound imaging," 2(11):1064-1077.
Song et al. (2003) "Understanding Magnesium Corrosion—A Framework for Improved Alloy Performance," Advanced Engineering Materials. 5:837-858.
Song et al. (2009) "Mechanics of noncoplanar mesh design for stretchable electronic circuits," Journal of Applied Physics. 105:123516.
Soppimatha et al. (2001) "Biodegradable polymeric nanoparticles as drug delivery devices," J. Controlled Release. 70(1-2):1-20.
Staiger et al. (2006) "Magnesium and its alloys as orthopedic biomaterials: a review," Biomaterials. 27:1728-1734.
Stathis et al. (2006) "The negative bias temperature instability in MOS devices: A review," Microelec. Rel. 46:270-286.
Stauth et al. (2006) "Self-assembled single-crystal silicon circuits on plastic," Proc. Natl. Acad. Sci. USA. 19:13922-13927.
Su et al. (Dec. 1, 2011) "Postbuckling analysis and its application to stretchable electronics," Journal of the Mechanics and Physics of Solids. 60:487-508.
Sun et al. (1980) "Electron Mobility in Inversion and Accumulation Layers on Thermally Oxidized Silicon Surfaces," IEEE J. Solid-State Circuits 5:562-573.
Sunaga et al. (2002) "Measurement of the electrical properties of human skin and the variation among subjects with certain skin conditions," Phys. Med. Biol. 47:N11-N15.
Tabata et al. (1992) "Anisotropic etching of silicon in TMAH solutions," Sens. Actuators, A. 34:51-57.
Takagi et al. (1994) "On the universality of inversion layer mobility in Si MOSFET's: Part II—effects of surface orientation," IEEE Trans. Electron Dev. 41:2363-2368.
Takei et al. (2010) "Nanowire active-matrix circuitry for low-voltage macroscale artificial skin," Nat. Mater. 9:821-826.
Trewyn et al. (2008) "Biocompatible mesoporous silica nanoparticles with different morphologies for animal cell membrane penetration," Chemical Engineering Journal. 137:23-29.
Valtiner et al. (2008) "Stabilization and Acidic Dissolution Mechanism of Single-Crystalline ZnO(0001) Surfaces in Electrolytes Studied by In-Situ AFM Imaging and Ex-Situ LEED," Langmuir. 24:5350-5358.
Van der Wilt et al. (2006) "Low-Temperature Polycrystalline Silicon Thin-Film Transistors and Circuits on Flexible Substrates," MRS Bulletin. 31:461-465.
Wales et al. (2003) "Stationary points and dynamics in high-dimensional systems," J. Chem. Phys. 119:12409-12416.
Wang et al. (1999) "Electromechanical coupling and output efficiency of piezoelectric bending actuators," IEEE Transactions on Ultrasonics, Ferroelectrics and Frequency Control. 46:638-646.
Wegner et al. (2006) "In situ formation and hydrolysis of Zn nanoparticles for H2 production by the 2-step ZnO/Zn water-splitting thermochemical cycle," International Journal of Hydrogen Energy. 31:55-61.
Williams et al. (2003) "Etch rates for micromachining processing—Part II," J. Microelectromech. Sys. 12:761-778.
Woodruff et al. (2010) "The return of a forgotten polymer—Polycaprolactone in the 21st century," Prog. Polym. Sci. 35:1217-1256.

(56) References Cited

OTHER PUBLICATIONS

Wu et al. (2001) "Synthesis, characterization, biodegradation, and drug delivery application of biodegradable lactic/glycolic acid polymers. Part II: Biodegradation," J. Biomater. Sci. Polymer Edn. 12:21-34.
Yuan et al. (2006) "High-speed strained-single-crystal-silicon thin-film transistors on flexible polymers," J. Appl. Phys. 2006, 100, 013708.
Zaumseil et al. (2003) "Contact resistance in organic transistors that use source and drain electrodes formed by soft contact lamination," J. Appl. Phys. 93:6117-6124.
Zhai et al. (Oct. 23, 2012) "High-Performance Flexible Thin-Film Transistors Exfoliated from Bulk Wafer," Nano Lett. 12:5609-5615.
Zhang et al. (2010)"Fabrication and comparative study of top-gate and bottom-gate ZnO-TFTs with various insulator layers," J. Mater. Sci.: Mater. Electron. 21:671-675.
Zhao et al. (2004) "Piezoelectric Characterization of Individual Zinc Oxide Nanobelt Probed by Piezoresponse Force Microscope," Nano Lett. 4:587-590.
Zheng et al. (2009) "In Vitro and In Vivo Biocompatibility Studies of ZnO Nanoparticles," International Journal of Modern Physics B. 23:1566-1571.
Zhou et al. (2006) "Dissolving Behavior and Stability of ZnO Wires in Biofluids: A Study on Biodegradability and Biocompatibility of ZnO Nanostructures," Adv. Mater. 18:2432-2435.
Zhou et al. (Feb. 18, 2013) "Fast flexible electronics with strained silicon nanomembranes," Scientific Reports. 3:1291.
Zhu et al. (2010) "Flexible High-Output Nanogenerator Based on Lateral ZnO Nanowire Array," Nano Lett. 10:3151-3155.
Notice of Allowance for U.S. Appl. No. 14/250,671, a related application, dated Jul. 13, 2016, 14 pp.

PROCESSING TECHNIQUES FOR SILICON-BASED TRANSIENT DEVICES

CROSS-REFERENCE TO RELATED APPLICATIONS

This application is a U.S. National Stage Application under 35 U.S.C. §371 of International Application No. PCT/US2014/021371, filed Mar. 6, 2014, which claims the benefit of priority from U.S. Provisional Patent Application No. 61/828,758, filed May 30, 2013, and U.S. Provisional Patent Application No. 61/775,325 filed Mar. 8, 2013, which are each hereby incorporated by reference to the extent not inconsistent with the disclosure of this application.

STATEMENT REGARDING FEDERALLY SPONSORED RESEARCH OR DEVELOPMENT

This invention was made, at least in part, with U.S. governmental support under 1242240 by the National Science Foundation and W911NF-11-1-0254 by the Defense Advanced Research Projects Agency. The U.S. Government has certain rights in this invention.

BACKGROUND OF INVENTION

This invention is in the field of transient devices, and relates generally to passive and active devices designed to programmably transform.

Transient devices have potential for a range of important applications. For example, eco-degradable environmental sensors avoid the need for device collection and bioresorbable medical devices that degrade and are cleared from the body minimize or avoid toxicity and inflammation. Strategically, commercial or military devices that degrade after a preselected time or upon application of a triggered stimulus avoid transferring knowledge or materials to competitors or enemies. All of these envisioned applications are important, but implementation of transient devices is dependent upon design strategies. Design and processing strategies for transient devices must: (i) support device fabrication using degradable device component materials and degradable substrates, (ii) provide for accurate control of the useful lifetime of the device, and (iii) utilize materials that are compatible with and perform adequately for a given application within a target environment.

Recently, a number of patents and publications have disclosed devices with transient properties. For example, Kim et al., "Silicon electronics on silk as a path to bioresorbable implantable devices", Appl. Phys. Lett. 95, 133701 (2009); U.S. Patent Application Publication 2011/0230747; and International Patent Application Publication WO 2008/085904 disclose biodegradable electronic devices that may include a biodegradable semiconducting material and a biodegradable substrate. Bettinger et al., "Organic thin film transistors fabricated on resorbable biomaterial substrates", Adv. Mater., 22(5), 651-655 (2010); Bettinger et al., "Biomaterial-based organic electronic devices", Poly. Int. 59(5), 563-576 (2010); and Irimai-Vladu, "Environmentally sustainable organic field effect transistors", Organic Electronics, 11, 1974-1990 (2010) disclose biodegradable electronic devices that may include a biodegradable organic conducting material and a biodegradable substrate. International Patent Application Publication WO 2008/108838 discloses biodegradable devices for delivering fluids and/or biological material to tissue. U.S. Patent Application Publication 2008/0306359 discloses ingestible devices for diagnostic and therapeutic applications. Kozicki et al., "Programmable metallization cell memory based on Ag—Ge—S and Cu—Ge—S solid electrolytes", NonVolatile Memory Technology Symposium, 83-89 (2005) discloses memory devices where metal ions within an electrolyte may be reduced or oxidized to form or remove solid metal interconnects.

SUMMARY OF THE INVENTION

Provided herein are transient devices, including active and passive devices that physically, chemically and/or electrically transform upon application of at least one internal and/or external stimulus and, particularly, methods of making those transient devices. Incorporation of degradable device components, degradable substrates and/or degradable encapsulating materials each having a programmable, controllable and/or selectable degradation rate provides a means of transforming the device. Any of the transient devices provided herein may combine degradable high performance single crystalline inorganic materials with selectively removable substrates and/or encapsulants. The methods provide a unique and reliable manufacturing method that is at least partly compatible with conventional electronics manufacture, particularly of high-performance semiconductor materials.

This description presents a set of materials, manufacturing approaches, device designs and system level examples for making a range of transient electronic devices. For example, included herein are transient electronic devices incorporating various components including inorganic semiconductor, metallic components, substrates and/or encapsulants. In particular, the processes and methods presented herein provide unique capabilities for retrieving and processing components from conventional sources, such as high-quality semiconductor materials and components from a semiconductor foundry. For example, the processes herein decouple those device components that are important for transience from requirements associated with conventional manufacturing processes, such as parameters and limitations found in a semiconductor foundry process, including cleanroom facilities. In this manner, conventional techniques may be used to obtain sophisticated and relatively expensive electronic components that are then processed in such a manner to ensure the desired transient characteristics or profile is obtained. Furthermore, nearly any class of materials may be incorporated into the electronic device, in contrast to conventional manufacturing methods where the material must fit into the processing conditions.

Incorporation of transfer printing with conventional wafer processing and manufacturing in some transient devices of the invention provides a means of engineering overall device properties to achieve a range of performance benefits. In some embodiments, for example, inorganic semiconductor components provide electronically active portions of the electrical device and other components are added or integrated to provide fine-tuned transient profiles, such as electrically conductive metals having precisely defined and preselected transience properties, such as transience profiles having well-defined temporal and physical properties useful for a range of applications. In some embodiments, for example, other structural components are included via follow-on processing, such as substrates and encapsulant layers, that are effective electronic insulating and/or barrier layers prior to a pre-engineered transient device transformation. In some embodiments, for example, substrates and encapsulant layers, undergo small dimensional changes prior to a pre-engineered transient device transformation, for example, in response to environmental conditions, e.g., exposure to water, biological fluid or other solvent, or in response to a user initiated trigger signal. In some embodiments, the substrate itself is a useful handle for the subsequent processing of the electronic device that will be formed from the components, such as by providing a handle to better access underlying components that otherwise are not readily physically accessible.

In an embodiment, provided herein are methods of making a transient electronic device. In an aspect, the method comprises the steps of fabricating one or more inorganic semiconductor components, one or more metallic conductor components or one or more inorganic semiconductor components and one or more metallic conductor components supported by a mother substrate. One or more inorganic semiconductor components or one or more metallic conductor components independently comprise a selectively transformable material and have a preselected transience profile. A handle substrate having a receiving surface is provided, wherein the receiving surface supports a release layer. The one or more inorganic semiconductor components, one or more metallic conductor components or one or more inorganic semiconductor components and one or more metallic conductor components are transfer printed from the mother substrate to the release layer supported by the handle substrate. The release layer on the handle layer is released. A substrate layer on top of the one or more inorganic semiconductor components, one or more metallic conductor components or one or more inorganic semiconductor components and one or more metallic conductor components is provided. The substrate layer and the one or more inorganic semiconductor components, one or more metallic conductor components or one or more inorganic semiconductor components and one or more metallic conductor components are released from the handle substrate. For example, a force may be applied to the substrate layer to release the underlying components from the handle substrate, so that both substrate and underlying components are together released. The substrate layer and the one or more inorganic semiconductor components, one or more metallic conductor components or one or more inorganic semiconductor components and one or more metallic conductor components are flipped to access an exposed surface of the one or more inorganic semiconductor components, one or more metallic conductor components or one or more inorganic semiconductor components and one or more metallic conductor components supported by the substrate layer. "Flipping" is used broadly and may refer functionally to the act wherein a previously physically inaccessible layer is accessible and amenable to additional processing, such as components that were previously sandwiched between two layers, such as a substrate layer and handle substrate. Accordingly, any of the methods provided herein optionally comprise the additional step of processing the exposed surface, including processing wherein a transient element of the electronic device is provided, thereby making the transient electronic device.

In an embodiment, a method of making a transient electronic device comprises the steps of: fabricating one or more inorganic semiconductor components, one or more metallic conductor components or one or more inorganic semiconductor components and one or more metallic conductor components supported by a mother substrate; wherein the one or more inorganic semiconductor components or one or more metallic conductor components independently comprise a selectively transformable material and have a preselected transience profile; providing a patterned substrate comprising one or more components of an electronic device on a receiving surface of the patterned substrate; transfer printing the one or more inorganic semiconductor components, one or more metallic conductor components or one or more inorganic semiconductor components and one or more metallic conductor components from the mother substrate to the receiving surface of the patterned substrate; and integrating the one or more inorganic semiconductor components, one or more metallic components or one or more inorganic semiconductor components and one or more metallic conductor components with the one or more electronic device components on the receiving surface of the patterned substrate, thereby making the transient electronic device.

In an aspect, the step of fabricating one or more inorganic semiconductor components, one or more metallic conductor components or one or more inorganic semiconductor components and one or more metallic conductor components supported by a mother substrate is carried out at a semiconductor foundry. In an aspect, the steps other than the step of fabricating one or more inorganic semiconductor components, one or more metallic conductor components or one or more inorganic semiconductor components and one or more metallic conductor components supported by a mother substrate are not carried out in a semiconductor foundry.

In an embodiment, any of the processing steps provided herein comprises adding a transient device component. Examples of transient device components include, but are not limited to, an electrode, an electrical interconnect, a semiconductor, an encapsulating layer, a barrier layer, or any combination thereof.

In an aspect, the processing step comprises replacing an inorganic semiconductor component with a transient inorganic semiconductor component; a metallic conductor component with a transient metallic conductor; or both. "Replacing" is used broadly herein and refers to a component that is removed and replaced or a component that is modified so that, functionally, an original non-transient component is replaced with a transient component. Accordingly, in an aspect the replacing comprises modifying a physical parameter of the inorganic semiconductor or metallic conductor to make a corresponding transient inorganic semiconductor or transient metal conductor. Examples of physical parameters useful in this context include one or more of: porosity, thickness, effective density, defect density, dopant concentration, composition, or morphology.

In an embodiment, the processing step comprises providing a transient substrate.

In an embodiment, the processing step comprises encapsulating at least a portion of the exposed surface with an encapsulating layer, such as an encapsulating layer that comprises a selectively removable material that is at least partially removed in response to an external or internal stimulus. Examples of selectively removable material of the encapsulating layer include a material selected from the group consisting of a polymer, a metal, a metal oxide, a glass and a ceramic. In an aspect any of the encapsulating layer, the substrate and at least a portion of the one or more inorganic semiconductor components or the one or more metallic conductor components, each independently comprise a selectively transformable material, thereby providing an electronic device that is transient.

In another aspect, processing the exposed surface comprises providing one or more interconnect structures for electrically interconnecting the one or more semiconductor components, wherein the interconnect structures independently comprise a selectively transformable material and have a preselected transience profile. Examples of electrically interconnecting include patterning a transient metal that is W or Mo. The interconnect structures may be provided via physical vapor deposition, chemical vapor deposition, sputtering, atomic layer deposition, electrochemical deposition, spin casting, ink jet printing, electrohydrodynamic jet printing, screen printing or any combination thereof.

Any of the methods provided herein may further comprise the step of integrating a transient passive component, a transient active component, or both, with the one or more inorganic semiconductor components. The integrating step may be carried out after the step of flipping the substrate layer. Alternatively, or additionally, the integrating step is part of the fabricating step.

Any of the methods further comprise providing a protective layer between the release layer and the one or more inorganic semiconductor components, one or more metallic conductor components or one or more inorganic semiconductor components and one or more metallic conductor components. The protective layer is useful for removal of a release layer without substantial degradation of the one or more inorganic semiconductor components, one or more metallic conductor components or one or more inorganic semiconductor components and one or more metallic conductor components. Examples of a protective layer include, but are not limited to, a polymer layer in contact with the one or more inorganic semiconductor components, one or more metallic conductor components or one or more inorganic semiconductor components and one or more metallic conductor components.

In an aspect, the fabricating step of any of the methods provided herein comprises forming a plurality of semiconductor components on the mother substrate. The plurality may number from between 2 to about 10,000 or more, such as 2 to 100,000,000, 2 to 100,000 , or between about 10 and 100,000 , depending on the application of interest. In an aspect the fabricating step further comprises undercutting the semiconductor components, such as to provide components that are printable. In an embodiment, the plurality of semiconductor components are freestanding on the mother substrate and connected to the mother substrate by one or more anchors.

In an aspect, the mother substrate comprises a silicon-on-insulator (SOI) wafer, such as SOI wafer having a <111> orientation.

In an embodiment, the SOI wafer comprises: a silicon handle wafer having a <111> orientation; a buried insulator layer; and a top layer of active Si having a <100> orientation from which the one or more semiconductor components are formed. The method may further comprise the step of: etching the Si <111> handle wafer to facilitate release of the one or more semiconductor device elements that comprise Si <100> from the mother substrate. In an aspect, the SOI wafer comprises a commercial quality SOI wafer that is coated with the buried insulator layer that is an oxide layer, and the oxide layer is bonded to a bulk <111>-oriented silicon wafer, such as an oxide layer that comprises silicon dioxide.

In an aspect, the transfer printing comprises dry transfer contact printing. Alternatively, the contact printing comprises solution printing. In an embodiment, the dry transfer printing further comprises contacting the one or more components with a transfer device; removing the transfer device and the one or more components from the donor substrate; contacting the transfer device and the one or more components to the handle substrate; and removing the transfer device without the components, thereby transferring the one or more components to the handle substrate. Examples of a transfer device include an elastomeric stamp, a conformable stamp that conforms and contacts the components, such as a material having an adhesive affixed to a contact surface (e.g., adhesive tape).

In an embodiment, the transfer printing is high throughput and high fidelity, thereby providing efficiently and reliably a large number of components in one or more printing steps.

In an aspect, the handle substrate comprises a Si wafer.

The method is compatible with a range of means for providing the substrate layer on top of the one or more inorganic semiconductor components, one or more metallic conductor components or one or more inorganic semiconductor components and one or more metallic conductor components. Examples include by spin casting or lamination of a material. The material of the substrate layer may be a polymer, metal, metal oxide, ceramic or glass to a surface of the one or more metallic conductor components or one or more inorganic semiconductor components and one or more metallic conductor components. The polymer may be an organic polymer, poly(lactic-co-glycolic acid) (PLGA), or polydimethylsiloxane (PDMS). The substrate layer may be provided before or after the etching step.

In an aspect, the substrate layer comprises a selectively transformable material, such as a material having a user-selected degradation characteristic in a defined environmental setting. The degradation characteristic may be a degradation rate that is at least partially dependent on a physical parameter of the surrounding environment, such as temperature, humidity, water or other liquid, light, or a physical force exerted against the device by the surrounding environment. Degradation rate may refer to the amount of material lost per unit time, or change in average thickness with time of the device, component, or layer thereof.

Optionally, any of the methods provided herein comprise an additional transfer step such as by transferring the one or more inorganic semiconductor components, one or more metallic conductor components or one or more inorganic semiconductor components and one or more metallic conductor components from the substrate layer to a receiving substrate by contact printing with the substrate layer directly or via another transfer substrate.

In an embodiment, the substrate layer has a mechanical property to facilitate handling and flipping without damage to the one or more inorganic semiconductor components, one or more metallic conductor components or one or more inorganic semiconductor components and one or more metallic conductor components. This mechanical property may be described as one or more of Young's modulus, bending stiffness or rigidity.

In an aspect, the step of releasing the substrate layer and the one or more inorganic semiconductor components, one or more metallic conductor components or one or more inorganic semiconductor components and one or more metallic conductor components from the handle substrate comprises applying a removal force to the substrate layer in a direction away from the handle substrate.

In another embodiment, the step of releasing the substrate layer and the one or more inorganic semiconductor components, one or more metallic conductor components or one or more inorganic semiconductor components and one or more metallic conductor components from the handle substrate comprises peeling the substrate layer in a direction away from the handle substrate.

In an aspect, the substrate layer functions as a handle for separating the one or more inorganic semiconductor components, one or more metallic conductor components or one or more inorganic semiconductor components and one or more metallic conductor components from the handle substrate. Accordingly, the substrate may have two unique and important functions in certain embodiments: (1) the application of forces for removal without damaging the underlying fragile mechanical components; and (2) as a substrate of a transient mechanical device. Such dual-purpose functionality is beneficial in terms of reducing processing, increasing reliability and, therefore, reducing manufacturing cost.

In an aspect, the substrate handle functions as a handle for transferring the one or more inorganic semiconductor components, one or more metallic conductor components or one or more inorganic semiconductor components and one or more metallic conductor components to a receiving substrate having a receiving surface.

In an aspect, the release layer comprises a polymer layer, or a layer of poly(methylmethacrylate) (PMMA).

The releasing step optionally comprises a two-step dry and wet process to facilitate removal of the substrate layer and the one or more inorganic semiconductor components, one or more metallic conductor components or one or more inorganic semiconductor components and one or more metallic conductor components from the handle wafer.

The methods provided herein may utilize a range of transience profiles such as by adjusting any one or more of a number of physical parameters, including: a thickness of the semiconductor or the metallic conductor components; a density of the semiconductor or the metallic conductor components; a defect density of the semiconductor or the metallic conductor components; a composition of the semiconductor or the metallic conductor components; a porosity of the semiconductor or the metallic conductor components; a crystallinity of the semiconductor or the metallic conductor components; a dopant of the semiconductor or the metallic conductor components; or a morphology of the semiconductor or the metallic conductor components.

In an aspect, the one or more metallic conductor components are independently selected from the group consisting of Mg, Mo, W, Fe, Zn and alloys thereof.

In an aspect, the method comprises fabricating a plurality of inorganic semiconductor components. Furthermore, the processing step may comprise providing one or more metallic components.

Examples of the one or more metallic components are interconnects that electrically interconnect one or more semiconductor components. The interconnects may be transient such that they degrade with time, thereby degrading and ending electronic device functionality. Further electronic device degradation may be achieved by degradation of the substrate so that device integrity is lost such as by environmental forces that exert forces on fragile portions of the device to physically break up the device and/or degradation of semiconductor components.

In an aspect, the metallic components comprise electrodes in electrical communication with the one or more semiconductor components.

Any of the metallic components may be provided by a deposition technique, such as by physical vapor deposition, chemical vapor deposition, sputtering, epitaxial growth, atomic layer deposition, electrochemical deposition, electrohydrodynamic jet printing, or molecular beam epitaxy.

Any of the one or more inorganic semiconductor components or one or more metallic conductor components is microsized, such as having a lateral dimension that is greater than or equal to 5 µm and less than or equal to 500 µm.

In an aspect, the transient electronic device comprises a metal-oxide semiconductor field-effect transistor (MOSFET); a complementary metal-oxide-semiconductor (CMOS), a transistor, a capacitive sensor, a diode, a photodector, or a capacitor. In an aspect, the transient electronic device is a communication system, a photonic device, a sensor, an optoelectronic device, a biomedical device, a temperature sensor, a photodetector, a photovoltaic device, a strain gauge, an imaging system, a wireless transmitter, an antenna, a battery, a nanoelectromechanical system or a microelectromechanical system.

In an embodiment, any of the methods provided herein are for a plurality of semiconductor components or a plurality of metallic conductor components that are simultaneously transferred to the handle wafer, wherein the plurality is selected from a range that is greater than or equal to 2 components and less than or equal to 100,000,000 components. The methods and systems of the present invention are compatible with a range of receiving substrate compositions including polymer, ceramic, metal, semiconductor, paper, and glass substrates, substrate geometries including planar and contoured substrates, and substrate surface morphologies including smooth and rough substrates, depending on the desired application in which the transient electronic device is employed.

The invention is particularly useful for generating patterns of components on surfaces of substrates exhibiting excellent reproducibility, pattern fidelity and resolution. In an aspect, the high throughput patterning is for large receiving substrate areas (greater than or equal to about 232 $cm^2$) and, thus, provides a robust and commercially attractive manufacturing pathway to a range of transient functional systems and transient devices including electronic device arrays, nano- and micro-electromechanical systems, nano and micro-biological systems, sensors, energy storage devices and integrated electronic circuits. Further, nanopatterning and micropatterning methods and systems of the present invention are compatible with a wide range of substrates and materials, including semiconductors, wafers, metals, metal alloys, semimetals, insulators, crystalline materials, amorphous materials, biological materials, and the methods can be employed under a wide range of processing conditions, including low temperature (<about 400 degrees Celsius) processing.

In an embodiment, at least a portion or all the printable components is transferred with good fidelity. For example, transferred to a selected region of the receiving surface with a placement accuracy better than or equal to about 25 µm, about 10 µm or about 1 µm over a receiving surface area, such as surface area of about 5 $mm^2$, 5 $cm^2$, about 5 $m^2$, or a surface area that is selected from a range that is greater than or equal to 5 $mm^2$ and less than or equal 5 $m^2$.

In an aspect, the one or more inorganic semiconductor components or the one or more metallic conductor components independently comprise one or more thin film structures, such as a thin film structure with a thickness selected over a range that is greater than or equal to 10 nm and less than or equal to 100 µm.

In an aspect, any of the methods relate to a transient electronic device that degrades in response to an environmental signal or condition. For example, exposure to liquid, water, biological fluid, temperature, humidity, irradiation, solar (e.g., UV) exposure may begin degradation of the transient electronic device. Optionally, fine control of device degradation is achieved by providing a well-controlled outer layer (e.g., substrate, barrier layer, encapsulant layer) that protects sensitive internal components, but upon degradation of the outer layer or portion thereof, the sensitive interior components more rapidly degrade. Such a system is referred herein as a composite transient system in that different functional portions of the device have different transience profiles. In an aspect, there may be a more active control of degradation by providing a user-initiated signal, similar to a self-destruct command. Accordingly, any of the methods and devices provided herein may be directed to a transient electronic device that degrades in response to a user-initiated signal. For example, a wireless transmission may engage an actuator such as a thermal or electrical generation to actively degrade the transient device.

In an embodiment, the selectively transformable material has an effective electrical dissolution rate, defined by changes associated with an effective change in the thickness, selected from the range of 0.01 nm/day to 100 µm/s, 0.1 nm/day to 10 µm/s, or about 1 nm/day to 1 µm/s.

In an aspect, the preselected transience profile is characterized by one or more of: a transformation of 0.01% to 100%, 0.1% to 95%, or 5% to 95% of said one or more inorganic semiconductor components or said one or more metallic conductor components over a time interval selected from the range of 1 ms to 5 years, 1 second to 1 year, or 1 minute to 6 months; a decrease in average thickness of said one or more inorganic semiconductor components or said one or more metallic conductor components at a rate selected over the range of 0.01 nm/day to 100 microns $s^{-1}$, 0.1 nm/day to 1 µm/s, or 1 nm/day to 1 µm/s; a decrease in electrical conductivity of said one or more inorganic semiconductor components or said one or more metallic conductor components at a rate selected over the range of $10^{10}$ $S·m^{-1} s^{-1}$ to 1 $S·m^{-1} s^{-1}$; a change in morphology of said one or more inorganic semiconductor components or said one or more metallic conductor components, said change in morphology selected from the group consisting of pitting, flaking, cracking and uniform degradation; a percentage decrease in density of said one or more inorganic semiconductor components or said one or more metallic conductor components selected over the range of 0.01% to 99.9%, 0.1% to 99%, or 1% to 95%; or a percentage increase in porosity of said one or more inorganic semiconductor components or said one or more metallic conductor components selected over the range of 0.01% to 99.9%, 0.1% to 99%, or 1% to 95%.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

at various times during immersion in DI water at room temperature. The linear scale transfer curves (left), and the drain current ($V_d$=0.1 V, $V_g$=5 V) show that electrical properties of the device are invariant for ~8 hours. Afterward, the performance degrades completely within ~1 hour. b) Measured characteristics of an n-channel inverter encapsulated with MgO (~800 nm) at different times in DI water at room temperature. Voltage transfer characteristics (left), and output voltages at $V_g$=-2 V and gain (right) measured during dissolution. The device operation is stable for ~7 hours, followed by rapid degradation in ~50 min.

Figure 6:
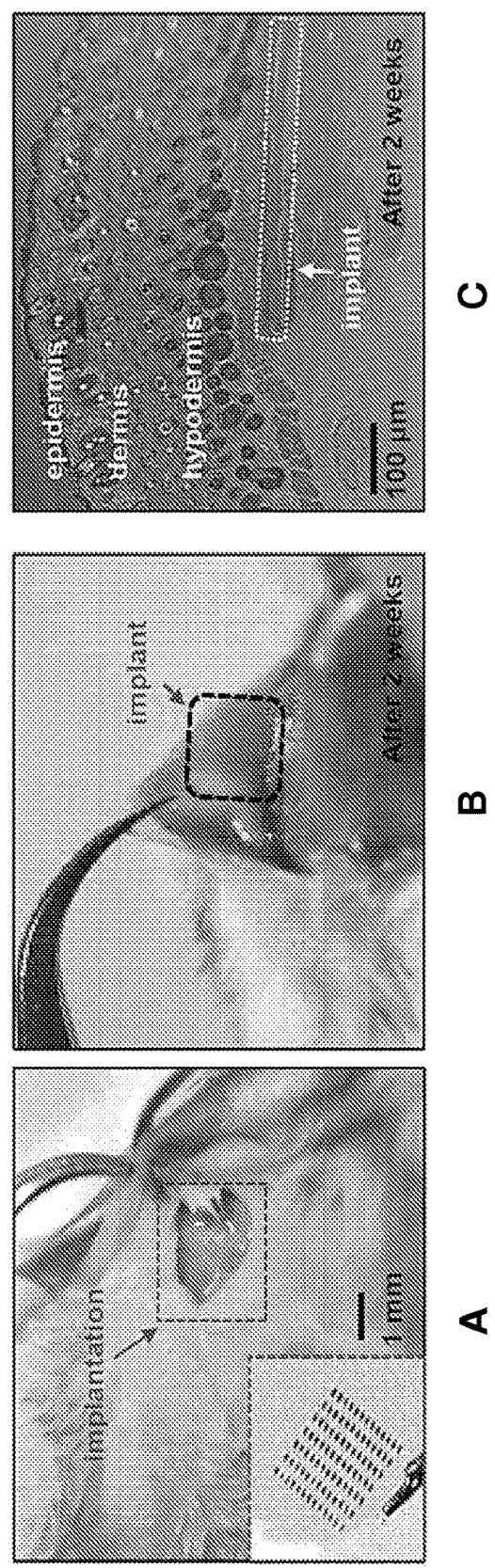

FIG. 6. In vivo animal evaluation of biocompatibility. a) Image of the subcutaneous implantation of a representative device, consisting of an array of transistors on a sheet of silk, in the dorsal region of a BALB/c mouse. b) Image of the implant site after 2 weeks, showing that the implant integrated into the surrounding tissues with no signs of the transistors. c) Histological examination of the tissue surrounding the implant site reveals the absence of any inflammatory response.

Figure 7:
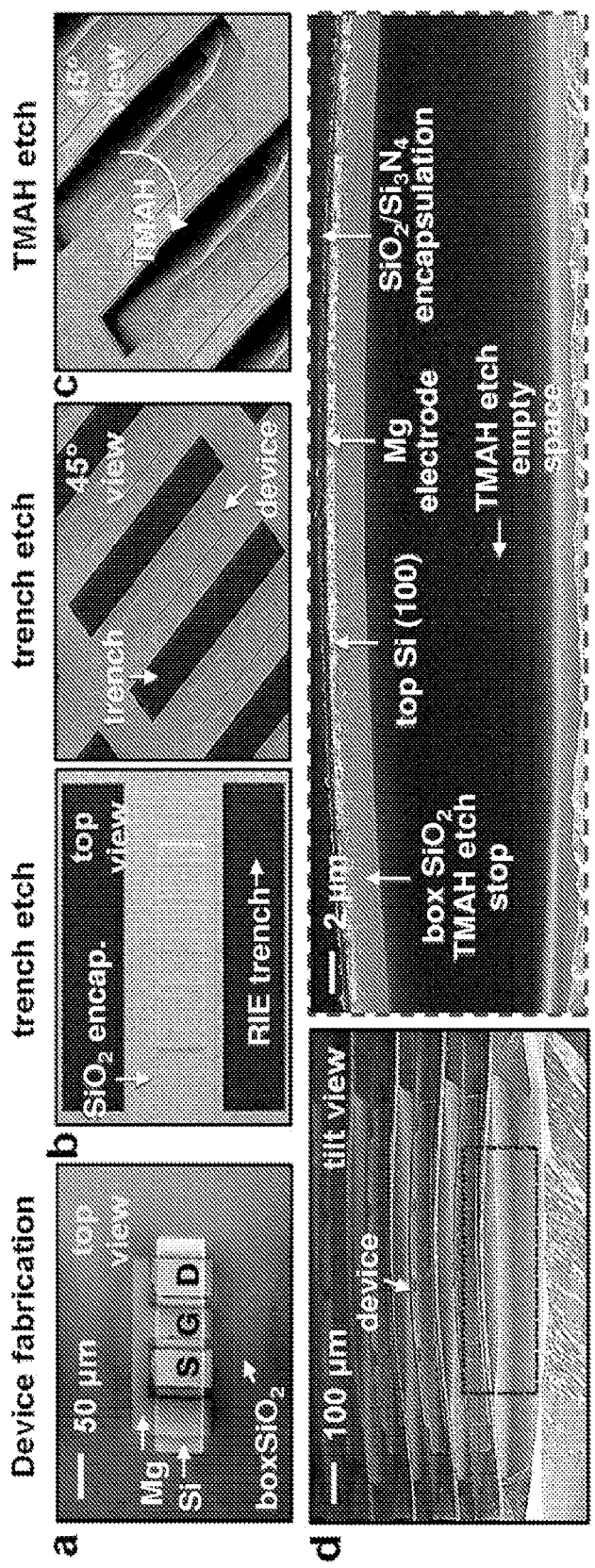

FIG. 7. Scanning electron microscope (SEM) images showing fabrication processes of n-channel metal oxide semiconductor field effect transistors (MOSFETs), (a) metallization, (b) RIE trench etch and (c) tetramethylammonium hydroxide (TMAH) solution etch. (d) Cross-section view of device using scanning electron microscopy (SEM) after anisotropic TMAH etch (left) and its magnified view (right). The thickness of entire layers is less than 2 μm.

Figure 8:
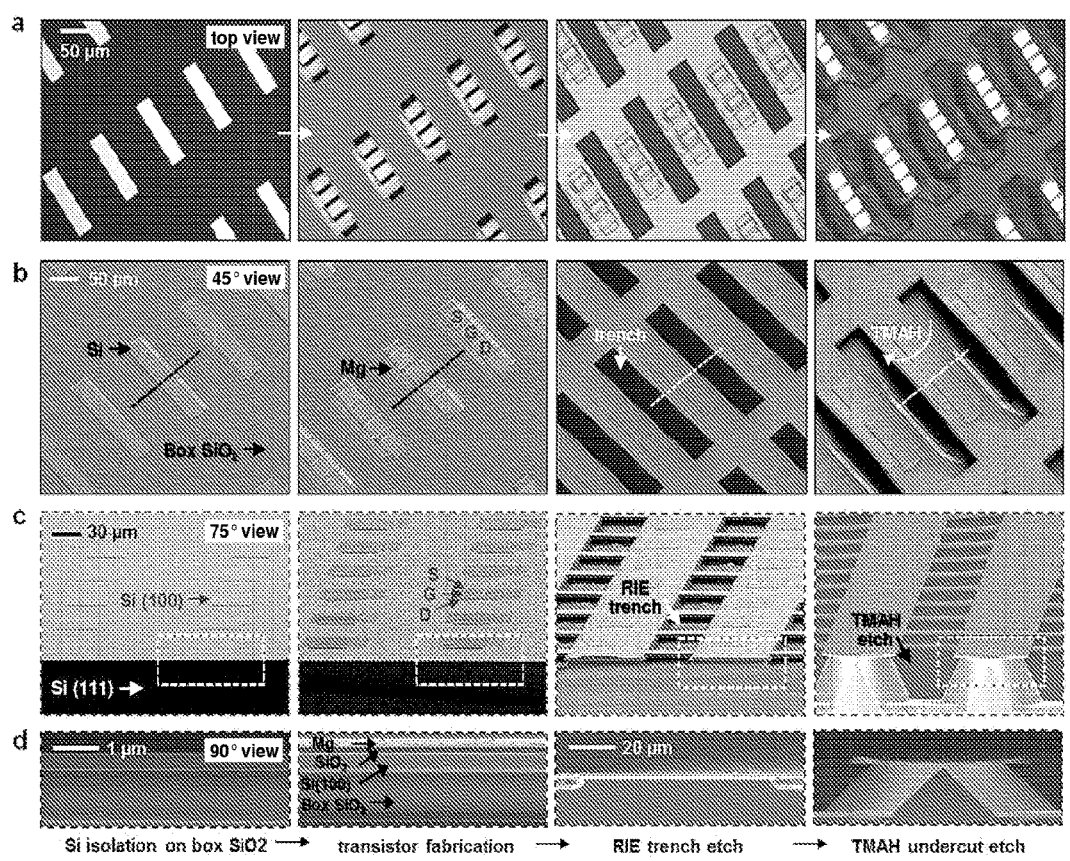

FIG. 8. Detailed fabrication process of fully biodegradable transistor array. Device isolation, metallization, RIE trench etch, and anisotropic TMAH undercut etch (from left to right). (a) Optical microscope images of fabrication process of n-channel transistor array. (b) Images of scanning electron microscopy (SEM) showing n-MOSFETs fabrication process at angled view. (c) A set of images describing fabrication of device array at tilted view. (d) Cross-sectional images of each fabrication step of a n-channel MOSFET.

Figure 9:
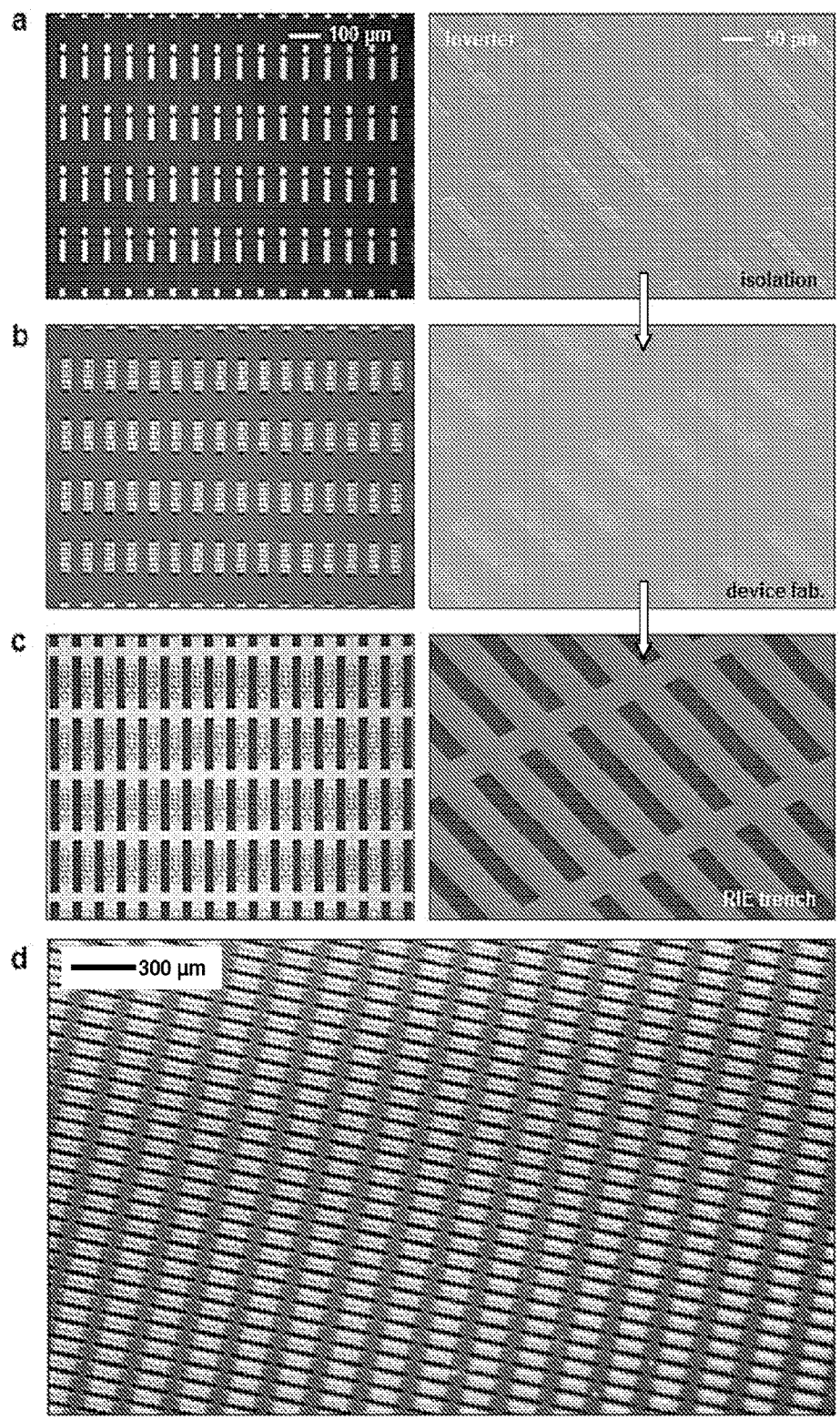

FIG. 9. Images of fabrication process of n-channel transistor inverter. (a) device isolation, (b) metallization, (c) RIE trench etch, (d) TMAH etch.

Figure 10:
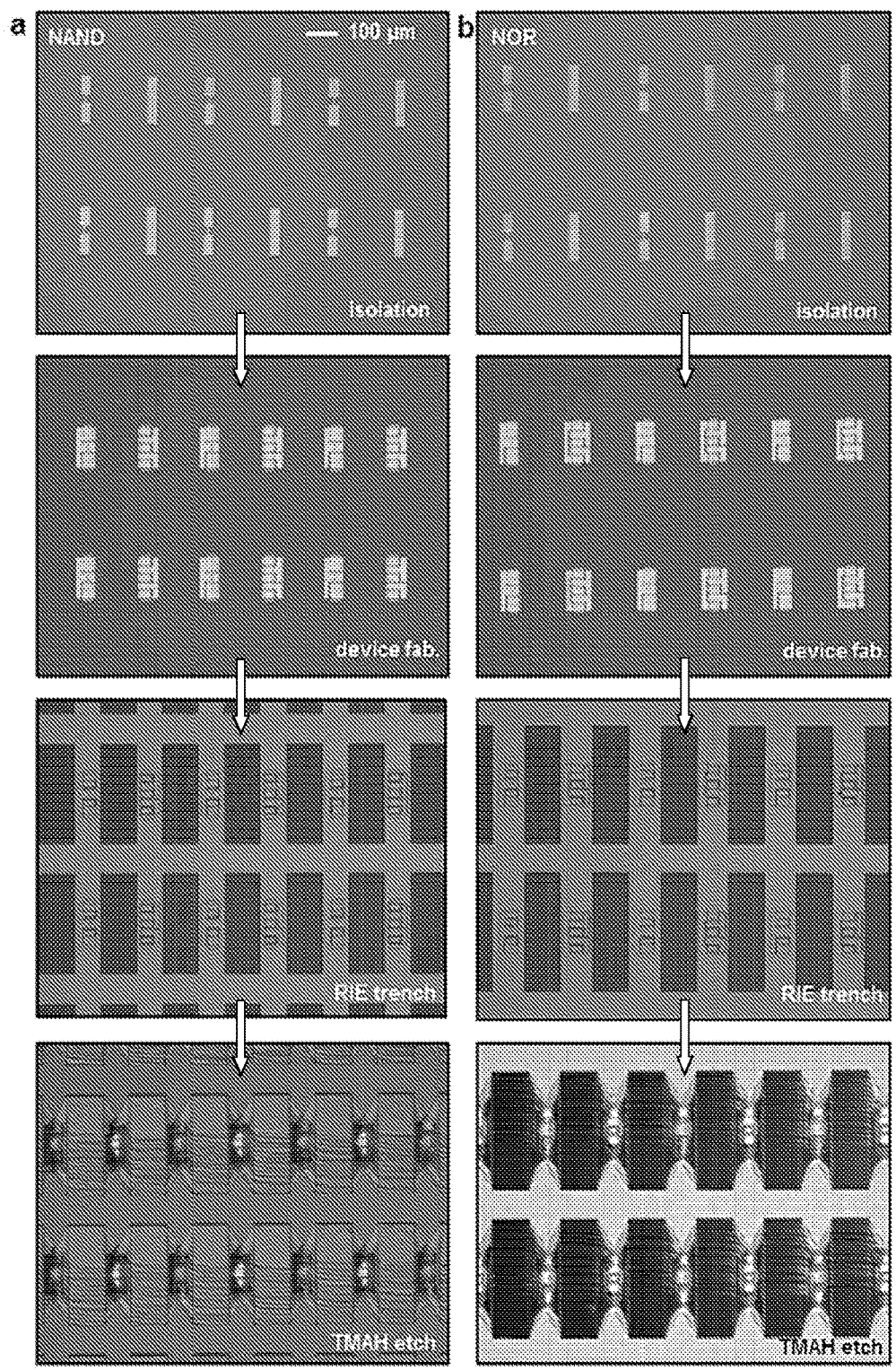

FIG. 10. Optical microscope images showing fabrication process of logic gates, device isolation, metallization, RIE trench etch and anisotropic TMAH solution etch (from top to bottom). (a) NAND, (b) NOR.

Figure 11:
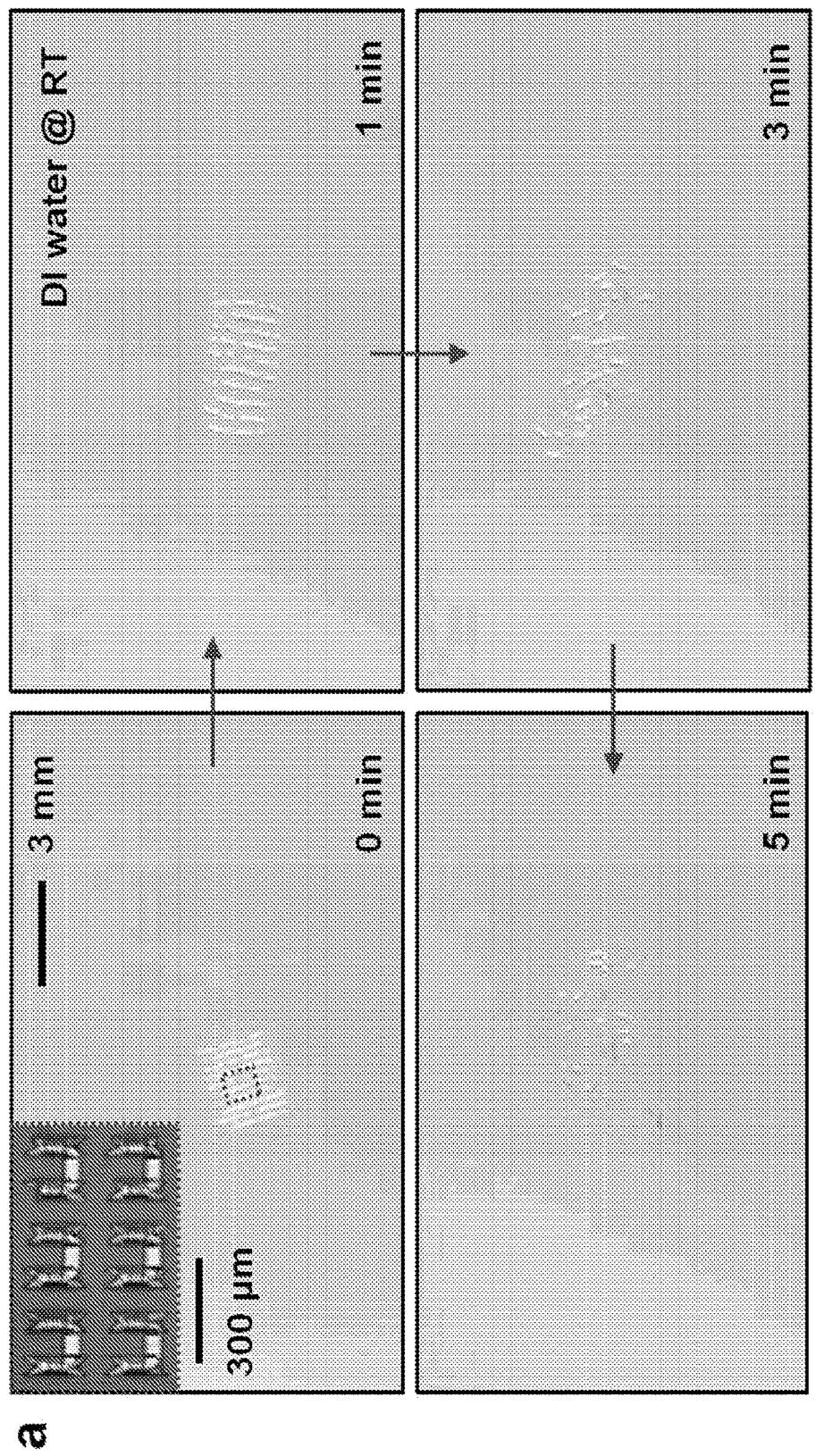

FIG. 11. A collection of dissolution images of logic gates (NAND) submerged in DI water at room temperature at 0 min, 1 min, 3 min, and 5 min, respectively. Inset shows a magnified optical image of devices.

Figure 12:
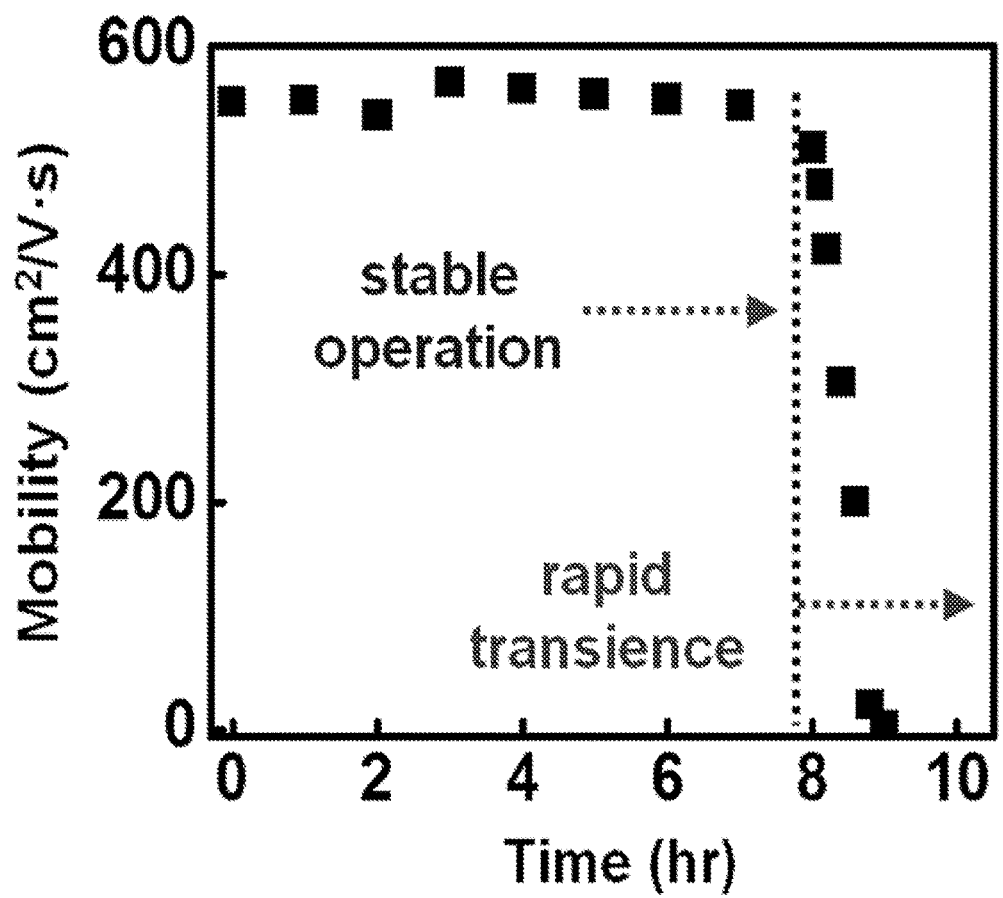

FIG. 12. The change of calculated mobility in n-type transistors encapsulated with MgO (~800 nm) while submerged in DI water at room temperature.

Figure 13:
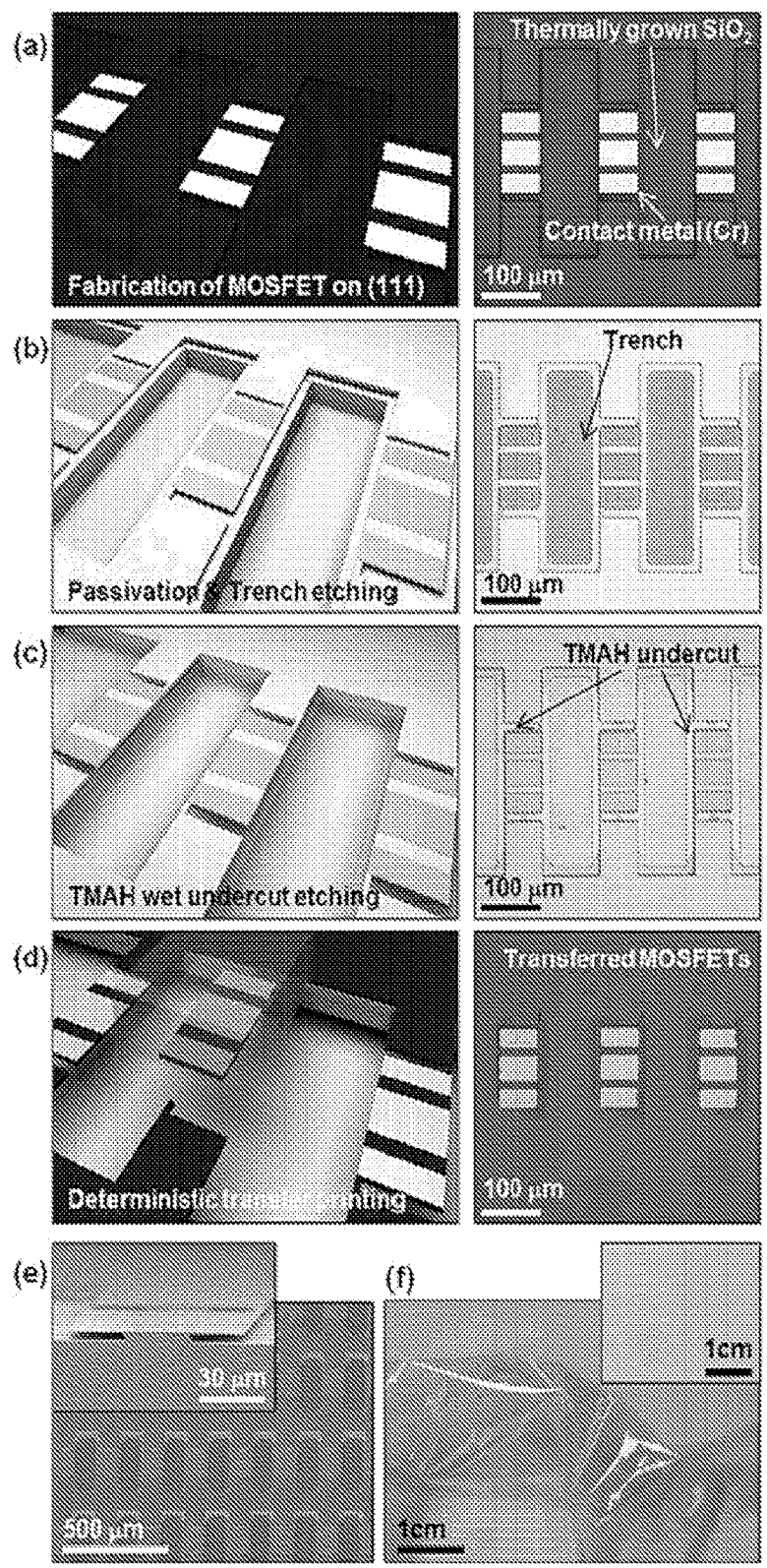

FIG. 13. Schematic illustrations and optical microscope images of steps for forming releasable single crystal silicon MOSFETs on bulk wafers and their deterministic assembly on foreign substrates by transfer printing, including (a) fabrication of single crystal silicon MOSFETs oriented along the <100> direction on the surface of a bulk (111) wafer, with thermal gate oxide and metallization for source/drain and gate electrodes, (b) uniform deposition of a layer of $SiN_x$ followed by etching of trenches between the devices, (c) wet anisotropic undercut etching using TMAH, (d) manipulation of MOSFETs by transfer printing and (e) inset SEM images of devices completely and partially undercut. (f) 150 MOSFETs fabricated in this manner after transfer printing onto a substrate of ultrathin PET with thickness of 2.5 μm. The devices were printed in 9 by 10 arrays with 1 mm pitch (bottom left), 5 by 5 arrays with 2 mm pitch (top left), and 7 by 5 arrays with 4 mm pitch as shown in inset image.

Figure 14:
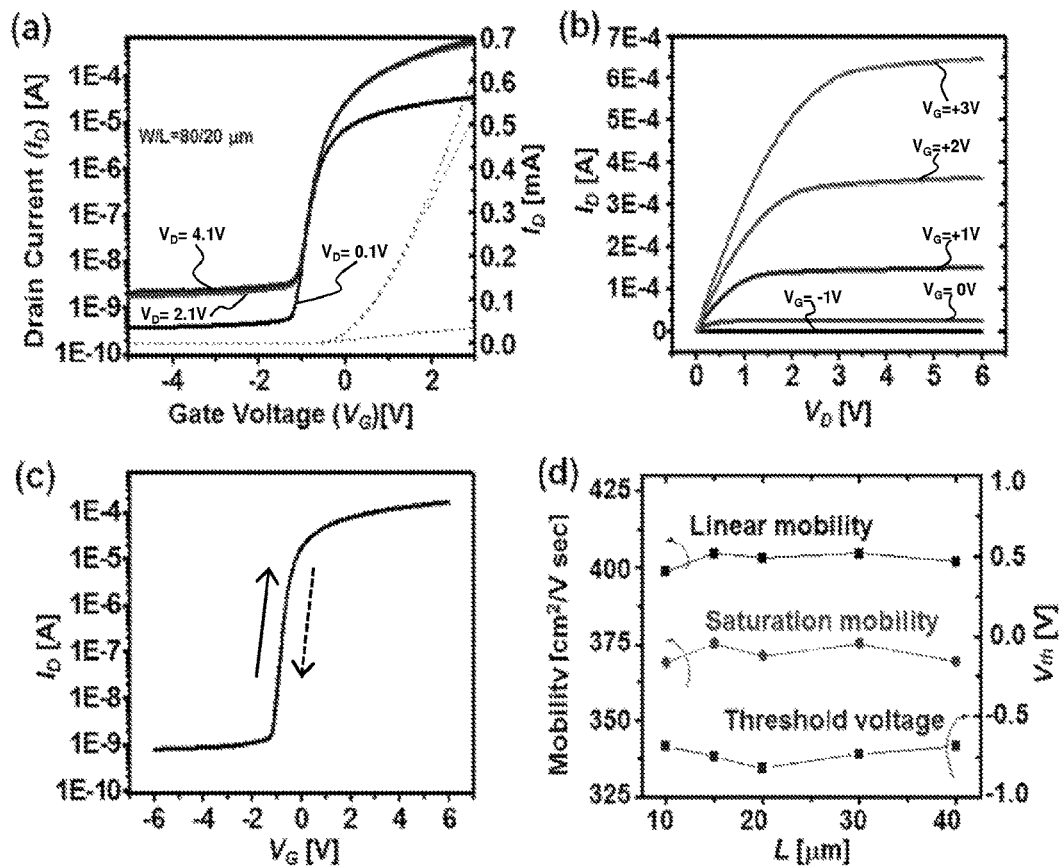

FIG. 14. (a) Transfer characteristics of a MOSFET with W/L=80/20 um printed onto a sheet of polyimide. Colored solid and dashed lines correspond to drain currents at various drain voltages in logarithmic and linear scales, respectively. (b) Output characteristics at increasing gate voltages. (c) Transfer characteristics measured with gate voltage sweeps from negative to positive (black) and from positive to negative (red). (d) Linear and saturation mobility and threshold voltage as a function of channel length.

Figure 15:
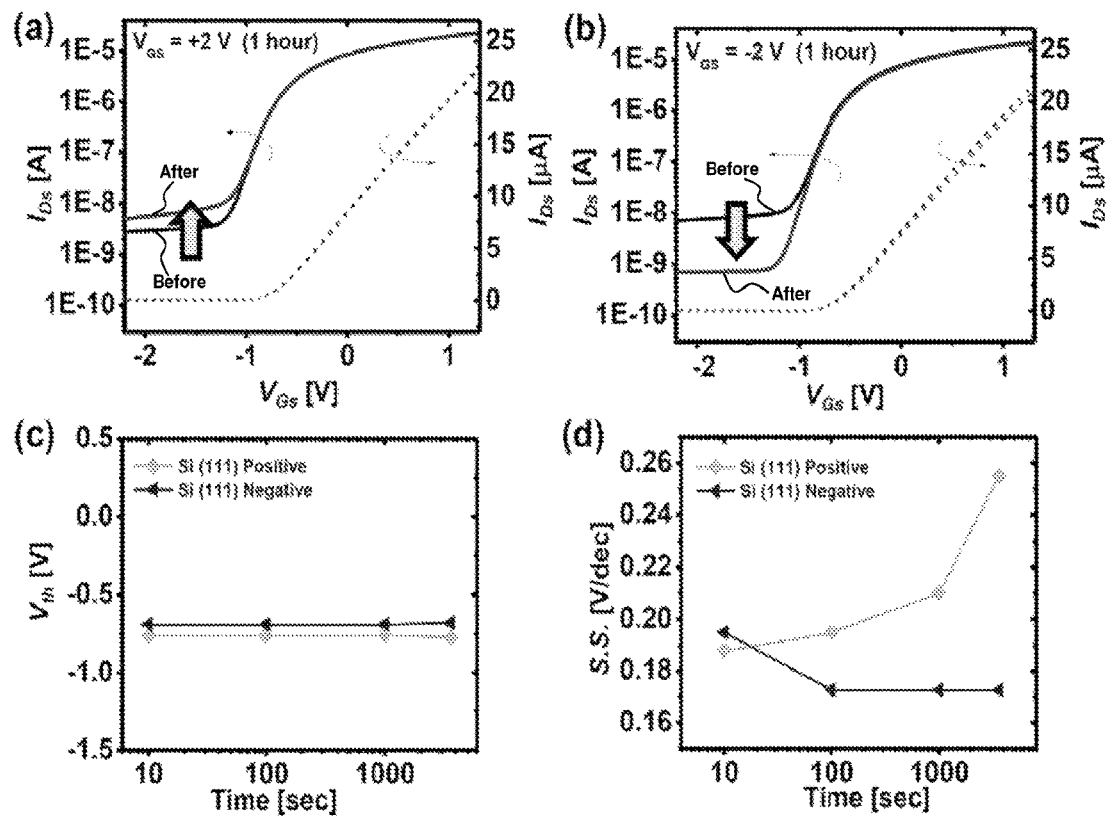

FIG. 15. Transfer characteristics of a MOSFET printed onto a polyimide substrate after (a) positive and (b) negative biases applied on the gate electrode for an hour. Variation in (c) threshold voltage ($V_{th}$) and (d) subthreshold slope (S.S.) as a function of duration of bias stress.

Figure 16:
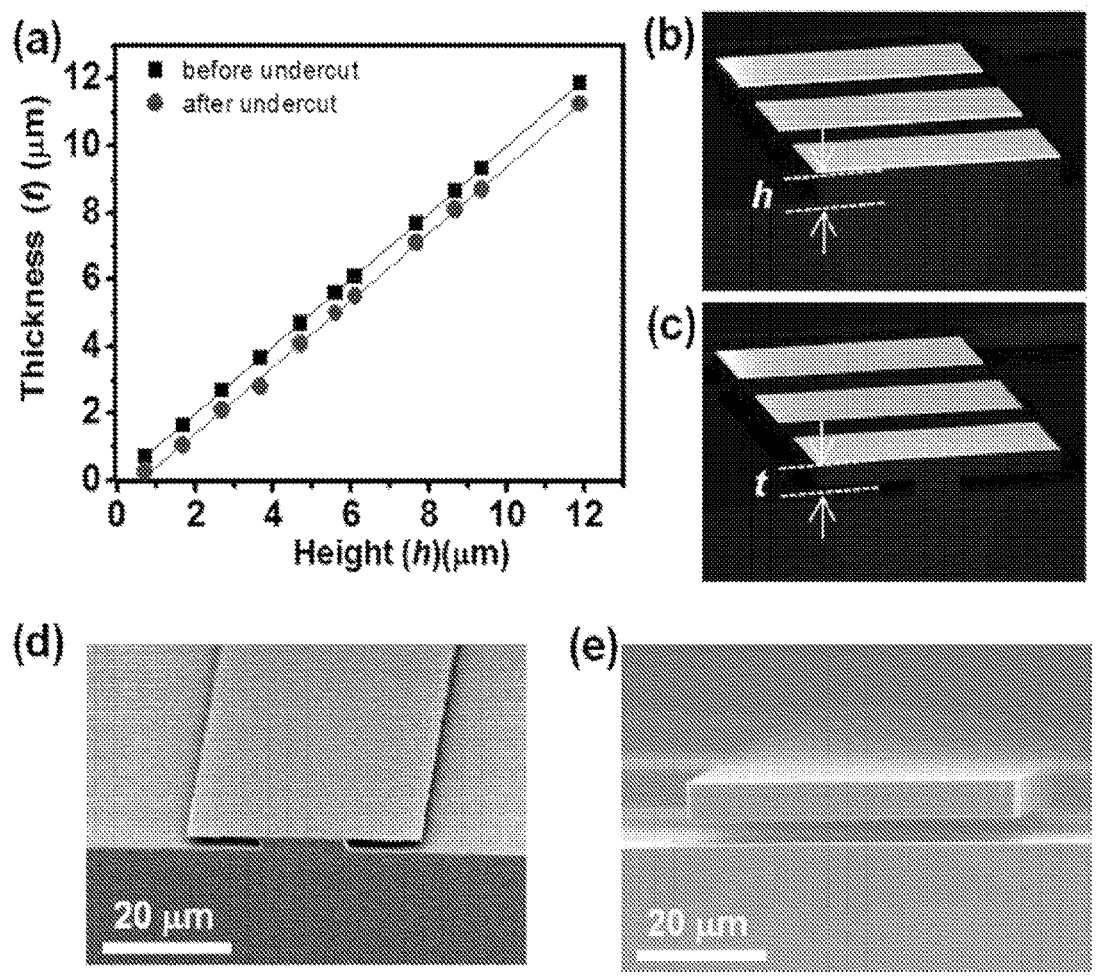

FIG. 16. Capabilities for achieving thicknesses of released device silicon, from several microns to several hundred nanometers. (a) Depth of initial trench (black dots; frame b) and undercut device thickness (red dots; frame c) after wet anisotropic undercut etching (TMAH, for 60 min at 100° C.). Cross sectional views of representative results, at thicknesses of 800 nm (d) and 11 μm (e).

Figure 17:
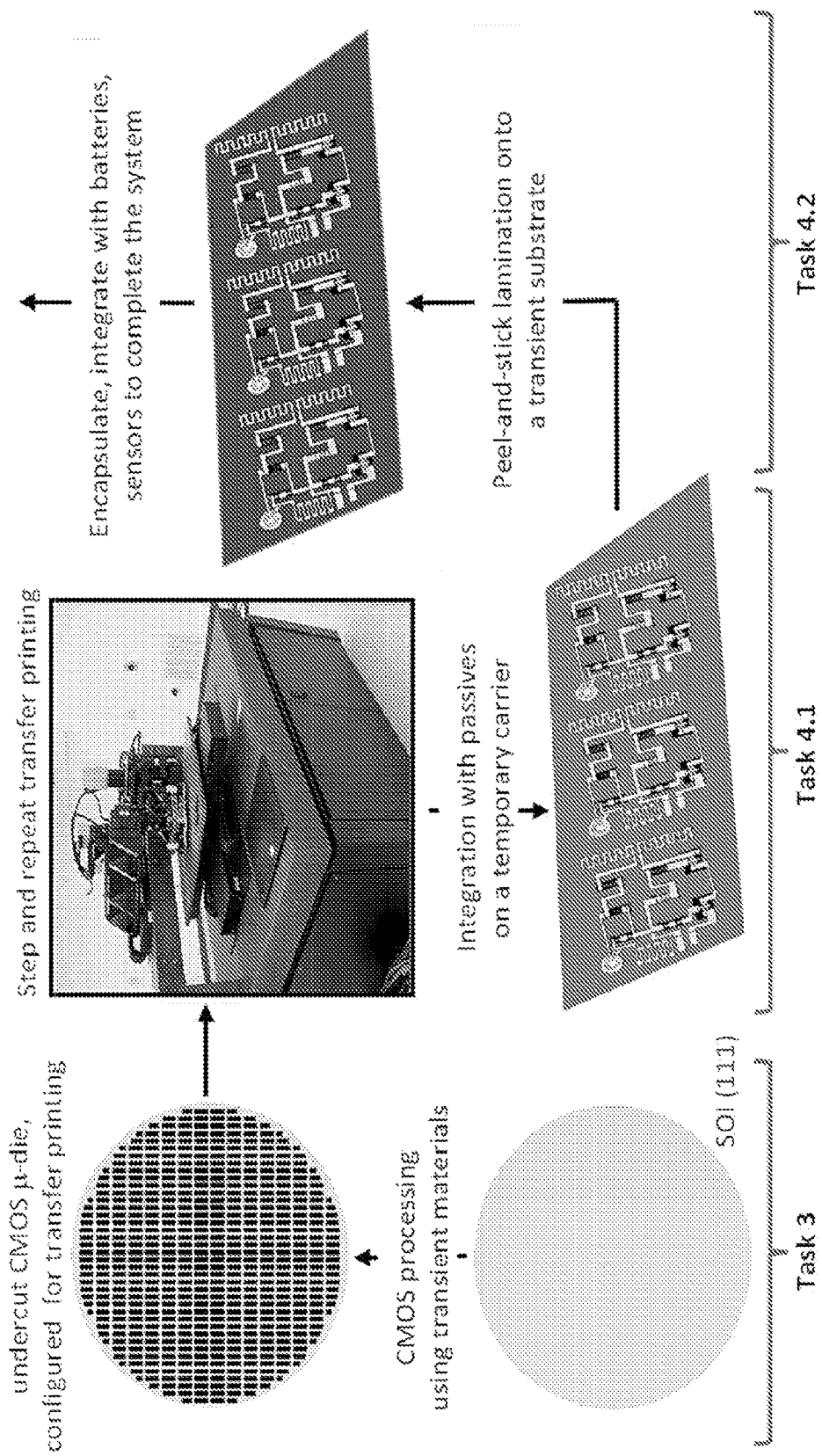

FIG. 17. Schematic illustration of a manufacturing flow for transient electronics. Transfer printing of transient CMOS μ-die onto a temporary carrier substrate enables interconnection and integration with transient passives formed by thin film processing. Peel-and-stick lamination onto a transient substrate followed by removal of sacrificial materials prepares the system for packaging and integration with batteries and sensors.

Figure 18:
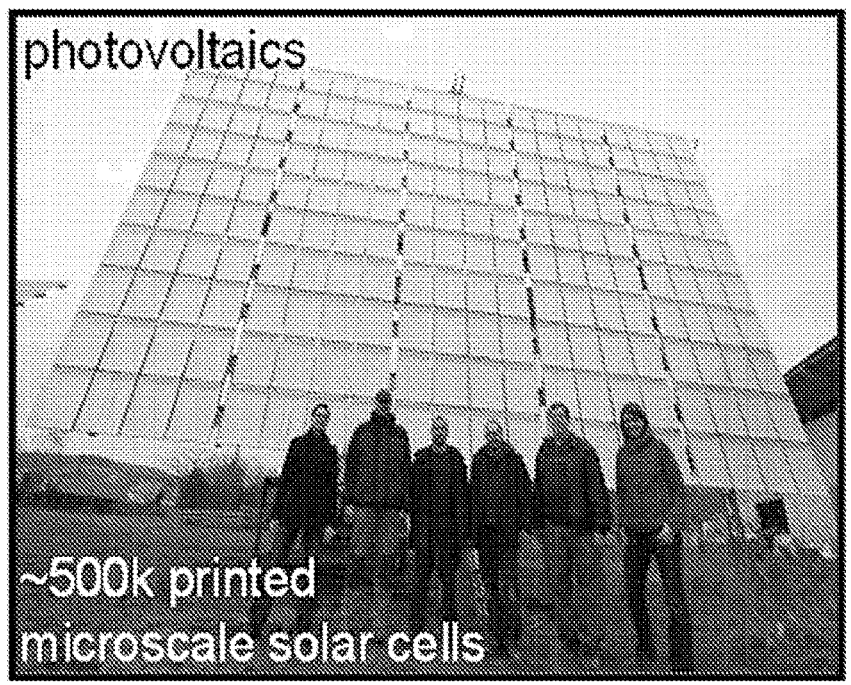
Figure 18:
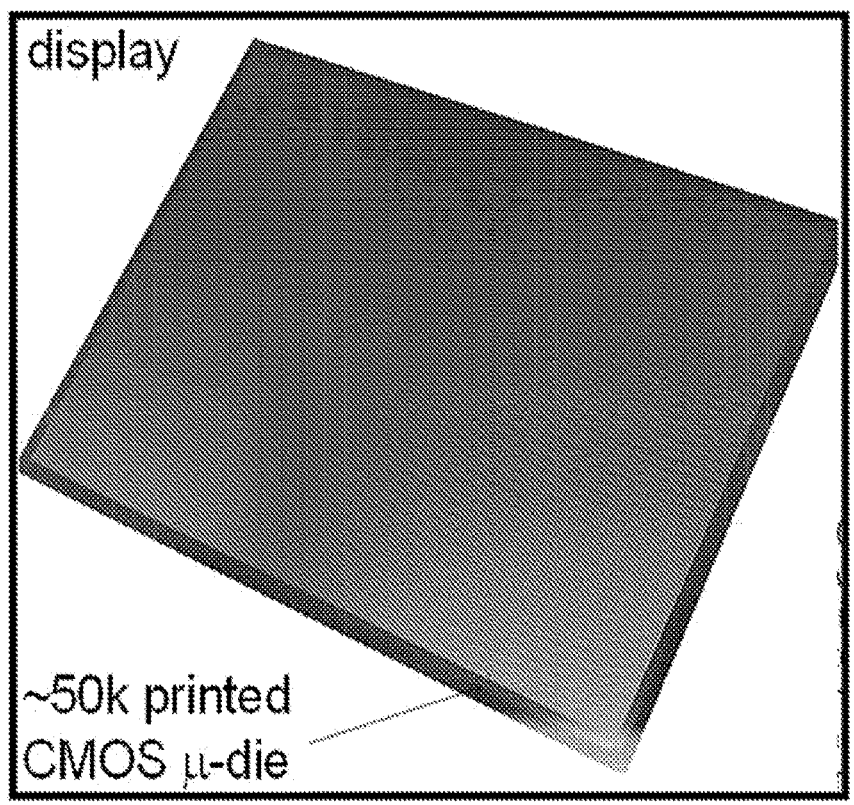

FIG. 18. Examples of large-scale commercial systems manufactured using transfer printing.

Figure 19:
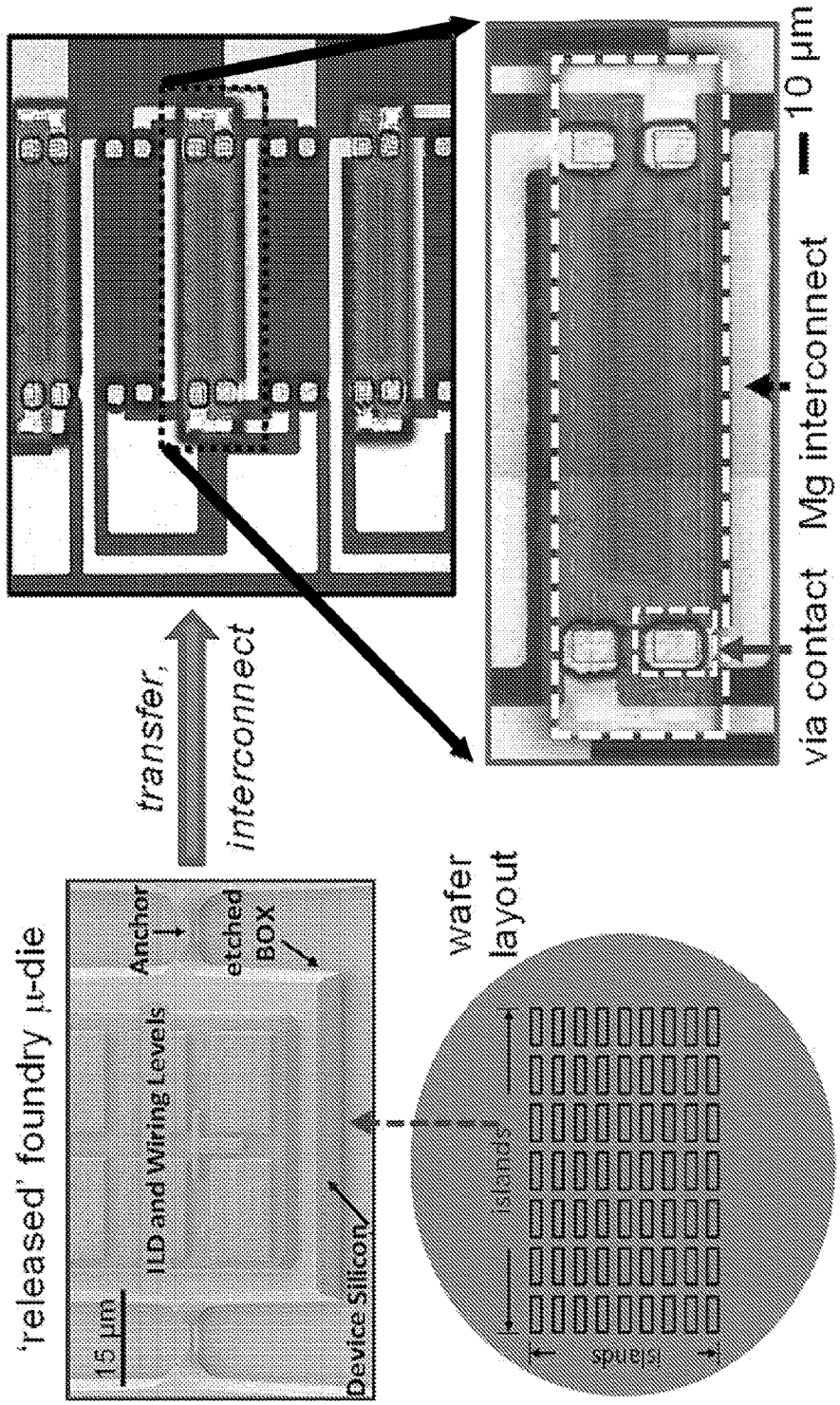

FIG. 19. Example of transfer printing of CMOS μ-die from a foundry source wafer (X-FAB) onto a glass substrate, followed by interconnection with a transient metal (Mg).

Figure 20:
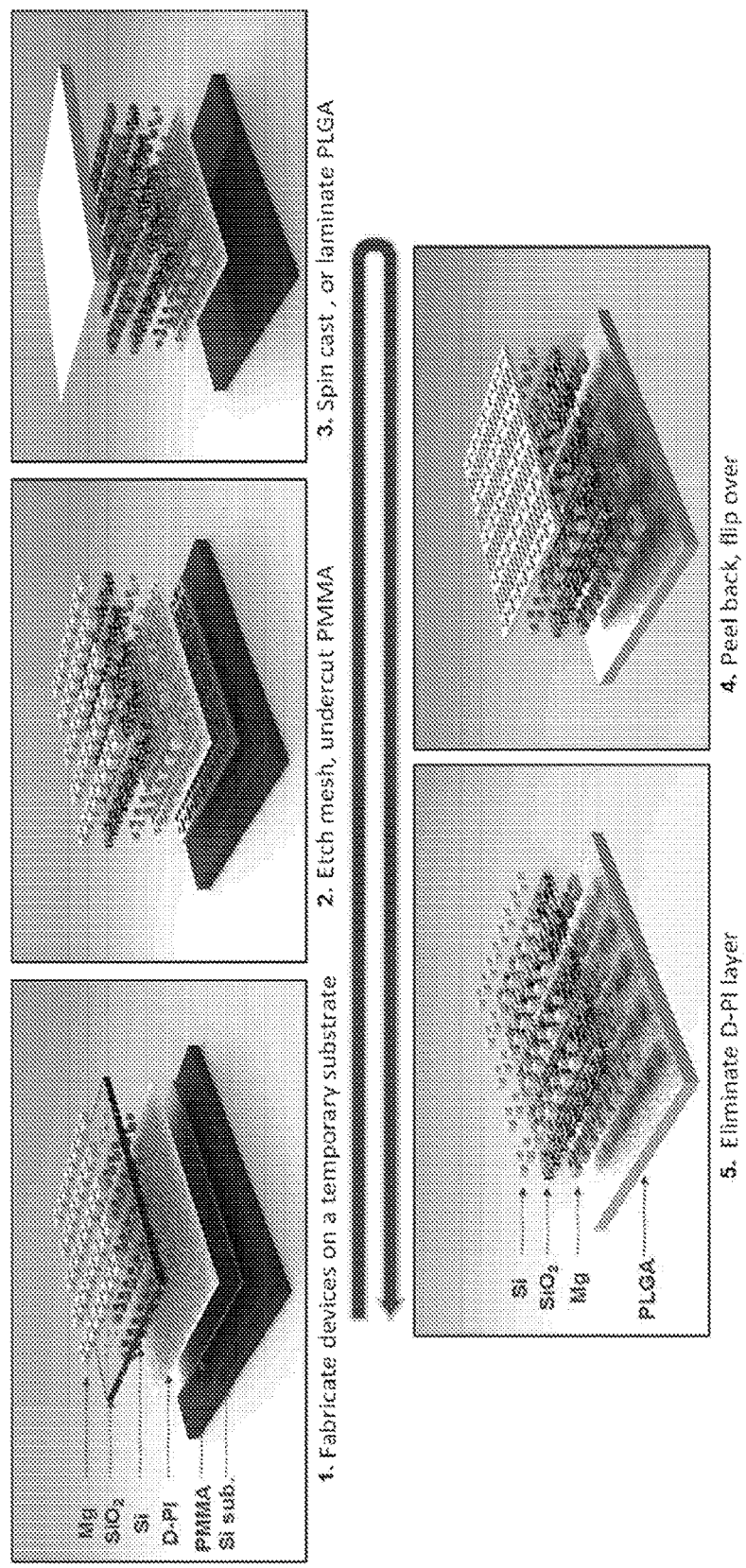

FIG. 20. Schematic illustration of a peel-and-stick lamination process for integrating transient electronics with transient substrates. This scheme decouples the substrate materials from device processing.

Figure 21:
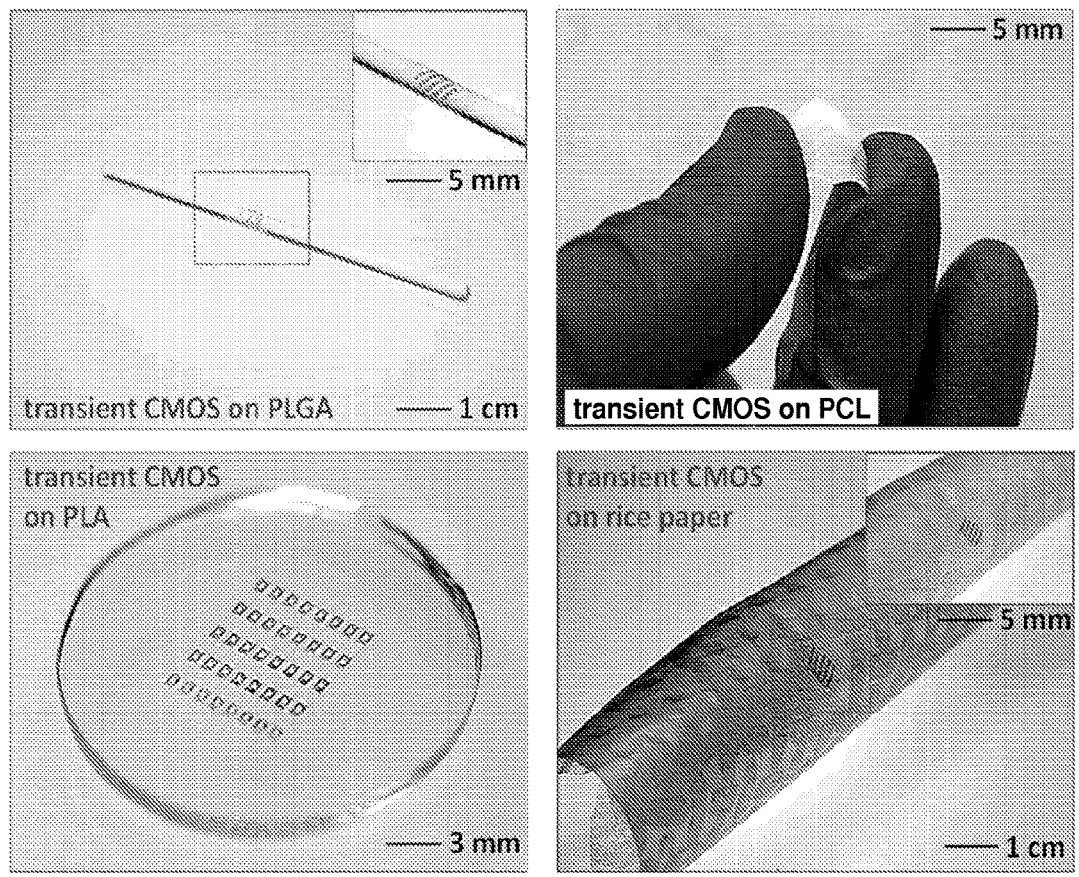

FIG. 21. Examples of the use of peel-and-stick lamination for integrating transient CMOS on a range of transient substrates: PLGA, PCL, PLA & rice paper. (a) Photograph of an array of transient CMOS inverters on a thin PLGA substrate wrapped onto a cylindrical glass rod, with a magnified image in the inset. (b) Image of a transient device on a PCL substrate, in a bent configuration. (c) An array of transient CMOS inverters on a PLA substrate. (d) Image of a transient circuit on rice paper. Here, a small amount of water creates a slightly tacky surface to facilitate transfer.

Figure 22:
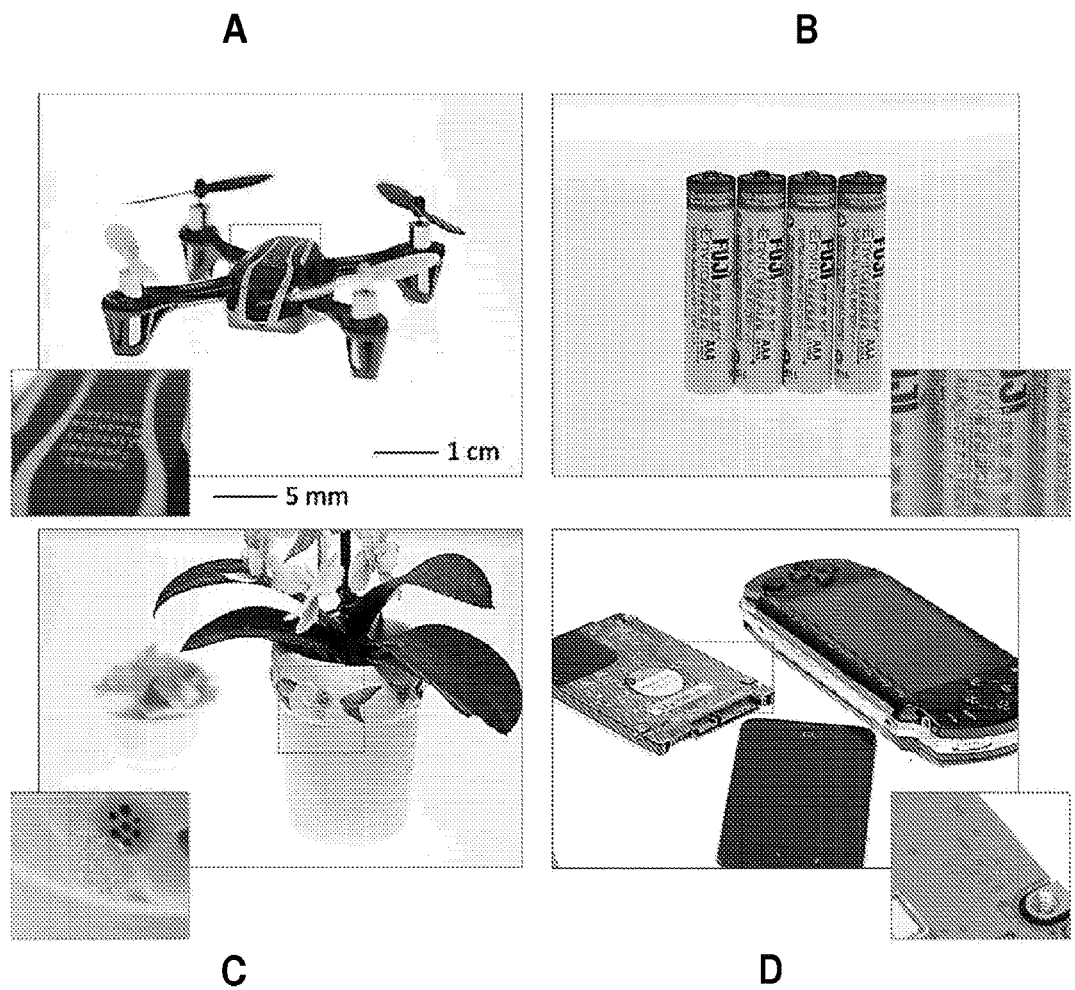

FIG. 22. Examples of integration of thin, transient CMOS 'appliques' onto a variety of surfaces. (a) Surveillance system (drone). (b) Green electronics (batteries). (c) Eco-friendly merchandise (plants). (d) Degradable electronic devices that minimize waste streams (portable devices).

Figure 23:
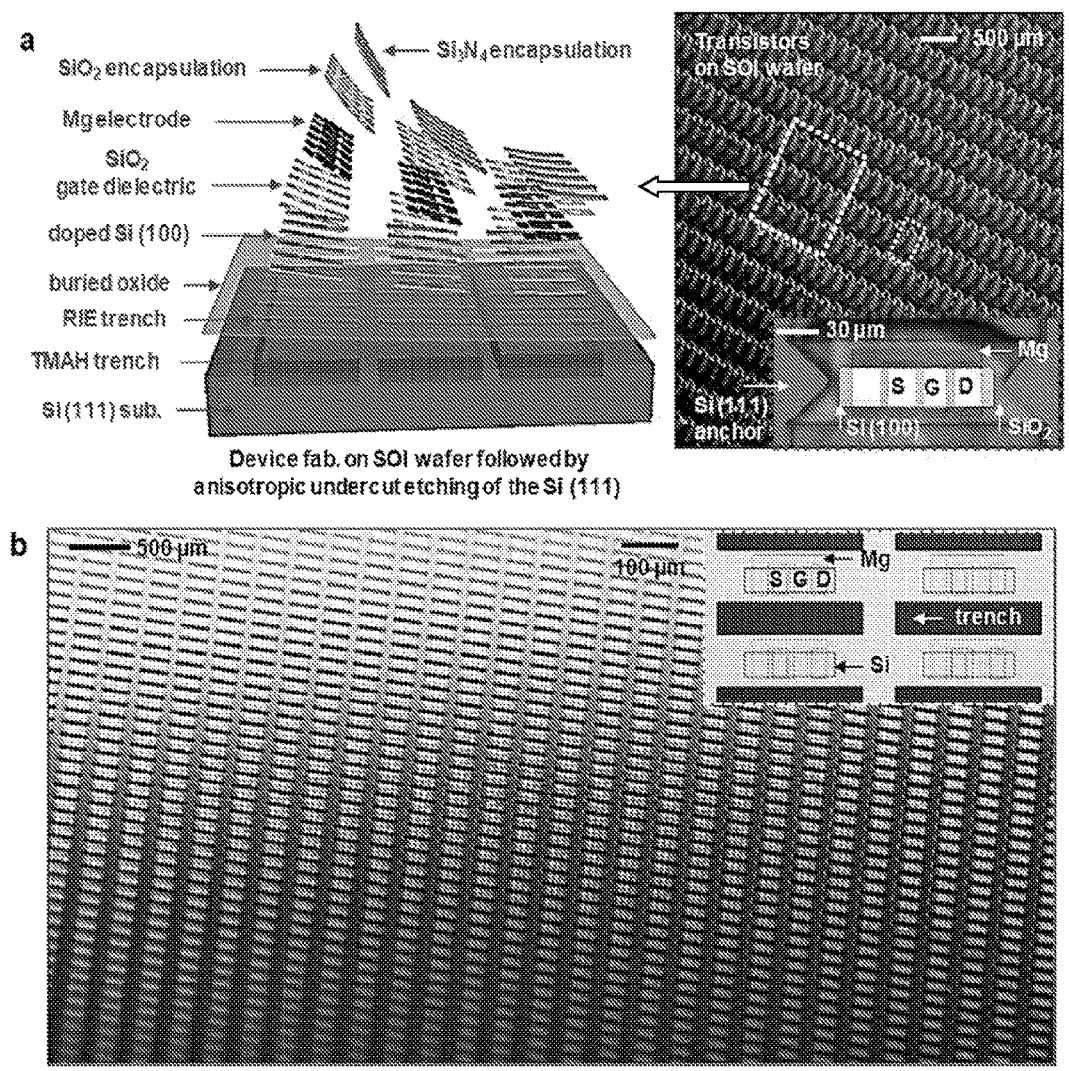

FIG. 23. (a) Schematic exploded view illustration (left) and optical microscope image (right) of devices after complete processing followed by anisotropic undercut etching of the surface region of the SOI (111) substrate with TMAH. The inset on the right shows a magnified view of an individual transistor in the array. The device uses magnesium (Mg; ~200 nm) for source, drain and gate electrodes, silicon dioxide ($SiO_2$) for the gate (~100 nm) and interlayer (~100 nm) dielectrics, and silicon (Si) for the semiconductor (~100 nm). (b) An optical image of a large area array of n-channel MOSFETs, with micrograph of representative devices in the inset.

Figure 24:
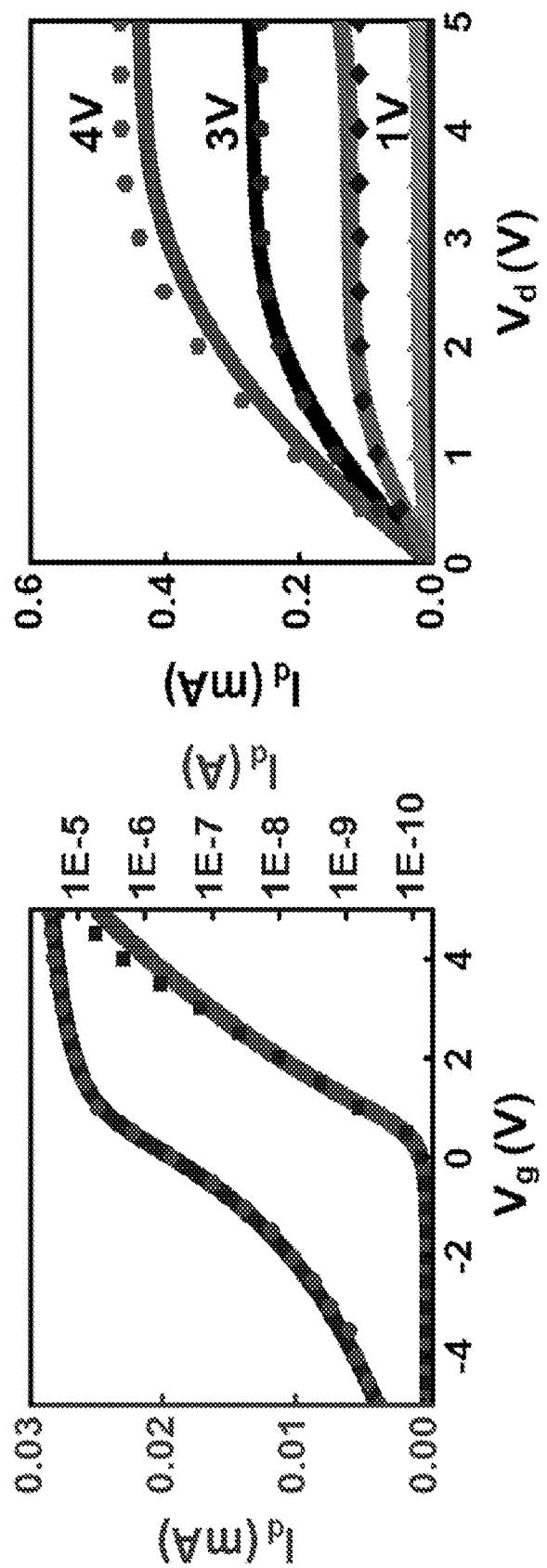

FIG. 24. Linear (blue) and log scale (red) transfer curves of an n-channel MOSFET (channel length and width (W) are 10 μm and 40 μm, respectively) derived from a SOI (111), after transfer printing to a transient substrate (silk). The mobility and on/off ratio are 650 cm$^2$/Vs and >10$^5$, respectively. d) Full I-V characteristics. Experiment (lines); simulation (dots).

Figure 25:
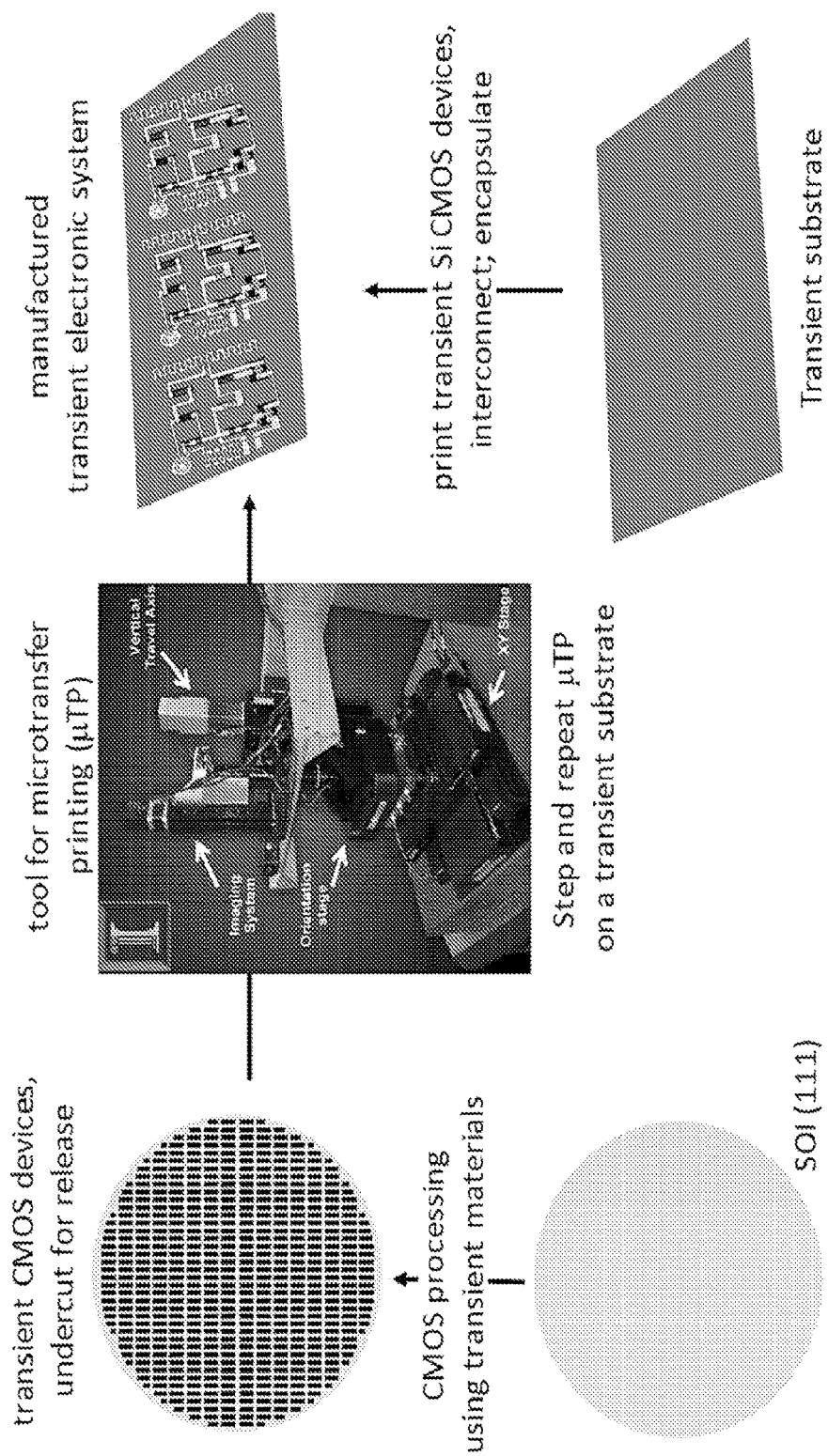

FIG. 25. Process flow for high volume manufacturing of transient electronic systems. Left: Foundry processing on a SOI (111) wafer yields CMOS devices and microdie that are released from the handle wafer by anisotropic etching of the Si (111). Each individual component remains tethered to the underlying wafer at its corners. Center: A high speed tool for transfer printing retrieves selected sets of these components and delivers them to a transient substrate. Right: These printed components are interconnected together and combined with sensors and passives using standard deposition and lithographic steps, compatible with back-end and/or large area fabrication tools. Encapsulating and packaging materials can be applied, as necessary, to complete the devices.

Figure 26:
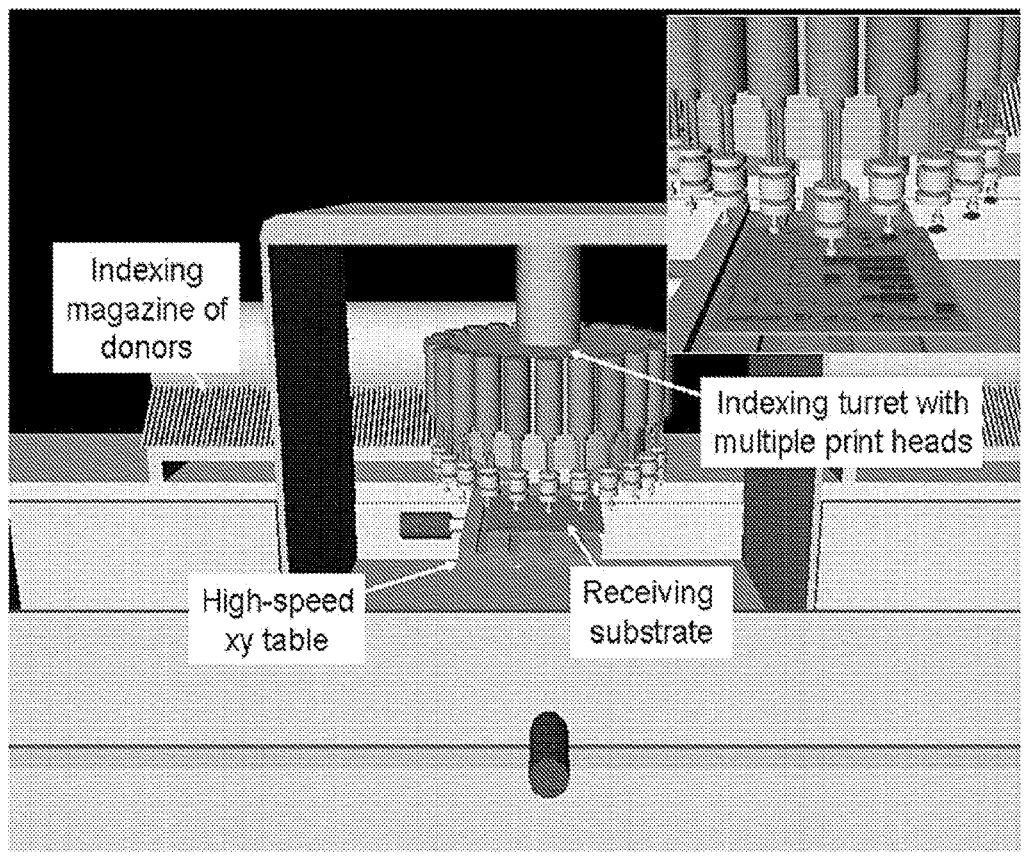

FIG. 26. Design of high speed tool for assembly of transient CMOS device components onto a transient substrate. The design builds on platforms for pick-and-place, adapted to enable microtransfer printing.

Figure 27:
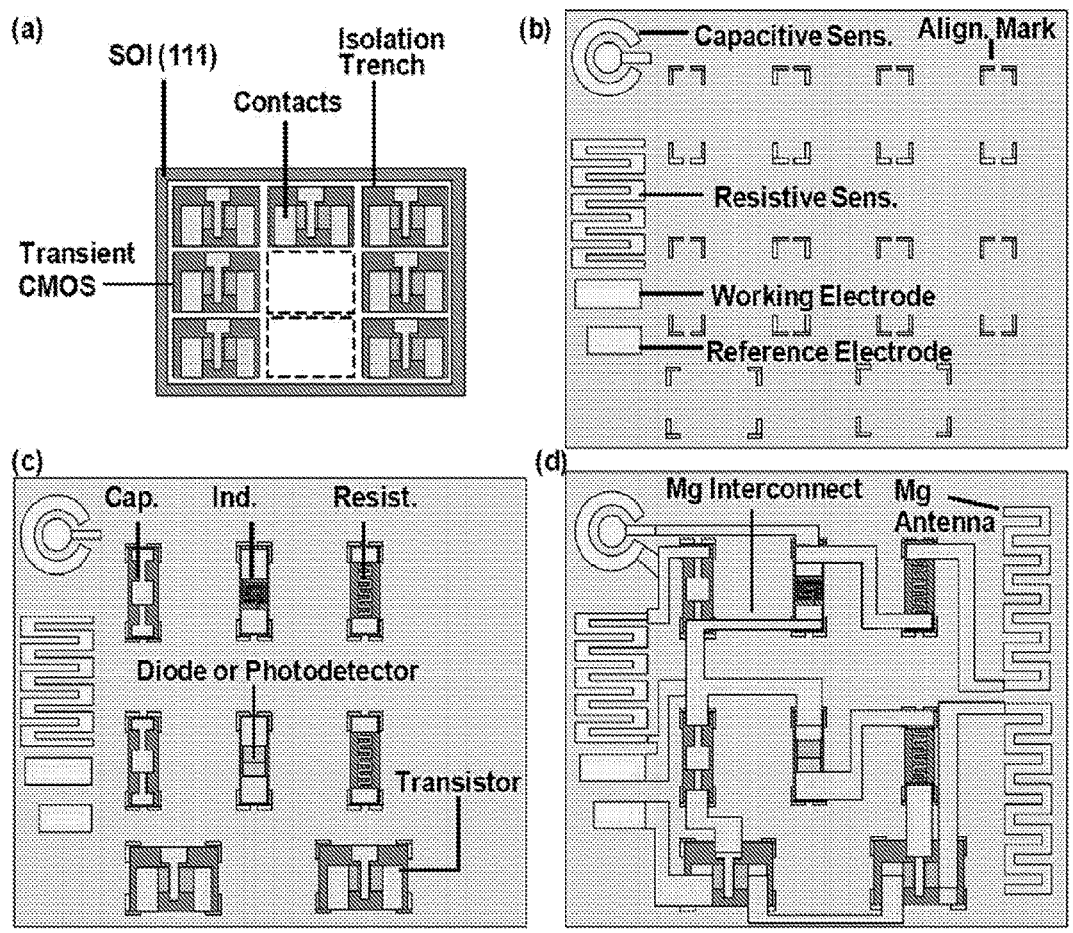

FIG. 27. Fabrication process and layouts for wireless sensor systems that use transient CMOS components transferred from an SOI (111) wafer. (a) Foundry CMOS components on an SOI (111) substrate, with metallization to facilitate interconnection; (b) Patterned alignment marks, sensors, and electrodes on a transient substrate; (c) Transient CMOS components transfer printed to regions defined by the alignment marks; (d) Deposition and patterning of metal for interconnection.

FIG. 28: (a) Process flow summary of one embodiment for making a transient electronic device. (b) Process flow summary providing additional detail of step 700.

Figure 28A:
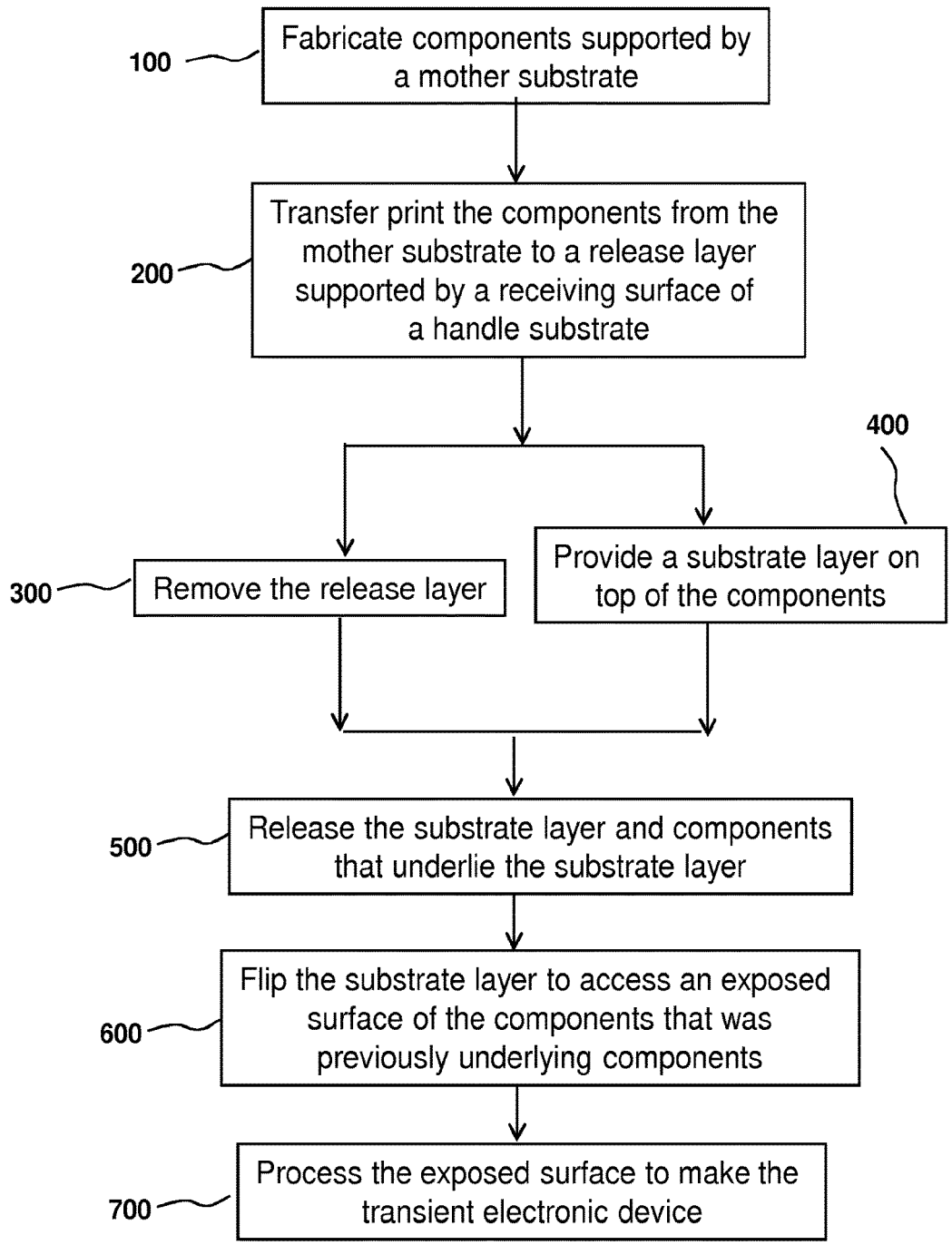
Figure 28B:
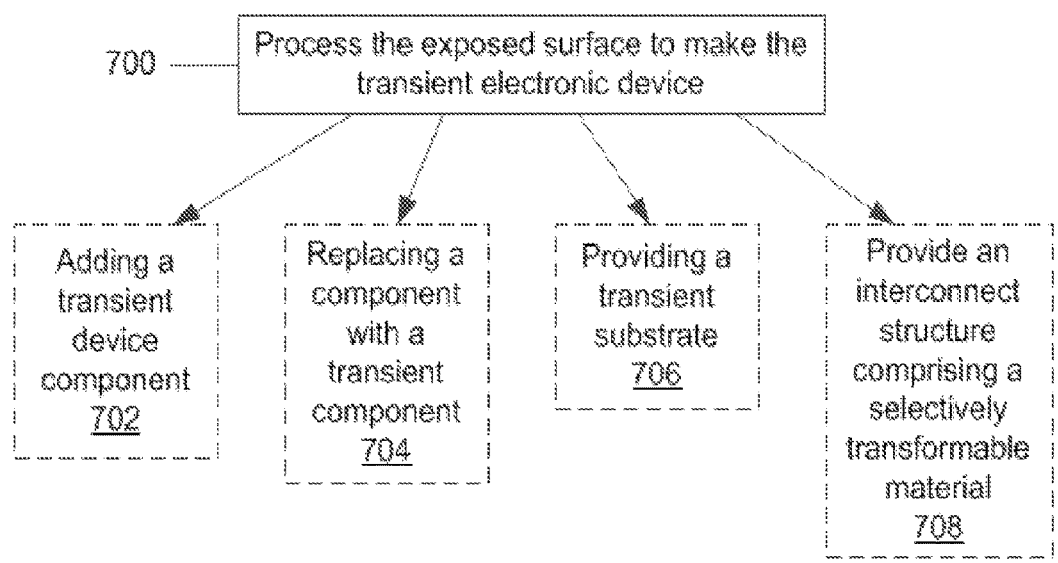
Figure 29:
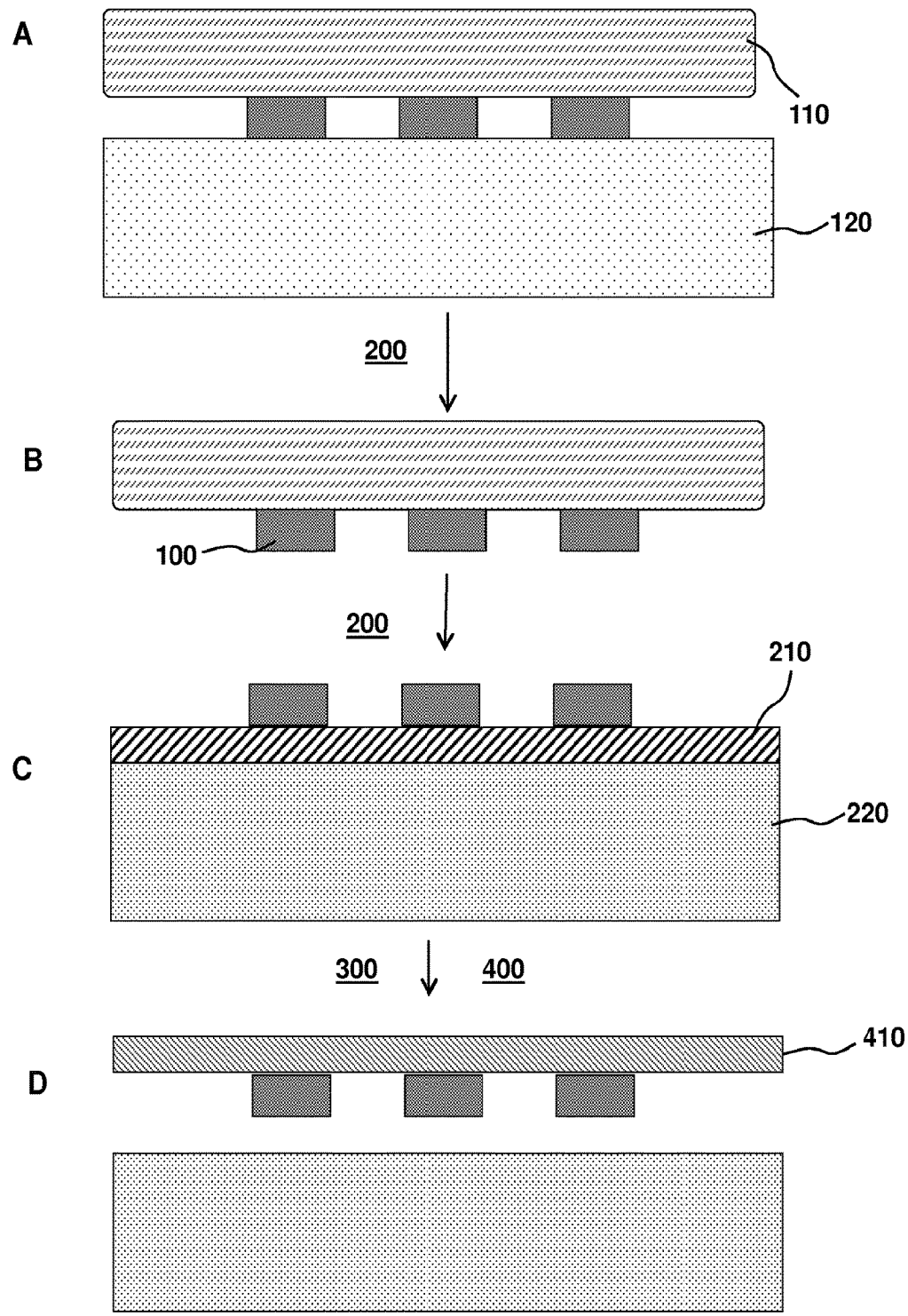
Figure 29:
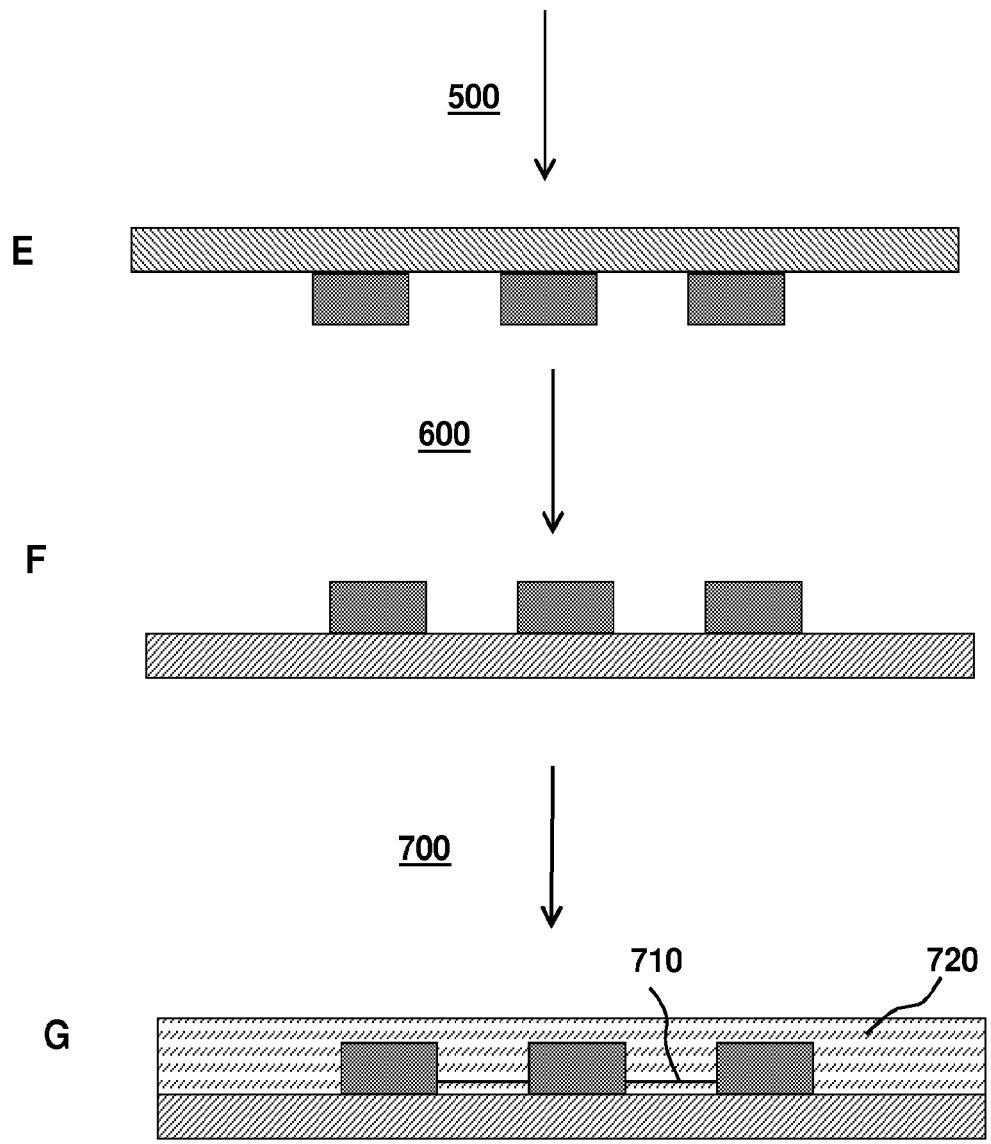

FIG. 29: Schematic illustration of the process outlined in FIG. 28.

Figure 30:
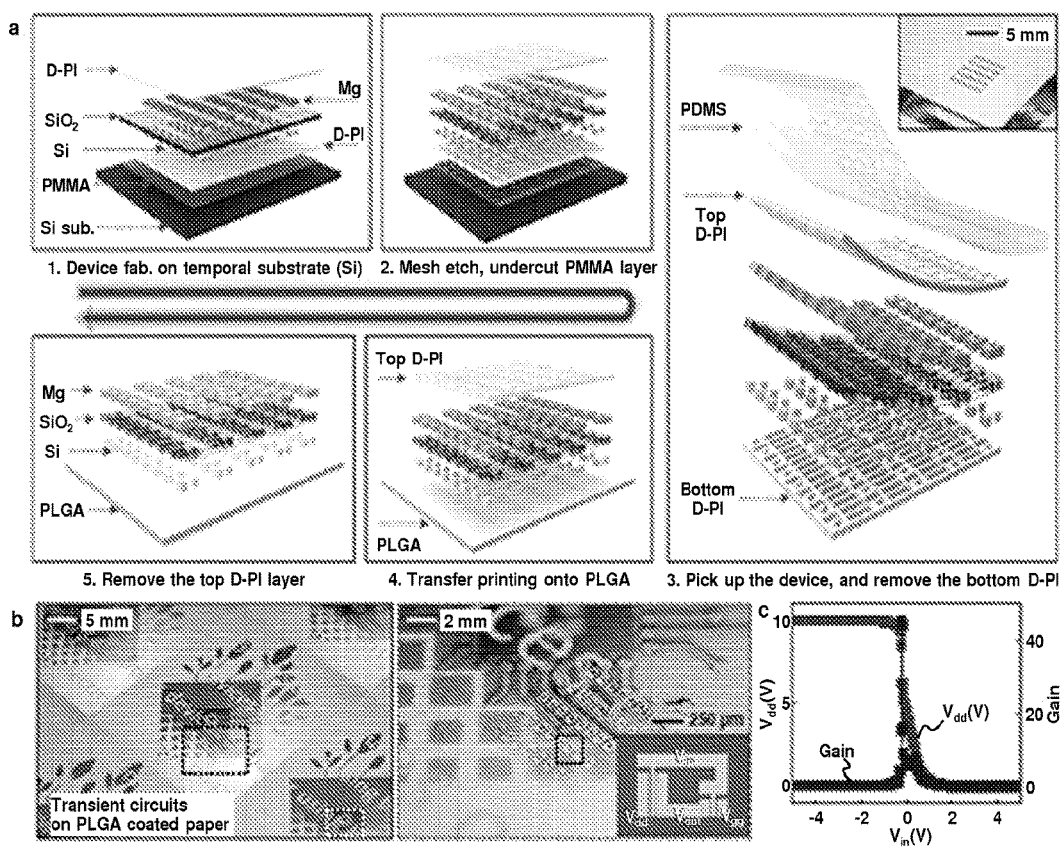

FIG. 30. Materials and procedures for fabricating transient electronic circuits on bioresorbable substrates. (a) Schematic illustrations of key processes for fabricating transient complementary metal-oxide-semiconductor (CMOS) on a carrier substrate (upper left). Defining a mesh type structure allows dissolution of the PMMA layer in boiling acetone at 90° C. to release the entire device (upper middle). Retrieving the released device onto a PDMS stamp (right, image of the device on PDMS in the inset), allows exposure and removal of the bottom layer of D-PI by reactive ion etching. Transfer printing onto a PLGA substrate (lower middle), and RIE etching of the top D-PI completes the process (lower left). (b) Images showing an array of transient CMOS inverters on a piece of paper coated with PLGA (left), with magnified view (right), and microscope image of an inverter in the inset. (c) Output voltage characteristics of a representative CMOS inverter with $V_{dd}$=10 V. The voltage gain is ~50.

Figure 31:
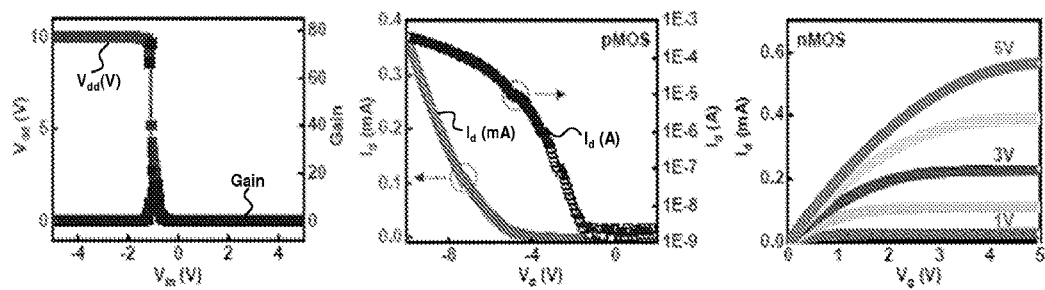

FIG. 31. Output voltage characteristics of a representative CMOS inverter at $V_{dd}$=10 V. The gain is ~80 (left). Linear (red) and log scale (blue) transfer curves of a typical transient p-channel MOSFET (middle). The channel length (L) and width (W) are 5 μm and 300 μm, respectively. The mobility (linear regime) and on/off ratio are ~70 cm$^2$/V·s and ~10$^5$, respectively. I-V characteristics of a typical n-channel MOSFET (right). The channel length (L) and width (W) are 15 μm and 100 μm, respectively. The mobility (linear regime) and on/off ratio are ~400 cm$^2$/V·s and ~10$^5$, respectively.

Figure 32:
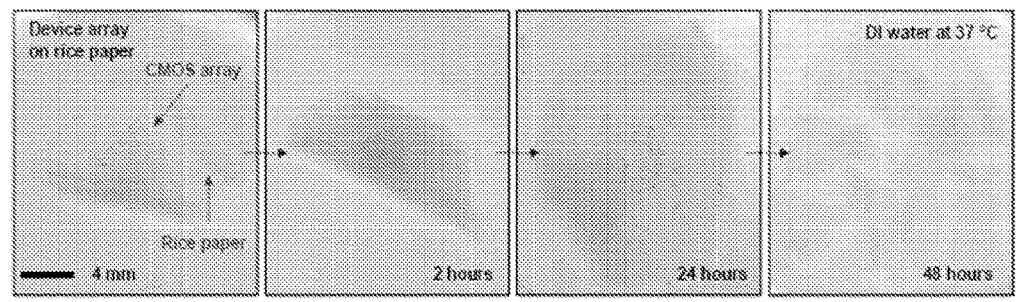

FIG. 32. Optical images at various stages of dissolution of an array of transient CMOS inverter on rice paper during immersion in DI water at physiological temperature (37° C.).

Figure 33:
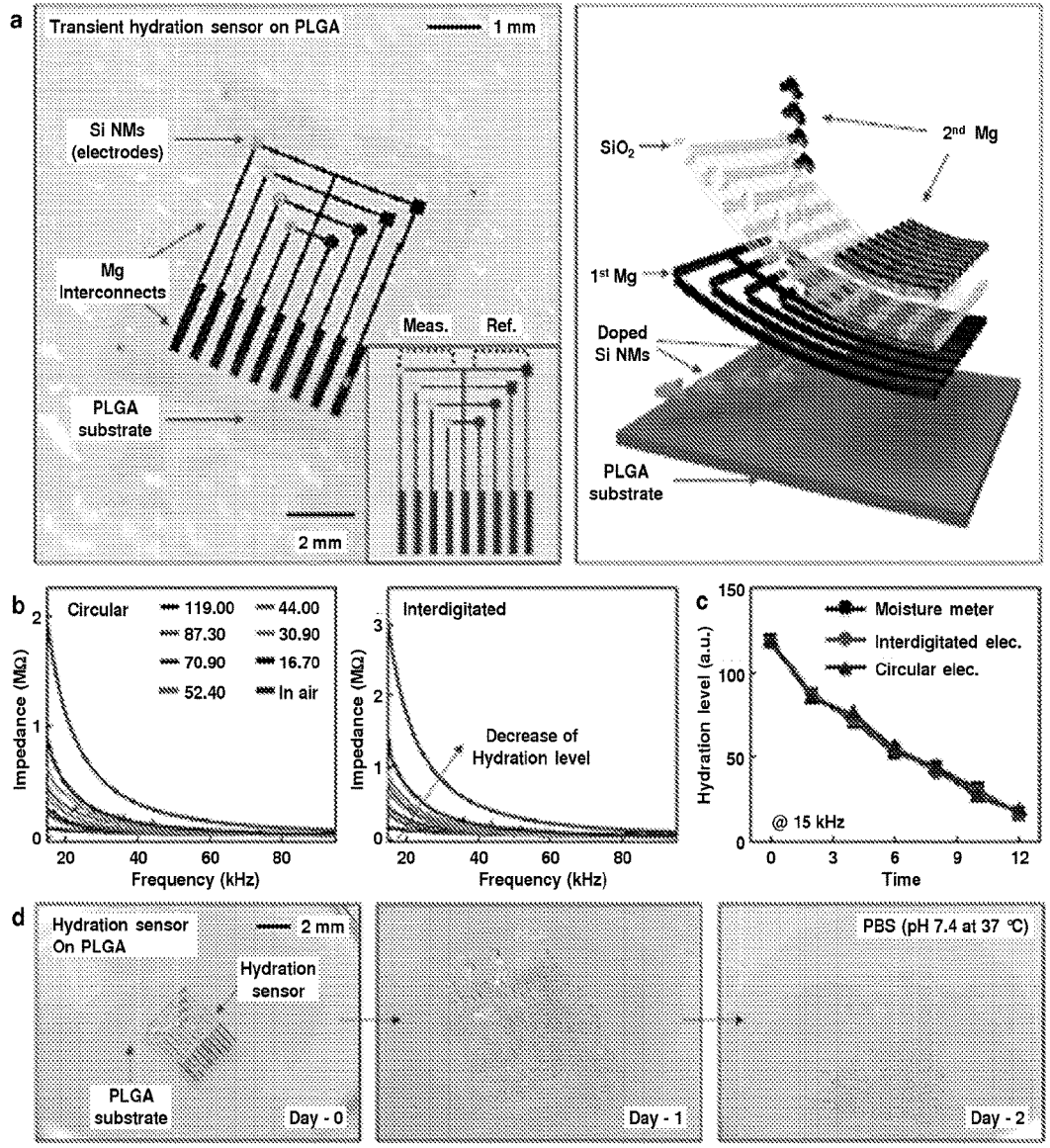

FIG. 33. A transient hydration sensor. (a) Image and exploded-view schematic illustration of a transient hydration sensor, comprised of doped Si NMs for electrodes, Mg for contacts and interconnects, PECVD $SiO_2$ as interlayer dielectrics and PLGA for the substrate. (b) Results from use of this type of device to measure changes in impedance as a function of frequency, with both circular (left) and interdigitated (right) electrodes. (c) Comparison of hydration levels measured using a commercial moisture meter (CMM, MoistureMeterSC Compact, Delfin Inc) and a transient hydration sensor (black, moisture meter; red, circular electrodes; blue, interdigitated electrodes). (d) Images of a transient hydration sensor on a PLGA film at various stages of dissolution during immersion in phosphate buffer solutions (PBS, 1 M, pH 7.4) at physiological temperature (37° C.) after 1 day and 2 days, respectively.

Figure 34:
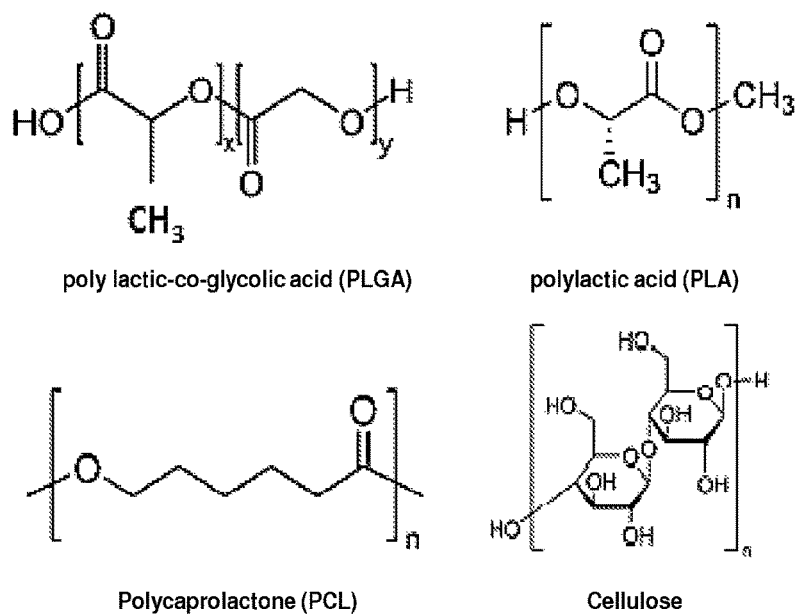

FIG. 34. The chemical structures of biodegradable polymers as substrate materials, poly lactic-co-glycolic acid (top left, PLGA), polylactic acid (top right, PLA), polycaprolactone (bottom left, PCL) and cellulose (bottom right).

Figure 35:
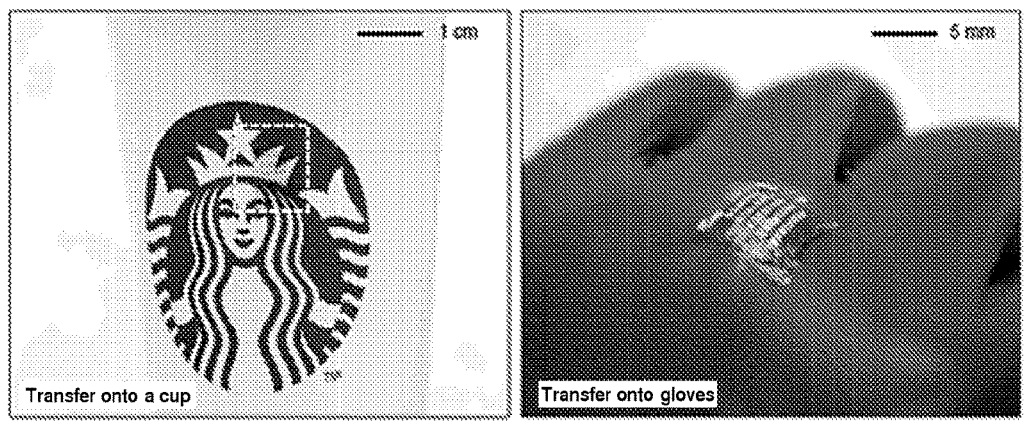

FIG. 35. Images of transient electronic systems transfer printed on a cup (left) and gloves (right).

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Electronic device" generally refers to a device incorporating a plurality of components, and includes large area electronics, printed wire boards, integrated circuits, component arrays, biological and/or chemical sensors, physical sensors (e.g., temperature, strain, etc.), nanoelectromechanical systems, microelectromechanical systems, photovoltaic devices, communication systems, medical devices, optical devices and electro-optic devices. As discussed further, an electronic device that is "transient" refers to at least one component of the device that degrades over time, thereby affecting device functionality. The transient nature of the device may include up to ensuring the device, after a predetermined amount of time, effectively dissipates, disappears (e.g., is broken up and absorbed or conveyed away passively) or from which no useful information can be obtained, including information that may otherwise be used to reverse engineer a comparable device that is not transient.

"Semiconductor" refers to any material that is an insulator at a very low temperature, but which has an appreciable electrical conductivity at a temperature of about 300 Kelvin. In the present description, use of the term semiconductor is intended to be consistent with use of this term in the art of microelectronics and electronic devices. Useful semiconductors include those comprising elemental semiconductors, such as silicon, germanium and diamond, and compound semiconductors, such as group IV compound semiconductors such as SiC and SiGe, group III-V semiconductors such as AlSb, AlAs, AlN, AlP, BN, BP, BAs, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe, and SnS, layer semiconductors such as $PbI_2$, $MoS_2$, and GaSe, oxide semiconductors such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, PbMnTe, $BaTiO_3$, $SrTiO_3$, $LiNbO_3$, $La_2CuO_4$, $La_{0.7}Ca_{0.3}MnO_3$, CdZnTe, CdMnTe, $CuInSe_2$, copper indium gallium selenide (CIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful for aspects described herein. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to, oxygen, carbon, and metals including heavy metals. Heavy metal impurities include, but are not limited to, the group of elements between copper and lead on the periodic table, calcium, sodium, and all ions, compounds and/or complexes thereof.

A "semiconductor component" broadly refers to any semiconductor material, composition or structure, and expressly includes high quality single crystalline and polycrystalline semiconductors, semiconductor materials fabricated via high temperature processing, doped semiconductor materials, inorganic semiconductors, and composite semiconductor materials.

A "component" is used broadly to refer to an individual part of a device. An "interconnect" is one example of a component, and refers to an electrically conducting structure capable of establishing an electrical connection with another component or between components. In particular, an interconnect may establish electrical contact between components that are separate. Depending on the desired device specifications, operation, and application, an interconnect is made from a suitable material. Suitable conductive materials include semiconductors and metallic conductors.

Other components include, but are not limited to, thin film transistors (TFTs), transistors, diodes, electrodes, integrated circuits, circuit elements, control elements, photovoltaic elements, photovoltaic elements (e.g. solar cell), sensors, light emitting elements, actuators, piezoelectric elements, receivers, transmitters, microprocessors, transducers, islands, bridges and combinations thereof. Components may be connected to other components such as one or more contact pads as known in the art, such as by metal evaporation, wire bonding, and application of solids or conductive pastes, for example. Electronic devices of the invention may comprise one or more components, optionally provided in an interconnected configuration. Any of the components may have a transient profile in that the component degrades over time with use or by a user initiated trigger signal.

A "user initiated trigger signal" includes any action, other than the mere placement of a transient device in a particular environment, by which a person may start or initiate a programmable transformation of a transient device. Exemplary "user initiated trigger signals" include providing real-time user input data to the device or a transmitter in communication with the device (e.g., pressing a button, flipping a switch, setting a timer, etc.), providing at least one non-ambient external source of energy directly or indirectly to the device (e.g., an electric field, a magnetic field, acoustic energy, pressure, strain, heat, light, mechanical energy, etc.), and/or programming software to execute computer-readable instructions, which may be based on data received from the device, for example data from a feedback loop. In an embodiment, the user initiated external trigger signal is an electronic signal, an optical signal, a thermal signal, a magnetic signal, a mechanical signal, a chemical signal, an acoustic signal or an electrochemical signal. In an embodiment, the invention provides a transient electronic device configured to receive a user initiated trigger signal, for example, a user initiated trigger signal provided by a transmitter and received by a receiver component of the device.

A "non-ambient external source of energy" includes energy having a magnitude at least 10% greater, or at least 25% greater, or at least 50% greater than the magnitude of ubiquitous energy of the same form found in the environment in which a transient device is located.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Island" refers to a relatively rigid component of an electronic device comprising a plurality of semiconductor components. "Bridge" refers to structures interconnecting two or more islands or one island to another component. Specific bridge structures include semiconductor and metallic interconnects. In an embodiment, a transient device of the invention comprises one or more semiconductor-containing island structures, such as transistors, electrical circuits or integrated circuits, electrically connected via one or more bridge structures comprising electrical interconnects.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50% or optionally 90%, of the external surfaces of the structure are surrounded by one or more other structures. "Completely encapsulated" refers to the orientation of one structure such that it is completely surrounded by one or more other structures.

The invention includes transient devices having partially or completely encapsulated inorganic semiconductor components, metallic conductor components and/or dielectric components, for example, via incorporation of a polymer encapsulant, such as biopolymer, silk, a silk composite, or an elastomer encapsulant.

"Barrier layer" refers to a component spatially separating two or more other components or spatially separating a component from a structure, material, fluid or environment external to the device. In one embodiment, a barrier layer encapsulates one or more components. In some embodiments, a barrier layer separates one or more components from an aqueous solution, a biological tissue or both. The invention includes devices having one or more barrier layers, for example, one or more barrier layers positioned at the interface of the device with an external environment.

A barrier layer(s), and optionally a sacrificial layer on a substrate, may be etched to produce a "mesh structure", where at least a portion of the barrier layer(s), and optionally the sacrificial layer on a substrate, is removed. For example a portion of the barrier layer(s) disposed approximately 10 nanometers or more from an inorganic semiconductor component or additional component is removed. Removal of at least a portion of the barrier layer(s), and optionally the sacrificial layer on the substrate, may produce (i) one or more holes within the barrier layer(s) and/or (ii) electrical components, which are physically joined by a barrier layer(s) at a proximal end and physically separated at a distal end. In one embodiment, a mesh structure may be disposed upon a contiguous substrate, which provides structural support for the device during deployment into an environment.

"Contiguous" refers to materials or layers that are touching or connected throughout in an unbroken sequence. In one embodiment, a contiguous layer of an implantable biomedical device has not been etched to remove a substantial portion (e.g., 10% or more) of the originally provided material or layer.

"Active circuit" and "active circuitry" refer to one or more components configured for performing a specific function. Useful active circuits include, but are not limited to, amplifier circuits, multiplexing circuits, current limiting circuits, integrated circuits, transistors and transistor arrays. The present invention includes devices wherein the one or more inorganic semiconductor components, one or more metallic conductor components and/or one or more dielectric components comprise an active circuit or plurality of active circuits.

"Substrate" refers to a material, layer or other structure having a surface, such as a receiving surface, that is capable of supporting one or more components or devices. A component that is "bonded" to the substrate refers to a component that is in physical contact with the substrate and unable to substantially move relative to the substrate surface to which it is bonded. Unbonded components or portions of a component, in contrast, are capable of substantial movement relative to the substrate and may be referred to herein as in physical contact with the substrate. In an embodiment, the invention provides devices wherein one or more inorganic semiconductor components, one or more metallic conductor components and/or one or more dielectric components are directly or indirectly bonded to the substrate, for example, via an adhesive or adhesion layer.

A "selectively transformable material" is a material that undergoes a physical change and/or a chemical change under pre-selected and/or predetermined conditions, such as conditions of time, pressure, temperature, chemical or biological composition, and/or electromagnetic radiation. Selectively transformable materials useful for some device applications undergo a physical transformation, such as a phase change including melting, sublimation, etc., optionally at a preselected time or at a preselected rate or in response to a preselected set of conditions or change in conditions. Selectively transformable materials useful for some device applications undergo a chemical transformation, such as decomposition, disintegration, dissolution, hydrolysis, resorption, bioresorption, photodecomposition, depolymerization, etching, or corrosion, optionally at a preselected time or at a preselected rate or in response to a preselected set of conditions or change in conditions. The pre-selected condition(s) may occur naturally, for example, provided by conditions of a device environment (e.g., ambient temperature, pressure, chemical or biological environment, natural electromagnetic radiation, etc.) or may occur via artificial condition(s) provided to, or within, a transient electronic device, such as a user or device initiated temperature, pressure, chemical or biological environment, electromagnetic radiation, magnetic conditions, mechanical strain, or electronic conditions. When the selectively transformable material of a transient electronic device is exposed to the condition(s) that initiate transformation of the material, the selectively transformable material may be substantially completely or completely transformed at a "pre-selected time" or a "pre-selected rate". Devices of the invention include selectively transformable materials that undergo a complete transformation, substantially complete transformation or an incomplete transformation. A selectively transformable material that is "substantially completely" transformed is 95% transformed, or 98% transformed, or 99% transformed, or 99.9% transformed, or 99.99% transformed, but not completely (i.e., 100%) transformed. In some embodiments, a selectively transformable material undergoes a chemical change resulting in a change in a physical, chemical, electronic or optoelectronic property, optionally at a pre-selected time or at a pre-selected rate. In an embodiment, for example, a selectively transformable material undergoes a chemical or physical change resulting in a change of a first composition characterized by a conducting or semiconducting material to a second composition characterized as an insulator. In some embodiments, a selectively transformable material is a selectively removable material.

A "selectively removable material" is a material that is physically and/or chemically removed under pre-selected or predetermined conditions such as conditions of time, pressure, temperature, chemical or biological composition, and/or electromagnetic radiation. In an embodiment, for example, a selectively removable material is removed via a process selected from the group consisting of decomposition, disintegration, dissolution, hydrolysis, resorption, bioresorption, photodecomposition, and depolymerization, optionally at a preselected time or at a preselected rate or in response to a preselected set of conditions or change in conditions. In an embodiment, for example, a selectively removable material is removed by undergoing a phase change, such as melting or sublimation, resulting in loss or relocation of the material, optionally at a preselected time or at a preselected rate or in response to a preselected set of conditions or change in conditions. The pre-selected condition(s) may occur naturally, for example, provided by conditions of a device environment (e.g., ambient temperature, pressure, chemical or biological environment, natural electromagnetic radiation, etc.) or may occur via artificial condition(s) provided to, or within, a transient electronic device, such as a user or device initiated temperature, pressure, chemical or biological environment, electromagnetic radiation, or electronic conditions. When the selectively removable material of a transient electronic device is exposed to the condition(s) that initiate removal of the material, the selectively removable material may be substantially completely, completely removed or incompletely removed at a "pre-selected time" or a "pre-selected rate". A selectively removable material that is "substantially completely" removed is 95% removed, or 98% removed, or 99% removed, or 99.9% removed, or 99.99% removed, but not completely (i.e., 100%) removed.

A "pre-selected time" refers to an elapsed time from an initial time, $t_0$. For example, a pre-selected time may refer to an elapsed time from a component/device fabrication or deployment, to a critical time, $t_c$, for example, when the thickness of a selectively removable material exposed to a pre-selected condition(s) reaches zero, or substantially zero (10% or less of initial thickness, 5% or less of initial thickness, 1% or less of initial thickness) or when a property (e.g. conductance or resistivity) of a selectively removable material reaches a threshold value; e.g., a decrease in conductivity equal to 50%, optionally for some applications 80%, and optionally for some applications 95% or alternatively when conductivity equals 0. In an embodiment, the preselected time may be calculated according to:

$$t_c = \frac{4\rho_m M(H_2O)}{kw_0 M(m)} \frac{\sqrt{\frac{kh_0^2}{D}}}{\tanh\sqrt{\frac{kh_0^2}{D}}} \quad (1)$$

where $t_c$ is the critical time, $\rho_m$ is the mass density of the material, $M(H_2O)$ is the molar mass of water, $M(m)$ is the molar mass of the material, $h_0$ is the initial thickness of the material, D is the diffusivity of water, k is the reaction constant for the dissolution reaction, and $w_0$ is the initial concentration of water.

A "pre-selected rate" refers to an amount of selectively removable material removed from a device or component per unit time. The pre-selected rate may be reported as an average rate (over the lifetime of the device or component) or an instantaneous rate. When a rate type is not specified, an average rate is assumed. The rate may be determined directly by the amount of material removed, or may be functionally determined via the magnitude of decrease in device functionality (e.g., resistance, current, electric potential, output, etc.).

A "programmable transformation" refers to a pre-selected or predetermined physical, chemical and/or electrical change within a transient electronic device that provides a change of the function of the device from a first condition to a second condition. A programmable transformation may be pre-set at the time of component/device fabrication or deployment or a real-time triggered programmable transformation controlled by a transmitter that provides a signal received by the device.

A "transience profile" describes a change in physical parameters or properties (e.g., thickness, conductivity, resistance, mass, porosity, etc.) of a material as a function of time, e.g., thickness gained/lost over time. A transience profile may be characterized by a rate, for example, the rate of change of the physical dimensions (e.g., thickness) or physical properties (e.g., mass, conductivity, porosity, resistance, etc.) of a selectively transformable material. The invention includes selectively transformable materials having a transience profile characterized by a rate of change of the physical dimensions (e.g., thickness) or physical properties (e.g., mass, conductivity, etc.) that is constant or varies as a function of time. The transience profile may be a composite profile, in that it comprises at least two distinct and different profiles, such as a first transience profile where the material is protected by another material (e.g., a component that is encapsulated or otherwise inaccessible) so that the rate of change may be close to zero, but that over time becomes exposed based on the encapsulating layer that is selectively transformable or removable, thereby increasing a rate of change.

"Degradable" refers to material that is susceptible to being chemically and/or physically broken down into smaller segments. Degradable materials may, for example, be decomposed, resorbed, dissolved, absorbed, corroded, de-polymerized and/or disintegrated. In some embodiments, the invention provides degradable devices.

"Flipping" refers to an action wherein opposed surfaces are changed, such as a bottom surface that after flipping is a top surface and a top surface that after flipping is the bottom surface. "Flipping" is used broadly to refer to the functional equivalent of exposing a previously inaccessible surface as well as making relatively inaccessible a previously exposed surface. In the context of the instant invention, a substrate is introduced to a top surface of the components, thereby making that top surface relatively inaccessible or relatively more inaccessible for embodiments where an intervening layer is between the substrate layer and the components. In contrast, the substrate may be used to remove the components from the handle wafer, thereby exposing the previously relatively inaccessible bottom surface. In an aspect, the flipping refers to an embodiment where a force is provided to change the orientation of the bottom surface to that of a top surface to be ready for processing.

"Processing" is used broadly to refer to treatment of a device or surface to obtain one or more desired functional attributes, including a transience profile and/or a functional attribute such as electrical interconnection and parameter sensing. Examples of processing include providing a material such as by deposition of one or more components, including active electronic components, structural, barrier, or encapsulating layer(s), removal or partial removal of materials, or transformation or partial transformation of materials to obtain a desired physical parameter.

"Foundry" refers to a plant that produces semiconductors, and typically requires expensive devices and process implementation to provide high-quality semiconductor material, including highly controlled environmental control and clean rooms. Embodiments of the invention using foundry processing are beneficial for accessing high quality semiconductor and dielectric materials, such as single crystalline silicon and $SiO_2$, in useful device formats and layouts. In some embodiments, for example, methods of the invention include a hybrid process involving some processing steps carried out in a foundry (e.g., fabrication of high quality single crystalline silicon and $SiO_2$ device elements in a specific device design) and other processing steps carried out using non-foundry techniques, such as solution phase processing or transfer printing. This hybrid approach leverages access to the high quality materials produced via foundry based techniques with flexibility for integration of a range of selectively transformable materials allowed by non-foundry techniques.

"Fidelity" refers to a measure of how well a selected pattern of components, such as a plurality of semiconductor and/or metallic components, is transferred to a receiving surface of a substrate, such as a handle wafer or a final substrate of the electronic device. High fidelity refers to transfer of a selected pattern of elements wherein the relative positions and orientations of individual elements are preserved during transfer, for example wherein spatial deviations of individual elements from their positions in the selected pattern are less than or equal to 500 nanometers, more preferably less than or equal to 100 nanometers. "High throughput" refers to the number of µ-die transfers per hour, such as throughputs of 10,000 µ-die/h, or about 100,000 µ-die/h, including a range selected from between about 100 µ-die/h and about 500,000,000 µ-die/h. Alternatively, high-throughput refers to the number of components transfer-printed in a single transfer print, such as above about 50, 100 or 1000 , such as between about 100 and 10,000 . In an aspect, the transfer print process is described as having a transfer print yield that is better than 75%, better than 90%, or better than 95% transfer of components to the other substrate.

"Nanostructured" and "microstructured" refer to components having one or more nanometer-sized and micrometer-sized, respectively, physical dimensions (e.g., thickness) or features such as recessed or relief features, such as one or more nanometer-sized and micrometer-sized channels, voids, pores, pillars, etc. The relief features or recessed features of a nanostructured material have at least one physical dimension selected from the range of 1-1000 nm, while the relief features or recessed features of a microstructured material have at least one physical dimension selected from the range of 1-1000 µm. Nanostructured and microstructured components include, for example, thin films (e.g., microfilms and nanofilms), porous materials, patterns of recessed features, patterns of relief features, materials having abrasive or rough surfaces, and the like. A nanofilm structure is also an example of a nanostructured material and a microfilm structure is an example of a microstructured material. In an embodiment, the invention provides devices comprising one or more nanostructured or microstructured inorganic semiconductor components, one or more nanostructured or microstructured metallic conductor components, one or more nanostructured or microstructured dielectric components, one or more nanostructured or microstructured encapsulating layers and/or one or more nanostructured or microstructured substrate layers.

A "nanomembrane" is a structure having a thickness selected from the range of 1-1000 nm or alternatively for some applications a thickness selected from the range of 1-100 nm, for example provided in the form of a ribbon, cylinder or platelet. In some embodiments, a nanoribbon is a semiconductor, dielectric or metallic conductor structure of an electronic device. In some embodiments, a nanoribbon has a thickness less than 1000 nm and optionally less than 100 nm. In some embodiments, a nanoribbon has a ratio of thickness to a lateral dimension (e.g., length or width) selected from the range of 0.1 to 0.0001.

"Dielectric" refers to a non-conducting or insulating material. In an embodiment, an inorganic dielectric comprises a dielectric material substantially free of carbon. Specific examples of inorganic dielectric materials include, but are not limited to, silicon nitride, silicon dioxide, silk, silk composite, elastomers and polymers.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomeric stamp" and "elastomeric transfer device" are used interchangeably and refer to an elastomeric material having a surface that can receive as well as transfer a material. Exemplary conformal transfer devices useful in some methods of the invention include elastomeric transfer devices such as elastomeric stamps, molds and masks. The transfer device affects and/or facilitates material transfer from a donor material to a receiver material. In an embodiment, a method of the invention uses a conformal transfer device, such as an elastomeric transfer device (e.g. elastomeric stamp) in a microtransfer printing process, for example, to transfer one or more single crystalline inorganic semiconductor structures, one or more dielectric structures and/or one or more metallic conductor structures from a fabrication substrate to a device substrate. Stamp is used broadly herein to refer to a substrate that can pick up components from one surface and transfer them to another surface. Accordingly, in an aspect the stamp may be a material having an adhesive surface that facilitates pick-up by adhesive forces, wherein the adhesive forces are less than subsequent contact forces when the stamp is brought into contact with a receiving surface. In an embodiment, the transfer printing may be direct surface-to-surface contact, from donor to a receiving surface.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of a tissue in a biological environment.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In an embodiment, a method of the invention comprises establishing conformal contact between a conformal transfer device and one or more single crystalline inorganic semiconductor structures, one or more dielectric structures and/or one or more metallic conductor structures, for example, in a microtransfer printing process, such as dry transfer contact printing. The receiving surface may functionally correspond to a release layer that is later used to release the components from a substrate that supports the release layer.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (2)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (3)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components, such as substrate, encapsulating layer, inorganic semiconductor structures, dielectric structures and/or metallic conductor structures, having a low Young's modulus. In an embodiment, a device of the invention has an overall low Young's modulus.

"Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire material.

"Low modulus" refers to materials having a Young's modulus less than or equal to 10 MPa, less than or equal to 5 MPa or less than or equal to 1 MPa.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

Transient devices and methods of making and using the devices will now be described with reference to the figures. For clarity, multiple items within a figure may not be labeled and the figures may not be drawn to scale.

EXAMPLE 1

Materials and Processes for High Performance Transient, Bioresorbable Electronics We describe materials and fabrication procedures that allow bioresorbable transistors and simple integrated circuits, in which the key device processing steps occur on silicon wafer substrates, in schemes compatible with established methods used in conventional microelectronics. The approach relies on an unusual type of silicon on insulator wafer, and yields devices that use ultrathin sheets of monocrystalline silicon for the semiconductor, thin films of magnesium for the electrodes and interconnects, silicon dioxide and magnesium oxide for the dielectrics and silk for the substrates. A range of component examples, with detailed measurements of their electrical characteristics and dissolution properties, illustrate the capabilities. In vivo toxicity tests demonstrate biocompatibility in sub-dermal implants. The results have significance for broad classes of water-soluble, 'transient' electronic devices.

Implantable biomedical components serve critically important roles in modern clinical medicine. Such devices can be classified into two types: those that exist for long periods of time, typically designed to be permanent; and those that disappear, or resorb, in the body after they provide some useful function. The former includes both simple, passive devices such as artificial joints and pins,[1] as well as sophisticated electronic components such as deep brain electrical stimulators,[2] cardiac pacemakers[3] and programmable drug delivery systems.[4] The latter, by contrast, is currently available only in the form of passive elements such as resorbable sutures[5, 6] or matrices for drug release[7, 8], degradable intravascular stents[9, 10] and resorbable plate-screw systems.[11] An unaddressed technology opportunity, then, exists in biodegradable devices that are capable of active electronic processing, sensing, communication and/or actuation within or on the surface of the body. Envisioned uses range from non-antibiotic appliques designed to reduce the incidence of surgical site infections, to electrical stimulators that can accelerate bone growth, to systems that can release drugs at programmed intervals. In each case, the devices operate only over some finite period of time, typically defined by a healing process; afterward, they resorb to eliminate unnecessary device load in a way that avoids surgical intervention.

Initial, early technical work toward this type of technology yielded two examples of partially resorbable devices, in the sense that certain, but not all, of the component materials resorb. One involves ultrathin electrodes and/or transistors built on films of silk fibroin, engineered to facilitate conformal contact with biological tissues, as demonstrated in electrocorticography,[12] and to disperse thin, miniaturized electronic components in ways that minimize adverse body responses, as demonstrated in sub-dermal implants.[13] The other uses organic or bio-organic semiconductors with polymer dielectrics/substrates to yield systems in which all components except for the electrodes and interconnects dissolve in bio-fluids, in a potentially biocompatible manner. [14, 15] Although the modest properties of known organic electronic materials limit the performance that can be achieved, this approach has some potential for devices that require only simple functions. A recent report describes materials and schemes that bypass constraints associated with these two previous directions.[16] The result is a fully resorbable, high performance class of electronics, where ultrathin sheets of semiconductor-grade monocrystalline silicon (i.e. silicon nanomembranes, or Si-NMs) serve as the active materials, inorganic dielectrics (e.g. MgO, $SiO_2$) and conventional metals (e.g. Mg) provide the other electronic functions, and silk forms the substrate and encapsulation layers. Enabled devices encompass nearly all of the key building blocks for integrated circuits, ranging from metal oxide field effect transistors (MOSFETs) to pn junction diodes, resistors, inductors, capacitors. Additional demonstrated components include solar cells, photodetectors, strain and temperature gauges, inductive power delivery systems and others. Although initially conceived for bioresorbable devices and demonstrated in programmable non-antibiotic bacteriocidal appliqués, this same technology can be more generally considered as a physically transient form of electronics, capable of disappearing via controlled physical or chemical change with well-defined rates. Non-biological applications include environmental sensors that avoid the need for recovery and collection after use, and consumer devices that minimize costly and hazardous disposal procedures.

A disadvantage of the original embodiment of this class of transient electronics is that many of the fabrication steps were performed on a transient substrate (e.g. silk), thereby constraining significantly the processing temperatures, choices of solvents and other aspects of the processing. These limitations prevent the use of manufacturing techniques that are found in high volume, low cost production of commercial silicon integrated circuits. The work described here establishes a silicon wafer-based strategy to fully formed transient circuit components and circuits, in configurations that allow their subsequent, and separate, integration with transient substrates and packaging materials. The results are important because they have the potential to enable realistic manufacturing strategies for transient electronics, in which only modest modifications to microelectronic fabrication facilities are needed. The concepts rely on the combined use of a specialized type of silicon on insulator (SOI) wafer and the techniques of transfer printing. The resulting devices involve constituent materials that all have some solubility in water: silicon, silicon dioxide, magnesium oxide, magnesium and silk. The following describes the concepts and demonstrates their use in fabrication of various electronic components and simple logic gates, with studies of their transient behaviors both through in vitro investigations of the kinetics and in vivo evaluations of biocompatibility and resorption.

Figure 1:
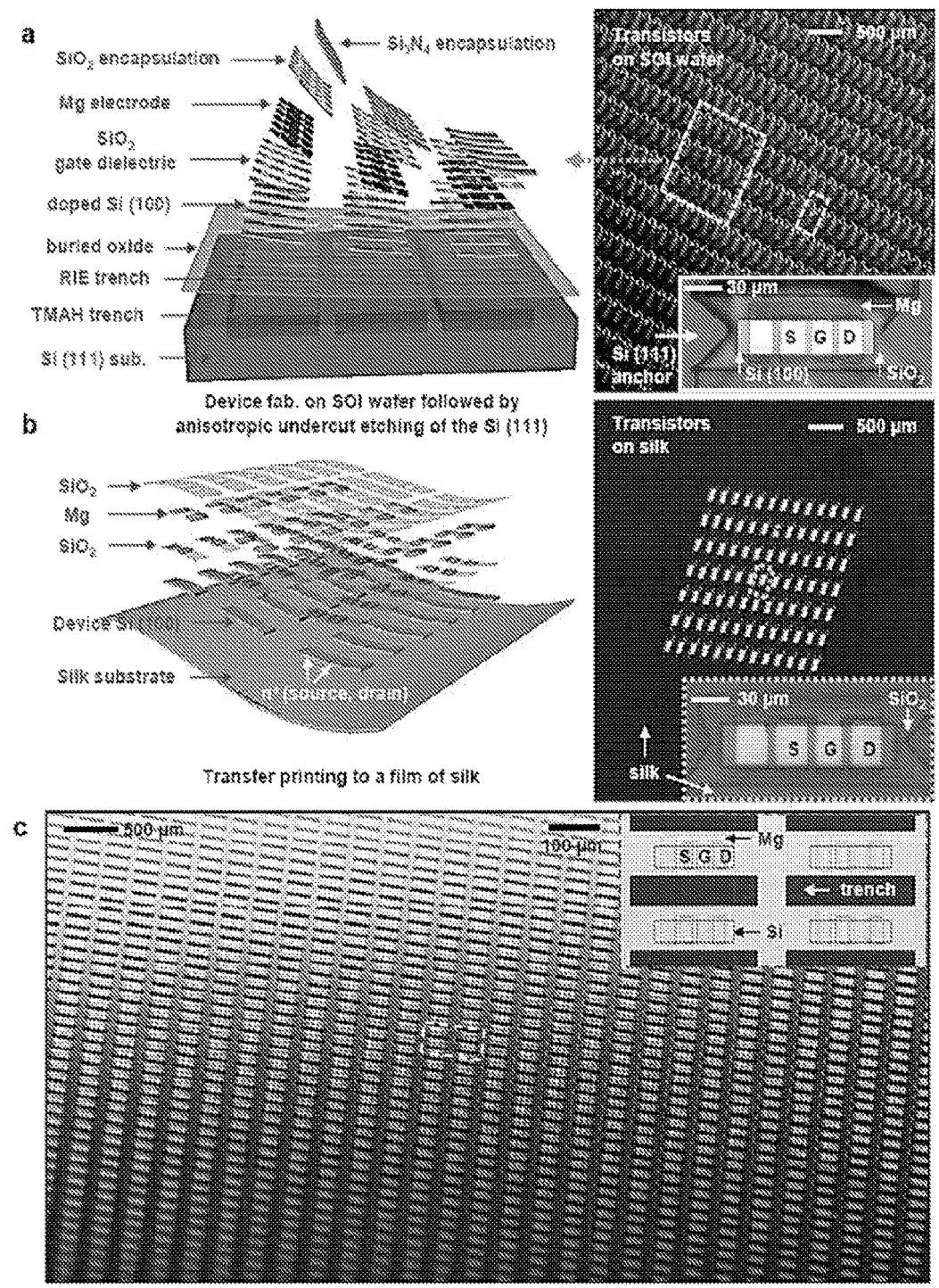
FIG. 1. Wafer-scale fabrication of fully formed transient transistors on specialized SOI substrates and their subsequent transfer printing to films of silk. a) Schematic exploded view illustration and optical microscope images of devices after complete processing followed by anisotropic undercut etching of the surface region of the SOI wafer substrate with TMAH. The inset shows a magnified view of an individual transistor in the array. b) Schematic illustration and image of these same devices after transfer printing to a film of silk. The inset shows a magnified view of an individual transistor. The device uses magnesium (Mg; ~200 nm) for source, drain and gate electrodes, silicon dioxide ($SiO_2$) for the gate (~100 nm) and interlayer (~100 nm) dielectrics, silicon (Si) for the semiconductor (~100 nm) and silk for the substrate (~25 µm). c) An optical image of a large area of n-channel MOSFETs, with micrograph of a representative device in the inset.

The overall scheme involves complete fabrication of circuits and/or circuit components in transient materials on a silicon wafer, followed by their controlled release and subsequent integration onto a transient substrate via transfer printing. FIG. 1 presents exploded-view schematic illustrations and optical micrographs of a representative system composed of a large-scale array of transient n-channel monocrystalline silicon metal-oxide field-effect transistors (MOSFETs), undercut etched from a SOI (111) wafer on which they were formed (FIG. 1a) and after their transfer to a thin sheet of silk as a substrate (FIG. 1b). The SOI wafer consists of ultrathin top layer of Si (p-type, ~100 nm) with (100) orientation for the active regions of the devices, a buried oxide layer (~1 μm) and supporting wafer with (111) orientation. The orientation of the wafer plays a critical role in the release of devices from its surface, as described in the following. Fabrication begins with high temperature, patterned doping (phosphorous at ~950° C.) of the top Si to define the channel regions and contacts for the MOSFETs. Patterned etching of the silicon creates isolated regions for each of the devices. A coating of $SiO_2$ (~100 nm) deposited by plasma-enhanced chemical-vapor deposition (PECVD) at 250° C. forms the gate dielectric. Etching in buffered oxide etchant (BOE, 6:1 , Transene company, USA) creates windows for source and drain contacts. Depositing Mg (~200 nm) by electron beam evaporation yields source, drain and gate electrodes aligned to the contacts and channel areas (FIG. 7a). Sequential PECVD steps define encapsulation layers of $SiO_2$ (~100 nm thick; patterned to expose the source, drain, and gate contacts) and $Si_3N_4$ (~400 nm thick; uniform across the entire area). Deep etching through a hard mask of Cr/Au (10/200 nm) establishes trenches between the devices, down to a depth of ~1.5 μm into the (111) silicon supporting wafer. Anisotropic wet etching of the underlying (111) silicon with tetramethyl ammonium hydroxide (TMAH, 25 wt. % in $H_2O$, Sigma-Aldrich, USA; 30 min at 100° C.) leaves free-standing MOSFETs tethered to the wafer at their ends by bridging films of the buried oxide. Cross-sectional images in FIG. 7c illustrate that the undercut proceeds in the (110) direction, along the surface of the wafer, to allow efficient release. Details appear in FIG. 8. Free-standing MOSFETs created in this manner have total thicknesses of <2 μm, including the buried oxide layer (~1 μm). Because the SOI substrates and processing conditions are compatible with state-of-the-art commercial microelectronics fabrication facilities, dramatic reductions in the thicknesses and lateral dimensions are possible.

FIG. 1*b* illustrates an array of such MOSFETs after release from the SOI substrate and integration onto a film of silk, using the techniques of transfer printing.[17] A reactive ion etching (RIE; $SF_6$) step removes the $Si_3N_4$ after transfer. The buried $SiO_2$ and top coating of PECVD $SiO_2$ physically isolate the devices from their surroundings, thereby enabling performance that is nearly independent of substrate or subsequent encapsulating material. This versatility is important, particularly in an area such as transient electronics where choices of constituent materials can be highly unusual compared to those with proven utility in conventional electronics. FIG. 1*c* demonstrates that these types of MOSFETs can be fabricated and transferred over large areas, with high yields.

Figure 2:
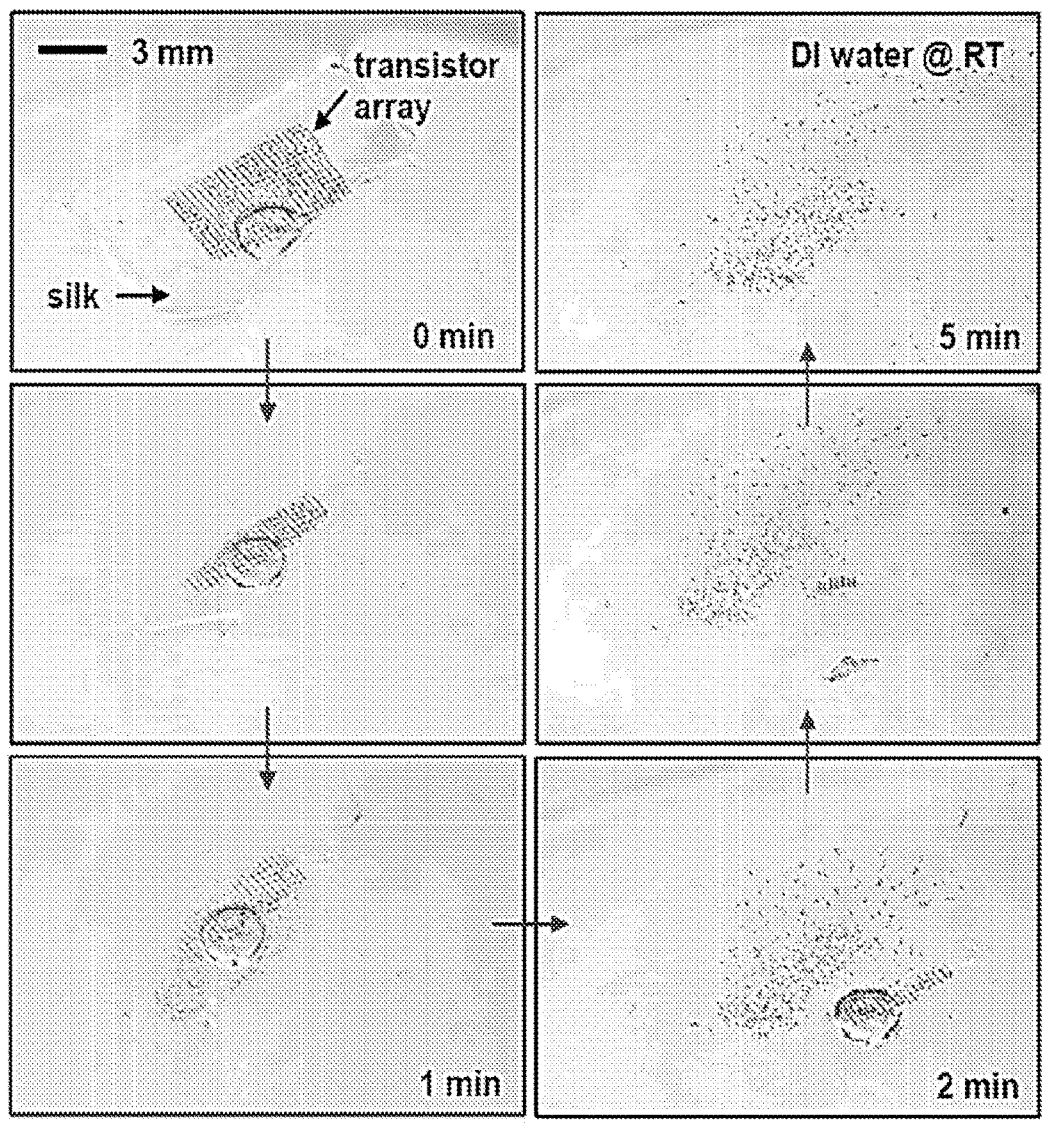
FIG. 2. Optical images at various stages of disintegration and dissolution of an array of fully formed transient transistors on film of silk. These n-channel MOSFETs have total thicknesses of <2 µm, including a base layer of thermal $SiO_2$ (~1 µm), and use Mg for the electrodes, $SiO_2$ for the gate dielectric and Si for the semiconductor. This process of dissolution occurs in DI water at room temperature.

FIG. 2 provides a set of images collected during dissolution of a system like that illustrated in FIG. 1*c*, at various times after immersion in deionized (DI) water at room temperature. Here, the silk rapidly dissolves within two minutes, thereby leading to disintegration of the array into individual devices. (The rate of dissolution of silk can be controlled over a wide range.)[18, 19] Each component then gradually disappears in a manner defined by the dissolution rates of the various constituent materials.[16] Hydrolysis consumes the Mg in several hours. Dissolution of PECVD $SiO_2$ and Si in PBS solution (pH 7.4) at room temperature occurs on a timescale of weeks; the thermal oxide takes considerably longer. In all of the materials, the rates for complete disappearance depend strongly on temperature, pH, layer thicknesses and morphology.

Figure 3:
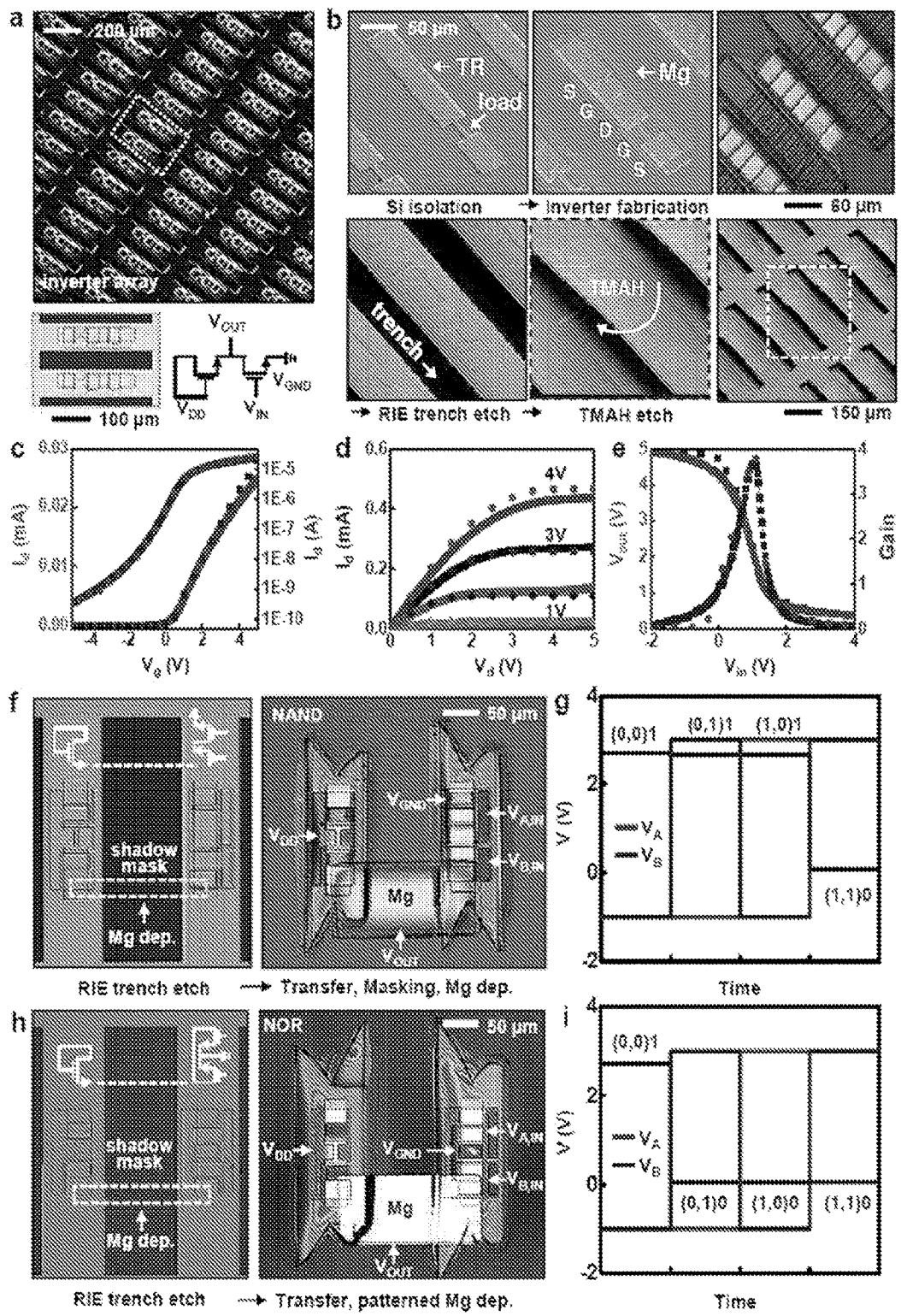
FIG. 3. Fabrication of arrays of transient inverters and logic gates and their electrical properties. a) Image of an array of inverters, optical microscope image of a representative device (lower left) and circuit diagram (lower right). b) SEM and optical microscope images of key steps in the fabrication sequence. Device isolation (upper left), metallization (upper middle), RIE trench etch (lower left), anisotropic undercut etch with TMAH (upper right, lower right), and magnified image (lower middle). c) Linear (blue) and log scale (red) transfer curves of an n-channel MOSFET (channel length ($L_{ch}$) and width (W) are 10 µm and 40 µm, respectively). The mobility and on/off ratio are 650 $cm^2/V·s$ and $>10^5$, respectively. (Experimental results (lines) and simulations (dots)) d) I-V characteristics of an n-channel MOSFET. e) Output voltage characteristics and voltage gain of an inverter (La, and Ware 20 µm and 10 µm for load transistor and 10 µm and 40 µm for input transistor, respectively). The peak gain is ~4 . f) Demonstration of a pair of n-channel MOSFETs in a logic gate (NAND) formed by interconnection with Mg. When one or both of the input transistors (at $V_A$ or $V_B$) are in their off state, the associated resistance of the input exceeds that of the load transistor, thereby leading to an output voltage in the "0" state. When the input transistors are turned on, the output voltage reaches the "1" state. Images after RIE trench etch (left) and after transfer and interconnection on a silk substrate (right). Circuit diagrams appear in the top regions of the images on the left. g) Output voltage characteristics of logic gates (NAND) at $V_{DD}$=3 V. $V_A$ and $V_B$ represent input voltages. h) Images of a NOR circuit after RIE trench etching (left) and interconnection with Mg via a shadow mask after a pair of n-channel transistors transfer printed onto silk substrate (right). The configuration of a NOR gate is similar to a NAND gate except for the connection of the input transistors. Here, parallel connection of the input transistors leads to an output state of "0", when either input is turned on. The output voltage can reach the "1" state only when both input transistors are turned off. i) Output voltage characteristics of NOR circuits at a supply voltage of 3 V ($V_{DD}$), with input voltages of $V_A$ and $V_B$.

The overall fabrication process accommodates not only individual MOSFETs, but also logic gates and small-scale integrated circuits. FIG. 3*a* shows an array of inverters, with a magnified optical micrograph and a circuit diagram. Each inverter consists of a load and an input transistor with channel lengths and widths of ~20 μm and ~10 μm, and ~10 μm and ~40 μm, respectively. The fabrication procedures (FIG. 3*b*) are similar to those described previously, including device isolation (top left), metallization (Mg evaporation, top middle), trench etching (bottom left), anisotropic undercut release (bottom right). A scanning electron microscope (SEM) image and a top view optical micrograph appear in the bottom middle and top right frames, respectively. FIG. 9 summarizes additional details. Electrical measurements on typical n-channel MOSFETs (channel length and width, $L_{ch}$=~10 μm, W=~40 μm) indicate on/off ratios of >~$10^5$, saturation and linear regime mobilities of ~530 $cm^2/V \cdot s$ and ~650 $cm^2/V \cdot s$, respectively (FIG. 3*c*). Current-voltage characteristics evaluated at different gate biases are shown in FIG. 3*d*. Voltage transfer characteristics (VTC) of the inverters (FIG. 3*e*) are consistent with expected behaviors, and gains of up to ~4 at supply voltages of ~5 V when the input voltage is swept from −2 V to 4 V (Measured values (lines) and simulations (dots)). Behaviors in the transistors and circuits were verified by SPICE (Simulation Program with Integrated Circuit Emphasis) simulation. Here, the devices were modeled using a combination of parameters, such as channel width and length, gate oxide capacitance, carrier mobility, and channel length modulation, that yielded a good match with the measurements. The circuits were simulated based on the resulting device models. The observed electrical properties are comparable to those of devices reported previously, fabricated in a similar manner with conventional, non-transient materials.[20] Circuit components with increased sophistication are possible either through extended processing on the wafer, or through the use of interconnect structures formed after transfer printing. See FIG. 10 for fabrication details. Examples of NAND and NOR gates appear in FIGS. 3*f* and 3*h*, respectively. FIGS. 3*g* and 3*i* show output voltage characteristics of NAND and NOR circuits. $V_A$ and $V_B$ are the input voltages. In case of the NAND gate, the output voltage assumes the "0" state when both input transistors are turned on. Output voltages for the "0" state and "1" state are ~0.07 V and ~2.67 V, respectively. For the NOR gate, output voltages reach the "1" state when both input voltages are low. Output voltages for the "0" state and the "1" state are ~0.06 V and ~2.7 V, respectively.

Figure 4:
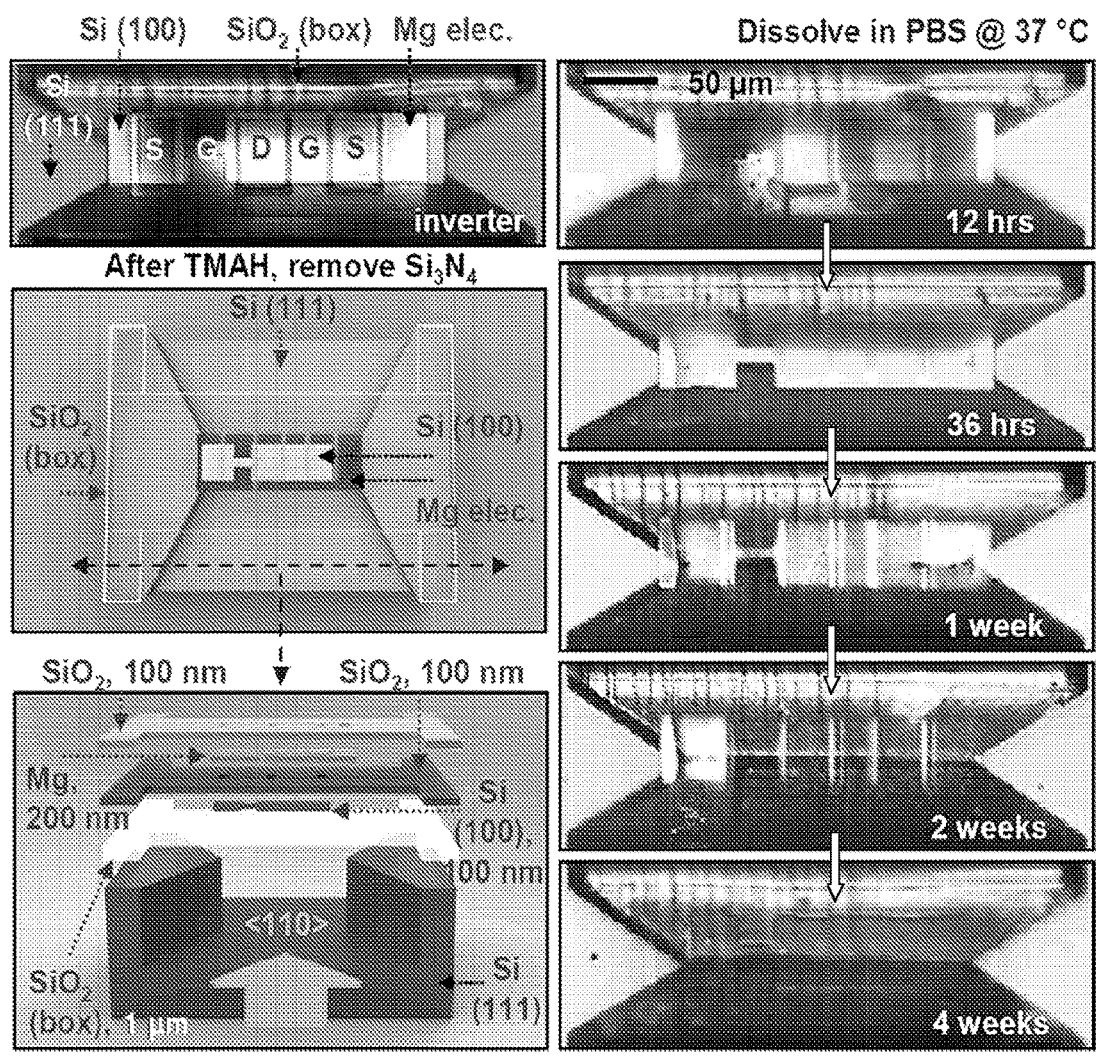
FIG. 4. Schematic illustrations and time sequence of optical micrographs during dissolution of a transient inverter undercut etched but tethered at its ends to a Si wafer substrate. Series of microscope images showing dissolution of an inverter device at various times of immersion in a phosphate buffered saline (PBS) solution at physiological temperature (37° C.) and pH (~7.4). The frames on the middle and lower left provide schematic exploded view illustrations. The constituent materials include Si (100) with a thickness of ~100 nm for the semiconductor, Mg (~200 nm) for the electrodes, and $SiO_2$ (~100 nm) for the gate and interlayer dielectric.

Inverters left in a released state on the SOI wafer allow for close examination of the dissolution processes. The image and schematic illustration in FIG. 4 provide detailed information on the device structure and material components: Mg (~200 nm) for the electrodes, Si (~100 nm) for the active layer, and $SiO_2$ (~100 nm) for the gate and interlayer dielectrics. Upon immersion in phosphate buffered saline (PBS, pH 7.4, Sigma-Aldrich, USA) solution at physiological temperature (37° C.), the various components of the device begin to dissolve, beginning with Mg, which undergoes reactive dissolution (i.e. hydrolysis) to $Mg(OH)_2$ during the first 10 hours. Although PECVD $SiO_2$ (~100 nm, interlayer dielectrics) encapsulates most of the Mg electrodes, after the exposed Mg at the contacts (source, drain, and gate) dissolves, the solution is able to undercut the Mg that lies beneath the $SiO_2$. This etching induces cracks in the $SiO_2$ that start from the edges and propagate to the center regions. This type of disintegration accelerates the overall rate of disappearance of the PECVD $SiO_2$. After these top two layers mostly disappear, the $SiO_2$ gate dielectric (~100 nm) begins to dissolve, reaching completion in two weeks or so. Over the next several weeks, the Si dissolves to form $Si(OH)_4$, with completion of this process in under 4 weeks. We note that, consistent with previous reports of conventional aqueous etching approaches for silicon,[21] the detailed rates can depend strongly on dopant type and concentration, on temperature, and on composition of the bath. The results shown here are for silicon derived directly from the SOI substrates, without additional doping. After disappearance of silicon, only the thermally grown buried oxide (~1 μm) remains, with dissolution rates that are many times slower than any of the other materials. A similar time sequence of images of interconnected arrays of logic gates on silk substrate appears in FIG. 11*a*.

Figure 5:
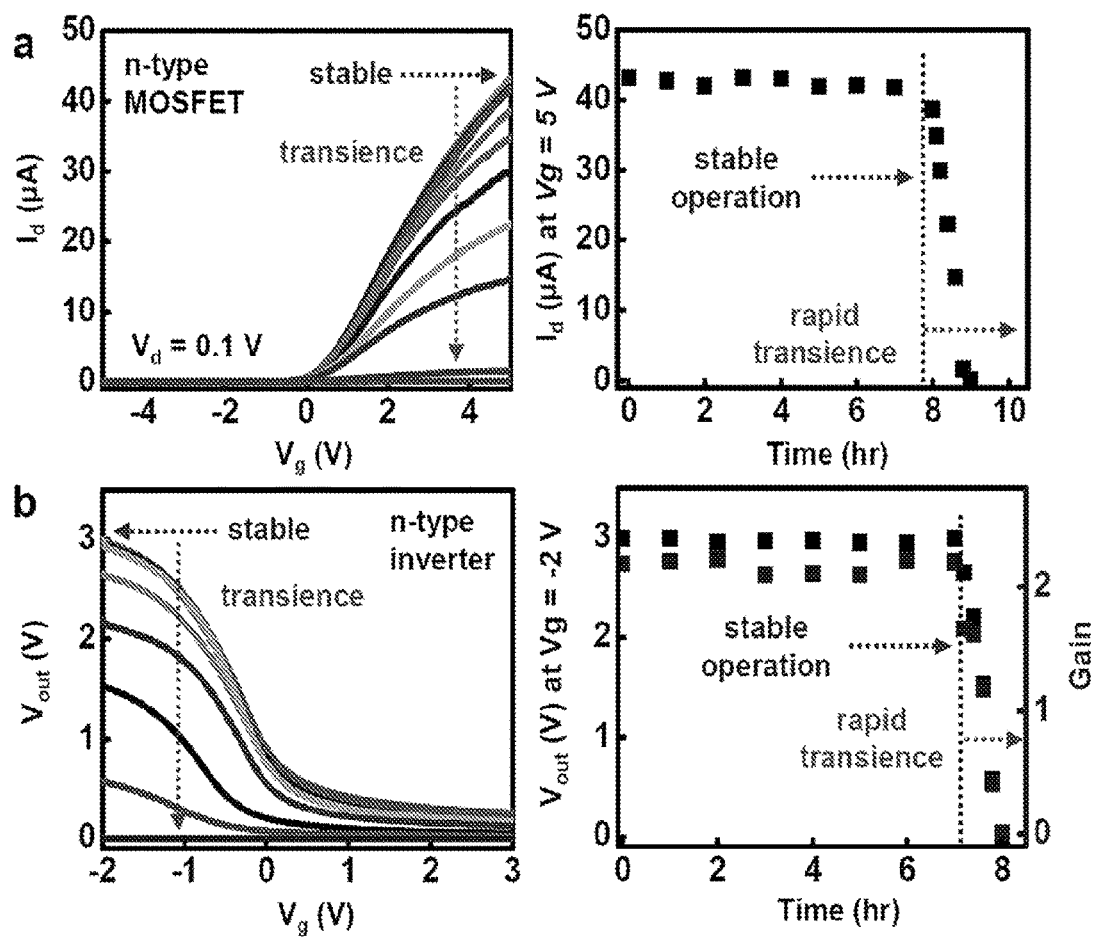
FIG. 5. Study of the change in electrical properties of transient devices measured at various times during dissolution. a) Measurement of electrical properties of a representative n-type MOSFET encapsulated with MgO (~800 nm)

Control over the kinetics of this transience behavior, and in particular of the effects on electrical properties, is an important aspect of any practical design. The most straightforward strategies involve patterned or uniform encapsulation layers, with thicknesses and compositions selected to define desired timescales for penetration of solution into the active regions. FIG. 5 shows, as an example, changes in electrical characteristics of MOSFETs and inverters encapsulated by MgO (~800 nm) as a function of time of immersion in DI water at room temperature. The measured transfer curves (at a drain voltage $V_d$=0.1 V) and drain currents ($V_d$=0.1 V, and at a gate voltage $V_g$=5 V) in FIG. 5*a* indicate that the device properties are stable (i.e. time invariant) for the first ~8 hours before they degrade quickly over the next ~45 min. A typical inverter, with key characteristics summarized in FIG. 5*b*, shows similar behavior: stable properties for the first ~7 hours followed by rapid degradation within ~50 min. Both cases exhibit two different stages in the transient behavior: i) stable operation for a time defined by removal of the transient encapsulation layer; ii) functional degradation with a timescale set by dissolution of the transient active materials. Tuning and programming of transience behavior using this strategy and more complex variants of it provide many options in design.[16]

Animal studies to examine biocompatibility were conducted by implanting a representative device in a Balb/c mouse in accordance with institutional IACUC-approved protocols as shown in FIG. 6. In this example, the implant consisted of an array of resorbable transistors fabricated on a ~5 mm×5 mm silk film, sterilized by ethylene oxide and then inserted subcutaneously through an incision on the back of the mouse (FIG. 6a, left). Here, the silk was treated in a manner that leads to slow dissolution, thereby facilitating examination of the characteristics of device resorption. After two weeks, the implanted sample (FIG. 6a, right) was found to be nicely integrated into the surrounding tissues with no signs of magnesium or silicon. The device was retrieved and the surrounding tissue was extracted to determine the inflammatory response. Histological examination of the tissue surrounding the implant site revealed the absence of any severe inflammatory response, indicating that the implanted devices induced no significant adverse effects to the animal (FIG. 6b).

The concepts, materials and fabrication techniques reported here provide a wafer-based approach to transient electronics, in which a set of foundry-compatible processing steps creates arrays of transistors, logic gates and potentially other components made of transient materials on a host wafer. The resulting device configurations are well suited for transfer printing onto transient substrates. Various examples illustrate the feasibility of this approach, and the levels of performance that can be achieved. These ideas have the potential to accelerate the translation of biodegradable electronic implants and other classes of devices enabled by transient circuits, sensors and/or actuators, into realistic, practical technologies.

Wafer-based fabrication of fully formed transient electronic devices: The fabrication began with custom silicon-on-insulator (SOI, Silicon Quest Inc., USA) wafers with a top silicon (100) layer (~2 µm thick, p-type 10-20 $\Omega\cdot$cm), a buried layer of silicon dioxide (~1 µm thick) and a Si (111) supporting substrate. Repetitive cycles of dry oxidation at 1100° C. followed by wet chemical etching in hydrofluoric acid reduced the thickness of the top silicon layer to ~100 nm. Patterned doping with phosphorous at ~950° C. using a spin-on dopant (SOD, Filmtronics, USA) defined regions for source and drain contacts. Isolated areas of silicon were defined by patterned reactive ion etching (RIE; Plasmatherm, USA) with sulfur hexafluoride ($SF_6$) gas for ~1 min. A thin layer of $SiO_2$ (100 nm) deposited by plasma-enhanced chemical vapor deposition (PECVD) served as the gate dielectric. Patterned wet-etching of this layer with buffered oxide etchant (BOE, 6:1, Transcene company, USA) opened windows for source and drain contacts. Photolithography and liftoff formed Mg electrodes (~200 nm) for source, drain and gate contacts. An additional layer of PECVD $SiO_2$ (100 nm) served as an encapsulant, with openings to the contacts formed by BOE. A 400 nm thick, unpatterned layer of $Si_3N_4$ deposited by PECVD passivated the entire area of the devices. A bilayer of Cr/Au (10/150 nm) deposited by electron beam evaporation provided a hard mask for deep trench etching by RIE down to the underlying Si (111) wafer through the buried oxide. These processed substrates were then submerged in tetramethyl ammonium hydroxide (TMAH, 25 wt. % in $H_2O$, Sigma-Aldrich, USA) for ~30 min. at 100° C. for anisotropic undercut etching of the wafer. Removal of the metal hard mask followed this etching. Next, the devices were transfer printed to a spin cast film of silk, and the passivation layer of $Si_3N_4$ was removed by RIE. In the case of logic gates, such as NAND and NOR gates, interconnection traces of Mg were deposited through fine-line stencil masks (Kapton, 12.5 µm, Dupont, USA).

Dissolution experiments: To observe dissolution of the constituent materials (Si, $SiO_2$ and Mg), a collection of undercut etched inverters on SOI were immersed in phosphate buffered saline (PBS, pH 7.4, Sigma-aldrich, USA) solution at 37° C. Optical microscope images revealed the various stages of dissolution over the course of 4 weeks. Most of the Mg electrodes (~200 nm) react with water to form $Mg(OH)_2$ within 12 hours; any residual remaining Mg dissappeared completely in 36 hours. The exposed regions of Mg dissolved first, followed by undercut dissolution of those regions of Mg that lie beneath PECVD $SiO_2$. Simultaneously, the $SiO_2$ (~100 nm, interlayer dielectrics) also began to dissolve to form $Si(OH)_4$. Due to the elimination of the underlying Mg, much of this $SiO_2$ disintegrated into tiny pieces (not visible directly), thereby accelerating the elimination of this layer. The $SiO_2$ (~100 nm) that forms the gate dielectric disappeared in two weeks. Partial dissolution of the Si occurred at the same time. Dissapearance of all materials except for the buried oxide ($SiO_2$, 1 µm) was complete within 4 weeks. Previous studies indicate that oxides grown at high temperatures have slow dissolution rates due to their morphology/density [22].

Monitoring of electrical properties during dissolution was performed using transistors and inverters encapsulated by a uniform layer of MgO (800 nm). These devices were completely immersed in DI water, but configured with external probing pads to enable continuous mesurement. Experimental results illustrate two-stage dissolution kinetics: stable device operation, without changes in electrical characteristics, followed by comparatively fast degradation in key performance parameters. The duration of the first stage depends on the rate of dissolution of the encapsulation materials and/or penetration of water through them. The second stage is determined, primarily, by relatively fast dissolution of the Mg electrodes.

Table of References for Example 1:

[1] C. T. Laurencin, A. M. A. Ambrosio, M. D. Borden, J. A. Cooper Jr., *Annu. Rev. Biomed. Eng.* 1999, 19.
[2] M. L. Kringelbach, N. Jenkinson, S. L. F. Owen, T. Z. Aziz, *Nat. Rev. Neurosci.* 2007, 623.
[3] M. H. Schoenfeld, *Circulation*, 2007, 115, 638.
[4] R. Farra, N. F. Sheppard, L. McCabe, R. M. Neer, J. M. Anderson, J. T. Santini Jr., M. J. Cima, R. Langer, *Sci. Transl. Med.* 2012, 4, 1.
[5] J. P. Singhal, H. Singh, A. R. Ray, *Polym. Rev.* 1998, 28, 475.
[6] A. Lendlein, R. Langer, *Science*, 2002, 296, 1673.
[7] K. R. Kamath, K. Park, *Adv. Drug Deliver. Rev.* 1993, 11, 59.
[8] K. S. Soppimatha, T. M. Aminabhavia, A. R. Kulkarnia, W. E. Rudzinski, *J. Control. Release*, 2001, 70, 1.

Table of References for Example 1:

[9] M. Peuster, P. Wohlsein, M. Brügmann, M. Ehlerding, K. Seidler, C. Fink, H. Brauer, A Fischer, G. Hausdorf, *Heart*, 2001, 86, 563.
[10] M. Moravej, D. Mantovani, *Int. J. Mol. Sci.* 2011, 12, 4250.
[11] T. Cavusoglu, R. Yavuzer, Y. Basterzi, S. tuncer, O. Latifoglu, *Ulus. Travma Acil Cerrahi Derg.* 2005, 11, 43.
[12] D.-H. Kim, J. Viventi, J. Amsden, J. Xiao, L. Vigeland, Y. -S. Kim, J. A. Blanco, B. Panilaitis, E. S. Frechette, D. Contreras, D. L. Kaplan, F. G. Omenetto, Y. Huang, K. -C. Hwang, M. R. Zakin, B. Litt, J. A. Rogers, *Nat. Mater.* 2010, 9, 511.
[13] D.-H. Kim, Y. -S. Kim, J. Amsden, B. Panilaitis, D. L. Kaplan, F. G. Omenetto, M. R. Zakin, J. A. Rogers, *Appl. Phys. Lett.* 2009, 95, 133701.
[14] C. J. Bettinger, Z. Bao, *Adv. Mater.* 2010, 22, 651.
[15] M. Irimia-Vladu, P. A. Troshin, M. Reisinger, L. Shmygleva, Y. Kanbur, G. Schwabegger, M. Bodea, R. Schwödiauer, A. Mumyalov, J. W. Fergus, V. F. Razumov, Helmut Sitter, N. S. Sariciftci, S. Bauer, *Adv. Funct. Mater.* 2010, 20, 4069.
[16] S.-W. Hwang, H. Tao, D. -H. Kim, H. Cheng, J. -K. Song, E. Rill, M. A. Brenckle, B. Panilaitis, S. M. Won, Y. -S. Kim, Y. M. Song, K. J. Yu, A. Ameen, R. Li, Y. Su, M. Yang, D. L. Kaplan, M. R. Zakin, M. J. Slepian, Y. Huang, F. G. Omenetto, J. A. Rogers, *Science*, 2012, 337, 1640.
[17] A. Carlson, A. M. Bowen, Y. Huang, R. G. Nuzzo, J. A. Rogers, *Adv. Mater.* 2012, 24, 5284.
[18] R. L. Horan, K. Antle, A. L. Collette, Y. Wang, J. Huang, J. E. Moreau, V. Volloch, D. L. Kaplan, G. H. Altman, *Biomaterials*, 2005, 26, 3385.
[19] T. Arai, G. Freddi, R. Innocenti, M. Tsukada, *J. Appl. Polym.* 2004, 91, 2383.
[20] H. Chung, T. Kim, H. Kim, S. A. Wells, S. Jo, N. Ahmaed, \Y. Jung, S. Won, C. A. Bower, J. A. Rogers, *Adv. Funct. Mater.* 2011, 21, 3029.
[21] H. Seidel, L. Csepregi, A. Heuberger, H. Baumgartel, *J. Electrochem. Soc.* 1990, 137, 3626
[22] K. R. Williams, K. Gupta, M. Wasilik, *J. Microelectromech. S.* 2003, 12, 761.

EXAMPLE 2

Deterministic Assembly of Releasable Single Crystal Silicon-Metal Oxide Field-Effect Devices Formed From Bulk Wafers Deterministic assembly of ultrathin metal oxide-semiconductor field-effect transistors released from the surfaces of bulk wafers with (111) orientation provides a route to high quality electronics on nearly any type of substrate. Device parameters and bias stability characteristics from transistors on sheets of plastic confirm the effectiveness of the approach and the critical roles of thermally grown layers of silicon dioxide for the gate dielectrics and passivation layers. Systematic studies of the anisotropic etching processes used to release the devices illustrate capabilities into the sub-micron thickness regime, with beneficial effects on the bending stiffness and degree of bendability.

Research in organic and inorganic materials for wearable/bio-integrated electronic devices has expanded rapidly in recent years.[1-5] Although the trend toward use of semiconductor nanomaterials has led to significant progress in various performance metrics, key limitations in cost, area coverage, and sophistication in function remain. Emerging strategies seek improved synergies between materials and manufacturing techniques used for these envisioned unconventional electronics systems and those associated with established silicon digital circuit technologies. For example, unusual device layouts and materials choices allow silicon metal oxide semiconductor field effect transistors (MOSFETs) fabricated on silicon-on-insulator (SOI) wafers to be released in ultrathin formats, suitable for integration on nearly any kind of substrate, including plastic and/or fabric.[6,7,8] Disadvantages arise from requirements for custom SOI wafers that use silicon with (111) orientation as the handle[6] and/or challenges in speed and accuracy of solution based assembly into desired arrays[7,8,9]. Recently, Zhai et al.[10] and Shahrjerdi et al.[11] reported alternative methods based on controlled exfoliation of MOSFETs from bulk silicon wafers and conventional SOI substrates, respectively. The main drawback is that the devices obtained in this manner[10] have rough bottom surface morphologies and relatively large thicknesses (20-30 µm), with corresponding limitations in bending stiffnesses and degrees of bendability. Moreover, the reported assembly/integration processes involve a one-to-one transfer of dense integrated circuits from the source wafer to the target substrate, with the potential to lead to prohibitively high costs due to inefficient utilization of the component devices. This situation is most significant in the many applications that require only sparse areal coverages of electronics, such as those in matrix arrays for displays, surgical monitoring systems and others. Alternative approaches involve specialized wafers with embedded air gaps to enable removal of integrated circuits using pick-and-place techniques. The thicknesses are, however, large (~20 µm) and the throughput in assembly can be limiting, for certain cases.[12,13]

Other schemes might exploit anisotropic etching procedures and unconventional orientations of the silicon wafers. The (100) orientation, instead of (111), has traditionally been used for complimentary MOSFET (cMOS) fabrication due to improved electron mobility and reduced interface trap density.[14] Traps at the interface between the channel and the gate oxide degrade the mobility, subthreshold swing, threshold voltage, and operational stability.[15] Consequently, n-type MOSFETs built on (111) Si typically exhibit reduced mobility values (by one third) compared to those on (100) Si.[16] The (111) orientation, however, has some appeal due to its ability to facilitate fabrication of vertical MOSFET structures, where 3D multi-gate structures improve performance by increasing the effective channel area per unit volume.[17] In addition, recent experimental studies indicate that MOSFET performance parameters, other than mobility, as well as reliability characteristics are independent of silicon orientation when the gate oxide thickness is less than 2.0 nm, due to the dominant role of direct tunneling in this regime.[18] As a result, there might be some value in revisiting the potential role of Si (111) substrates in certain cases. Here we introduce materials and device designs that allow highly flexible silicon MOSFETs to be formed directly from (111) wafers. Optimized configurations allow release from the wafer to enable high speed, deterministic assembly of large collections of individual devices onto substrates of interest, in programmable layouts and coverages by transfer printing[19,20]. Detailed electrical characterization of the devices and studies of process scaling with thickness illustrate some of the essential physics and materials science of this approach.

FIG. 13(a)-(d) outlines the steps for building releasable MOSFETs, via a sequence of schematic illustrations and microscope images. Overall, various modified processes in semiconductor fabrication yield dense arrays of devices in rectangular shapes oriented parallel to the <110> direction of the underlying wafer. This configuration allows directional wet etching of the underlying (111) wafer in a manner that undercuts the devices but leaves each one tethered to the substrate by narrow bridges (i.e. 'anchors') located at two of their four corners. In this layout, any subset of the MOSFETs can be removed from the wafer by van der Waals contact with a soft elastomer that has matching features of relief embossed on its surface. A printing step then delivers these MOSFETs to a substrate of interest; sequential repetition of this process yields desired assemblies in layouts of choice. The detailed processing begins with patterned solid state doping of phosphorous to form n+regions for source and drain contacts on a (111) bulk wafer (Virginia Semiconductor, Inc. low miscut; orientation <111>±0.1°, boron doped p-type wafer (resistivity: 8~15 ohm-cm) with 700 nm $SiO_2$ for doping mask). Each device incorporates two anchors (3 µm wide, 15 µm long) defined by a reactive ion etching procedure (STS silicon RIE, Surface Technology Systems plc) that also sets the overall lateral dimensions. The gate dielectric consists of a thermal oxide (50 nm thick) grown at 1100° C. for 17 min. This step also forms oxide on the sidewalls of the etched trenches. Patterned deposition of metal (300 nm thick Cr deposited by sputter (ATC 200 , AJA international)) creates source, drain and gate electrodes. (FIG. 13(a)) Uniform passivation of the entire substrate with a thick layer (800 nm) of low stress $SiN_x$ (by STS PECVD, Surface Technology Systems plc.) protects the gate dielectric and the contacts. To prepare for undercut wet chemical release, a reactive ion etching (PlasmaTherm) step removes the top $SiN_x$ layer (800 nm), the $SiO_2$ layer (50 nm) and the silicon to a depth of ~2 µm. (FIG. 14(b)) Immersing the wafer in a boiling solution of TMAH (tetramethyl ammonium hydroxide, 25% $H_2O$) for 90 min etches the underlying silicon anisotropically along the <110> direction. (FIG. 13(c)) After this undercut, the devices are ready for release and assembly onto foreign substrates by transfer printing[19,20]. FIG. 13(d) illustrates this process as applied to a single device, where the anchors fracture immediately upon soft contact with the elastomeric stamp, where the devices remain adhered by van der Waals forces. The right image in FIG. 13(d) shows three MOSFETs transferred onto a sheet of polyimide (PI; 1.2 µm thick). FIG. 13(e) presents a scanning electron microscope (SEM) image of the sample shown in FIG. 13(c). Here, the inset corresponds to a cross-sectional view of a partially undercut etched device. An image of 150 MOSFETs assembled on an ultrathin sheet of PET (2.5 µm thick, Mylar® film, Chemplex® industries) appears in FIG. 13(f) (after deformation) and its inset (before deformation). These devices are arranged in a 9×10 array with 1 mm pitch (bottom left), a 5×5 array with 2 mm pitch (top left), and a 7×5 array with 4 mm pitch.

Electrical measurements of n-type MOSFETs on PI are shown in FIG. 14(a)-(d). The transfer characteristics (channel width, W=80 µm and length, L=20 µm) are presented in FIG. 14(a) for three different drain voltages ($V_D$=0.1, 2.1 , and 4.1 V) in both logarithmic (solid) and linear (dashed) scales. The on/off ratio is >$10^5$ and the threshold voltage ($V_{th}$) is ~−0.72 V. Using the measured thickness of the gate oxide (50 nm) and the dielectric constant of thermal $SiO_2$ (3.9), the gate capacitance, $C_{ox}$ is calculated to be 69.1 nF $cm^{-2}$. From FIG. 14(a), the maximum transconductance, $g_m$ is 11.5 µS for $V_D$=0.1 V. The linear mobility is defined by $$\mu_{lin} = \frac{L}{W} \cdot \frac{g_m}{C_{ox}V_D}\Big|_{V_D \to 0} \quad (4)$$

and the saturation mobility is $$\mu_{sat} = \frac{2L}{WC_{ox}}\left[\left(\frac{\partial I_D^{1/2}}{\partial V_G}\right)\Big|_{V_D}\right]^2, \quad (5)$$

where $V_G$ is the gate voltage. The values of $\mu_{lin}$ and $\mu_{sat}$ are ≈405 $cm^2V^{-1} s^{-1}$ and ≈370 $cm^2V^{-1} s^{-1}$, respectively. The output electrical characteristics shown in FIG. 14(b) illustrate expected saturation behavior at high drain voltages. Moreover, the device exhibits little gate induced hysteresis, as illustrated in forward and reverse gate voltage sweeps between −6 V and 6 V, as in FIG. 14(c). The key properties, $\mu_{lin}$, $\mu_{sat}$ and the threshold voltage ($V_{th}$), at different L (10, 15, 20, 30 , and 40 µm) appear in FIG. 14(d); invariance with L is consistent with behavior that is dominated by the channel and not the contacts. For five representative MOSFETs, the on and off currents lie between 0.423 to 0.448 mA and 4.36 to 4.79 nA, respectively, at $V_D$=4.1 V. Other parameters exhibit similarly low variations from device to device. The thermal gate dielectric is important to these good performance attributes, due to the high quality of the Si and $SiO_2$ interface and its ability to minimize carrier scattering and trapping. This interface is also key to optimizing for stable operation.[11, 15] The unpassivated bottom surface can be a concern. To examine effects of bias stress, we applied $V_{GS}$ of +2 V and −2 V while holding $V_{DS}$ at 0.1 V, as shown in FIGS. 15(a) and 15(b), respectively. The off-current increases and decreases significantly for the positive and negative cases, respectively. Interestingly, the off-current slightly increases with increasing $V_{GS}$. This behavior is different from that of conventional MOSFETs, where instability in gate induced drain leakage typically leads to increasing off-current with decreasing $V_{GS}$.[21] Instead, observations in our devices resemble those associated with materials selections and process conditions for passivation layers in a-Si:H thin film transistors.[22] Passivating the back surfaces of our devices with thermally grown $SiO_2$ results in exceptional off-current stability (i.e. no change) for both positive and the negative bias stresses.[6]

The evolution of $V_{th}$ and S.S. are shown in FIGS. 15(c) and 15(d). The $V_{th}$ values remain unaffected throughout the stress conditions. The increases in S.S. induced by positive bias stress may reflect the creation of current induced defects in the channel.[23] The negative bias stress, on the other hand, causes a slight improvement in S.S., and slight decrease in on-current (FIG. 15(b)), corresponding to a ~2% reduction in mobility.

For flexible electronics, the degree of bendability increases linearly with thickness, while the bending stiffness decreases with the cube of thickness.[24] The ability to form devices with small thicknesses can, therefore, be important in many cases. Systematic studies appear in FIG. 16(a), which show the relation between silicon thickness (t) (FIG. 16(c)) and trench height (h) (FIG. 16(b)). Here, the black squares represent the thicknesses and heights for slabs prior to undercut; the red dots represent them after undercut. The ratio of etching rates along (111) and (110) planes is ~0.02 for 25% TMAH etching solution.[25] As a result, the initial thickness ((h) black dots, before etching) is reduced to a smaller value by the etching ((t) red dots; after etching). Our data show a reduction of ~500 nm for 1 h of etching, corresponding to a lateral etch distance of up to ~25 μm, and released strips with widths as large as ~50 μm. FIGS. 16(d) and (e) show representative cross-sectional SEM images for cases of 800 nm and 11 μm thick silicon slabs, respectively. These data suggest the ability to support device thicknesses in the sub-micron regime.

In summary, the concepts reported here might provide an attractive route to mechanically deformable electronics using assemblies of high performance single crystalline silicon MOSFETs fabricated on and then released from bulk wafers. Although the key performance parameters exceed previous results based on silicon derived from (111) oriented wafers,[26,27] MOSFETs[6] fabricated with (100) oriented silicon on plastic substrates reach mobilities >700 $cm^2V^{-1}s^{-1}$ and on/off ratios >$10^7$. The difference is, at least partly, a consequence of higher trap density on the (111) surface compared to (100).[21] Nevertheless, the properties of the devices reported here exceed those of most other alternatives for flexible electronics.

Table of References for Example 2:

1. S.-W. Hwang, H. Tao, D.-H. Kim, H. Cheng, J.-K. Song, E. Rill, M. A. Brenckle, B. Panilaitis, S. M. Won, Y.-S. Kim, Y. M. Song, K. J. Yu, A. Ameen, R. Li, Y. Su, M. Yang, D. L. Kaplan, M. R. Zakin, M. J. Slepian, Y. Huang, F. G. Omenetto, and J. A. Rogers, *Science* 337, 1640 (2012).
2. T. Sekitani, T. Someya, *MRS Bull.* 37, 236 (2012).
3. S. C. B. Mannsfeld, B. C. K. Tee, R. Stoltenberg, C. V. H. H. Chen, S. Barmann, B. V. O. Muir, A. N. Sokolov, C. Reese, Z. Bao, *Nat. Mater.* 9, 859 (2010).
4. C. Pang, G.-Y. Lee, T.-i. Kim, S. M. Kim, H. N. Kim, S.-H. Ahn, K.-Y. Suh, *Nat. Mater.* 11, 795 (2012).
5. K. Takei, T. Takahashi, J. C. Ho, H. Ko, A. G. Gillies, P. W. Leu, R. S. Fearing, A. Javey, *Nat. Mater.* 9, 821 (2010).
6. H.-J. Chung, T.-i. Kim, H.-S. Kim, S. A. Wells, S. Jo, N. Ahmed, Y. H. Jung, S. M. Won, C. A. Bower, J. A. Rogers, *Adv. Func. Mater.* 21, 3029 (2011).
7. S. W. Lee, R. Bashir, *Adv. Mater.* 17, 2671 (2005).
8. S. A. Stauth and B. A. Parviz, *Proc. Natl. Acad. Sci. USA* 19, 13922 (2006)
9. R. J. Knuesel, H. O. Jacobs, *Proc. Natl. Acad. Sci. USA* 107, 993 (2010)
10. Y. Zhai, L. Methew, R. Rao, D. Xu, S. K. Banerjee, *Nano Lett.* 12, 5609 (2012).
11. D. Shahrjerdi, S. W, Bedell, *Nano Lett.* 13, 315 (2013).
12. J. N. Burghartz, W. Appel, H. D. Rempp, M. Zimmermann, *IEEE T. Electron Dev.* 56, 321 (2009)
13. E. A. Angelopoulos, M. S. Al-Shahed, W. Appel, S. Endler, S. Ferwana, C. Harendt, M. Hassan, H. Rempp, M. Zimmermann, J. N. Burghartz in *Solid-State Device Research Conference (ESSDERC)* 2012: *Proceedings of the European*, Bordeaux France, 17-21 Sep. 2012 edited by Yann Deval (IMS Lab., University of Bordeaux, France), pp 141-144.
14. R. F. Pierret, *Semiconductor Device Fundamentals* (Addison-Wesley, Natick, MA, 1996) Ch 18.
15. G. Barbottin, A. Vapaille, *Instabilities in Silicon Devices Vol. 2* (Elsevier, Amsterdam, 1989) Ch 15.
16. S. Takahi, A. Toriumi, M. Iwase, H. Tango, *IEEE Trans. Electron Dev.* 41, 2363 (1994).
17. C. Fink, K. G. Anil, H. Geiger, W. Hansch, F. Kaesen, J. Schulze, T. Sulima, I. Eisele, *Solid State Electron.* 46, 387 (2002).
18. H. S. Momose, T. Ohguro, S. Nakamura, Y. Toyoshima, *IEEE Trans. Electron. Dev.* 49, 1597 (2002).
19. M. A. Meitl, Z.-T. Zhu, V. Kumar, K. J. Lee, X. Feng, Y. Y. Huang, I. Adesida, R. G. Nuzzo, J. A. Rogers, *Nat. Mater.* 5, 33 (2006).
20. A. Carson, A. M. Bowen, Y. Huang, R. G. Nuzzo, J. A. Rogers, *Adv. Mater.* 24, 5284 (2012).
21. J. H. Stathis, S. Zafar, *Microelec. Rel.* 46, 270 (2006).
22. Y.-K. Choi, D. Ha, T.-J. King, and J. Bokor, *Jpn. J. Appl. Phys.* 42, 2073 (2003).
23. Y. Kuo, Thin Film Transistors Materials and Processe Vol. 1 (Klewer Academic, Norwell MA, 2004) Ch 6.
24. J. A. Rogers, M. G. Lagally, and R. G. Nuzzo, *Nature* 477, 45 (2011).
25. K. Sato, M. Shirkida, T. Yamashiro, K. Asaumi, Y. Iriye, M. Yamamoto, *Sens. Actuators, A* 73, 131 (1999).
26. S. Mack, M. A. Meitl, A. J. Baca, Z.-T. Zhu, and J. A. Rogers, *Appl. Phys. Lett.* 88, 213101 (2006).
27. A. J. Baca, M. A. Meitl, H. C. Ko, S. Mack, H.-S. Kim, J. Dong, P. M. Ferreira, J. A. Rogers, *Adv. Funct. Mater.* 17, 3051 (2007).

EXAMPLE 3

Manufacturing Strategies

The proposed scheme involves two parts. The first exploits methods for retrieving μ-die from a wafer that supports fully processed transient CMOS, and then for delivering these μ-die to a receiving substrate, at high throughputs and with accurate registration control. The second relies on thin film processing and lamination techniques for integrating μ-die with transient passives on a transient substrate, to allow packaging and interconnection to other components of the system, such as the transient antenna, the sensors and the primary battery pack. The following describes these two sub-tasks in detail. The overall process flow appears in FIG. 17, in which these two steps occur sequentially to yield functional systems with characteristics that meet the CONOPS requirements.

Microtransfer Printing—This manufacturing method offers unique capabilities in retrieving semiconductor microdevices released from source wafers (e.g. microscale light emitting diodes, vertical cavity surface emitting lasers, integrated circuits, solar cells and others) and then transferring them, in a printing-like process, to target substrates, at room temperature and with high speed, precise control. A picture of an automated tool that is currently in commercial use in a photovoltaic manufacturing facility appears in FIG. 17. Here, the end-to-end throughput capacity corresponds to microtransfer printing (μTP) of ~one billion microscale solar cells per year; FIG. 18 shows a high concentration photovoltaic module that uses 500,000 printed solar microcells. μTP has also been successfully demonstrated with non-transient CMOS μ-die in the manufacturing of advanced display systems. FIG. 18 shows a high definition active matrix backplane that incorporates >55,000 printed CMOS μ-die as pixel drivers.

Recent efforts establish the ability of μTP to integrate non-transient CMOS μ-die on substrates for interconnection with transient metal traces, as illustrated in FIG. 19. This base of knowledge and existing tool set will provide, with non-transient CMOS μ-die, (a) transfer yields of ~99.9%, (b) throughputs approaching one million μ-die per hour, in programmable layouts and configurations, (c) automated operation with CNC programmability, (d) overlay registration of ~0.5 μm.

These capabilities are extended by (a) adapting established μTP tools for use with transient CMOS μ-die and demonstration in the manufacturing flow and (b) implementing the resulting technology in a manufacturing mode. The first topic will involve extension of μTP to μ-die dimensions (100 to 10 μm) that provide an option for transience by disintegration into individual pieces not readily visible to the unaided eye.

Parameters of interest include: μTP with dummy silicon μ-die (lateral dimensions from 100 to 10 μm, in all cases) at yields >75%, placement accuracy better than 5 μm and throughputs of 10,000 μ-die per hour; μTP with transient CMOS μ-die at yields >75%, placement accuracy better than 5 μm and throughputs of 10,000 μ-die per hour. μTP with transient CMOS μ-die at yields >95%, placement accuracy better than 1 μm and throughputs of 100,000 μ-die per hour; μTP for full fabrication of the CONOPS.

Peel-and-stick Lamination: This part of the manufacturing flow involves formation of transient passive components on temporary substrates and integration with printed transient CMOS μ-die. A process we refer to as peel-and-stick lamination (PaSL) delivers the resulting integrated system onto a transient substrate, where removing sacrificial layers and then coating with transient encapsulants completes the process. This scheme is important because it decouples the development of optimized transient materials (substrate, encapsulants, packages) from requirements associated with manufacturing; nearly any class of material can be considered.

FIG. 20 provides schematic, exploded view illustrations of a sequence for PaSL designed to demonstrate the concepts using silicon devices interconnected with Mg, and PLGA as the transient substrate. The first step involves fabrication of active and passive components and associated interconnects on a temporary substrate (here, a silicon wafer). A layer of polyimide (D-PI) serves as a coating designed to ensure high yield μTP and to facilitate thin film processing of transient passives and interconnects. Etching an underlying layer of poly(methylmethacrylate) (PMMA) in a two-step dry and wet process, enables release of the entire system from the wafer. A spin-cast or laminated layer of PLGA provides a transient substrate, and also a means to peel the system from the wafer and flip it over, for removal of the D-PI by dry etching. The result is a fully transient piece of electronics, with both active and passive components, on a transient substrate that does not have to accommodate any of the key processing steps. In this manner, the transient electronic device substrate is decoupled from the processing associated with manufacture of the key electronic components.

This scheme is generally applicable to wide ranging classes of transient materials, as illustrated in FIG. 21. Furthermore, the resulting systems are thin and flexible, thereby allowing for their lamination onto various surfaces and packages of interest. FIG. 22 provides some examples, of the general type that are important in bonding the CONOPS electronics into a final package.

We build on these demonstrations of PaSL to develop a full manufacturing flow for transient electronics that meet CONOPS specifications. Key parameters are: PaSL onto PLGA with dummy silicon μ-die, delivered by μTP and interconnected with Mg, at yields >75%, and areas of up to ~10 cm$^2$. PaSL onto transient material substrates with dummy silicon μ-die, delivered by μTP, interconnected with Mg and combined with transient passives, at yields >75%, and areas of up to ~10 cm$^2$. PaSL demonstrated with μTP and all key materials and devices for the CONOPS, at yields >85% and areas up to ~10 cm$^2$. PaSL with μTP for full fabrication of the CONOPS deliverable.

EXAMPLE 4

Fabrication and Manufacturing Platform Development

The manufacturing strategy combines fabrication of devices and integrated circuit sub-systems using state-of-the-art CMOS fabrication facilities, on customized SOI substrates with strategic device layouts and non-traditional material combinations. Release of the active elements and delivery by the techniques of microtransfer printing (μTP) facilitates integration with transient materials for substrates and encapsulation layers.

Releasable CMOS Devices via Use of SOI (111) Substrates: Specialized SOI wafers in which the handle substrate has a (111) orientation offer unique opportunities for undercut etching and release. The result enables transfer, selectively and at the level of individual components and devices, to a separate, device substrate for system integration. In preliminary work, we established the feasibility of this process, through release of fully formed transient metal-oxide semiconductor field-effect transistors (MOSFETs) fabricated from SOI (111), as shown in FIG. 23. The SOI comprises a (111) silicon handle wafer, a buried layer of silicon dioxide ($SiO_2$), and a top layer of active Si with conventional, (100) orientation. This type of substrate is unusual, and designed specifically to allow anisotropic etching of (111) silicon as a means for releasing the overlying devices/circuits. Wafer bonding, transfer, polishing and etching techniques developed for radiation hardened circuits are adapted to create SOI (111) substrates. The sequence starts with a commercial quality SOI wafer to assure a defect-free device layer. This wafer is coated with an oxide, and it is then bonded to a bulk (111)-oriented silicon wafer. The original (100) substrate is then removed. This process leaves a high quality silicon device layer on a (111)-oriented handle wafer, thereby providing a platform for fabrication of high-performance CMOS circuits.

The preliminary results of FIG. 23 involve doping of active regions in the top silicon and deposition of a gate dielectric of $SiO_2$, followed by device isolation and Mg evaporation to form source, drain, and gate electrodes. The isolated devices are then protected with a mask comprising stacked layers of $SiO_2$ and $Si_3N_4$. A Cr/Au bilayer (Cr/Au, 10/150 nm) is deposited to form a mask for reactive ion etching of trenches that extend through the buried oxide layer and down into the handle wafer. Anisotropic etching with tetramethyl ammonium hydroxide (TMAH; 25%; ~30 min. at 100° C.) removed silicon along the surface of the wafer at a rate approximately 100 times faster than into its depth, thereby undercutting the devices to form freely suspended transistors anchored to the underlying wafer at narrow points at their edges. In this work, the channel lengths/widths were 10/40 μm, and the contact sizes are 20/40 μm. The lateral dimensions of an individual single device island are 100/250 μm. This process is a starting point for manufacturing processes of CMOS devices.

Properties of Transient Transistors Fabricated on SOI (111) Substrates: Transistors fabricated and then undercut from SOI (111) wafers using the steps described in the previous section exhibit high performance (mobility ~650 $cm^2$/Vs; on/off ratio >$10^5$), as illustrated in FIG. 24. The most important aspect of this scheme is that it may be used at manufacturing scale, in a foundry type fabrication environment.

Transfer Printing as a Manufacturable Path to Integration: Released devices of the type described herein are retrieved from the source wafer using contact stamps, such as soft elastomeric stamps, and then transferred, in a printing-like process, onto a transient device substrate, for subsequent interconnection (e.g., "processing") to make functional systems. This process of microtransfer printing (μTP), a representative automated tool, and the overall envisioned manufacturing flow, appear in FIG. 25. This scheme is used in other contexts, and is now available in extremely sophisticated forms, compatible with manufacturing. For example, tools exist at a pilot line photovoltaic manufacturing facility, capable of transferring up to a billion components (microscale solar cells in that case) per year[9]. Within the context of the process, μTP brings the following capabilities: (1) By delaying the introduction of the substrate/encapsulation materials until after the circuit components and sensors have been fabricated, it enables the development of substrate/encapsulation materials based solely for their ability to support controlled and triggerable transience, and without consideration of their compatibility in cleanroom (e.g., foundry) processing environments, and (2) By permitting use of temporary 'carrier' substrates (i.e. (111) silicon wafers in the proposed approach) for the CMOS fabrication, it enables highly optimized choices of materials and processes for manufacturing. Configurations and combinations of these materials can be designed to simultaneously address the need for high performance operation and triggerable transience. Adaptations and extensions of the existing tool of μTP for transient electronics represent the focus here. The current system can be used, as it already provides (1) transfer yields of ~99.9%, (2) parallel transfer of arrays of devices and microdie, at throughputs approaching one million parts per hour, (3) automated printing with a standard CNC programmable tool, (4) overlay registration of ~0.5 microns. Establishing these capabilities in which CMOS devices are built on SOI (111) substrates and then printed onto transient substrates represents the initial focus of this work.

Tools for μTP that bring this process into closer alignment with standard, high-speed machines for pick-and-place assembly will be important. Our approach interleaves cycles of a large number of small area print heads in a high speed machine, adapted from a pick-and-place tool platform. The receiving substrate mounts on a translating XY table. A magazine of donor substrates, capable of linear indexing, brings appropriate donor wafers to the stamp-head. High placement rates (as high as 100,000 placements per hour) with accuracy and repeatability (~1 micron) can be achieved. With a 10 mm square stamp, a multiplier of 10,000 (assuming a pitch of 100 microns between collections of ribbons/platelets) could easily be achieved, producing effectively 100 to 1000 million transfers per hour. The large number of available stamp heads and donor magazine positions enables process flexibility, on-tool reworking and overall process robustness. Additionally, the foundational machinery, while complex, builds on related platforms for printed circuit board assembly. Such platforms can be adapted to this form of high speed μTP.

Integration with CMOS Fabrication Processes: Transient CMOS components are developed using materials and processes established first using adapted forms of the MITLL fully depleted silicon on insulator (FDSOI) architecture. This process is an ideal for transience because the active silicon layer is tens of nanometers thick, and the entire active circuit layer including wiring and dielectrics is approximately 10 μm thick. This process technology has optional modules to optimize RF and low-power operation, and can be implemented or integrated with transient metals such as W and Mo. Ultra-low power performance can be achieved by operating the devices in the subthreshold regime, to enable circuit designs described herein. Transistors optimized for operation at 0.3 V can achieve a 97% reduction in switching energy compared to conventional transistors. This technology is well suited for application in embedded systems, which are constrained to operate on limited RF power harvested from the environment or transient primary batteries, as described herein.

This process yields simple test devices and microcircuits that can be released for μTP, and integrated on transient substrates. This work demonstrates working process flows. Optical and/or physical alignment marks and sensors defined on a substrate of interest (FIG. 27) guide the printing process.

Surfaces of transfer devices, donor substrates and/or receiving substrates may possess specific relief patterns, such as alignment channels and/or grooves, useful for providing proper alignment between a transfer device and a substrate surface to ensure that electronic devices are placed according to a selected pattern with high fidelity. Alternatively, surfaces of substrate layers in the present invention may possess specific relief patterns, such as alignment channels and/or grooves, useful for providing proper alignment between a composite patterning device and an actuator such as a printing device, molding device or contact photolithography apparatus having complimentary (i.e. mating) channels and/or grooves. Alternatively, surfaces of the present invention may possess specific relief patterns, such as alignment channels and/or grooves, useful for providing proper alignment between a composite patterning device and substrate surface having complimentary (i.e. mating) channels and/or grooves. As will be understood by a person of ordinary skill in the art, use of such "lock and key" alignment mechanisms, channels, grooves and systems are well known in the art of microfabrication, and may easily be integrated into the present invention.

The present invention provides methods and pattering devices and/or substrate surfaces having specific relief patterns, such as alignment channels, troughs and/or grooves, useful for providing proper registration and alignment of patterning devices and substrate surfaces. Particularly, use of "lock and key" alignment systems comprising complimentary (i.e. mating) relief features and recessed regions is useful in the present invention because engagement of complementary features constrains the possible relative orientations of the contact surface of a patterning device and a substrate surface. The ability to constrain the relative orientation of these elements is particularly useful for fabricating devices and device arrays with good placement accuracy over large substrate areas.

In one aspect, the present invention includes alignment systems using a patterning agent for establishing and maintaining a selected spatial alignment between the contact surface of a patterning device, such as the contact surface of a composite patterning device or the contact surface of a single layer patterning device, and a selected region of the substrate surface. In the context of this description, the term "patterning agent" refers to one or more materials that are provided between at least a portion of the contact surface of a patterning device and a substrate surface undergoing processing. In this aspect of the present invention, the patterning agent functions to facilitate proper alignment and engagement of complementary relief features and recessed regions in a manner resulting in good registration of these elements. Patterning agents of the present invention may provide functionality other than or in addition to facilitating proper alignment of a patterning device and a substrate surface. In one embodiment, patterning agents of the present invention comprise an optical filtering medium for a photomask of the present invention. In another embodiment, patterning agents comprise a transfer material that is molded onto a substrate surface, for example a prepolymer material that is molded into a pattern embossed on the substrate surface upon exposure to electromagnetic radiation or upon increasing temperature. Patterning agents of the present invention may also provide a multifunctional character such as a combination of facilitating alignment of a contact surface of a patterning device and a substrate surface undergoing processing and providing optical filtering and/or a transfer material for patterning a substrate surface.

In one embodiment, patterning agents of the present invention act as lubricants by reducing friction generated between a mating contact surface and substrate surface pair of an alignment system, such as a lock and key registration system. By reducing friction, the patterning agent allows the patterning device and the substrate to establish conformal contact and move relative to each other, thereby sampling a range of possible relative orientations. In this aspect of the present invention, additional mobility provided by the patterning agent allows the patterning device and substrate surface to realize a stable, selected relative orientation characterized by effective coupling between complementary relief features and recessed regions on the mating surfaces. Effective patterning agents facilitate establishing correct registration without interfering with establishment of conformal contact. Useful patterning agents include fluids, such as liquids and colloids, thin films and particulate materials. Exemplary patterning agents include Optical Brightener, Benetex OB-EP from Mayzo, Parker ink, Water soluble black wooden dye Powerder from Constantines Wood Center.

Patterning devices of this aspect of the present invention have a contact surface having a plurality of recessed regions or relief features having shapes and physical dimensions that are complementary to recessed regions or relief features on a substrate surface undergoing processing. Patterning devices of this aspect of the present invention also have a means for introducing the patterning agent into at least a part of the region between the contact surface and the substrate surface. Means for introducing the patterning agent can be a fluidic channel, groove or may involve wetting the contact surface or substrate surface prior to establishing conformal contact, for example using a dipping system. To achieve registration, the patterning device and substrate surface are gradually brought into contact by establishing an appropriate force, for example a force directed orthogonal to a plane containing at least a portion of the contact surface. Optionally, alignment may involve movement of the mating surface of the patterning device and the substrate surface in other directions, for example by lateral movement of the surfaces.

Advantages of this patterning approach of the present invention include (i) it is compatible with the types of composite patterning devices described throughout this application, (ii) the patterning agent can have low viscosity, which enables it to flow rapidly and effectively as the patterning device is brought into contact with the patterning agent (which helps to push most of the patterning agent out of the regions that correspond to raised areas on the patterning device), (iii) it lubricates the interface between the contact surface (or coated contact surface) and the substrate surface (or coated substrate surface), and (iv) it does not alter the stretchability of the patterning device, which is an important characteristic, especially if the patterning device has to stretch to match the lock and key features (due to slight deformations in the substrate, for example).

These processes may be used to obtain wireless sensor systems. Due to their relative simplicity, the various sensor types are fabricated separately, using cleanroom processing.

Table of References for Example 4:

[1] H. Zhou, J.-H. Seo, D. M. Paskiewicz, Y. Zhu, G. K. Cellar, P. M. Voyles, W. Zhou, M. G. Lagally and Z. Ma, "Fast flexible electronics with strained silicon nanomembranes," *Scientific Reports*, 3, 1291, 2013.

| Table of References for Example 4: |
| --- |
| [2] Z. Chen and C. Lu, "Humidity Sensors: A Review of Materials and Mechanisms," *Sensor Letters*, 3: 274-295, 2005.
[3] V. Ducéré, A. Bernès and C. Lacabanne, "A capacitive humidity sensor using cross-linked cellulose acetate butyrate," *Sensors and Actuators B: chemical*, 106: 331-334, 2005.
[4] A. Richter, G. Paschew, S. Klatt, J. Lienig, K.-F. Arndt and H.-J. Adler, "Review on Hydrogel-based pH Sensors and Microsensors," *Sensors*, 8: 561-581, 2008.
[5] P. Kurzweil, "Metal Oxides and Ion-Exchanging Surfaces as pH Sensors in Liquids: State-of-the-Art and Outlook," *Sensors (Basel)*, 9: 4955-85, 2009.
[6] W.-D. Huang, H. Cao, S. Deb, M. Chiao and J. C. Chiao, "A flexible pH sensor based on the iridium oxide sensing film," *Sensors and Actuators A: Physical*, 169: 1-11, 2011.
[7] A. Fulati, S. U. Ali, M. Riaz, G. Amin, O. Nur and M. Willander, "Miniaturized pH Sensors Based on Zinc Oxide Nanotubes/Nanorods," *Sensors*, 9: 8911-8923, 2009.
[8] S. M. Csutak, J. D. Schaub, W. E. Wu, R. Shimer and J. C. Campbell, "CMOS-compatible high-speed planar silicon photodiodes fabricated on SOI substrates," *Quantum Electronics, IEEE Journal of*, 38: 193-196, 2002.
[9] http://www.semprius.com/ |

FIG. 28A is a process flow diagram of a method of making a transient electronic device. The steps may include fabricating 100, transfer printing 200, and removal 300 of release layer and providing 400 a substrate layer. Steps 300 and 400 may occur in any order or relatively simultaneously, as indicated by the split flow at steps 300 and 400. The substrate layer and components are released 500. The substrate layer and components are flipped 600 and subsequent processing 700 as desired, such as by introduction of components to make the device transient, are performed. FIG. 28B is a process flow diagram providing optional steps 702-708 performed as part of processing 700. For example, optional steps include but are not limited to adding a transient device component 702, replacing a component with a transient component 704, providing a transient substrate 706, and providing an interconnect structure comprising a selectively removable material 708. The steps of FIG. 28 are schematically illustrated in FIG. 29. Panels A-C show transfer printing of components 100 by a transfer stamp 110 from a mother substrate 120 (A) to a handle substrate 220 that supports a release layer 210 (C). The release layer 210 is removed and a substrate layer 410 contacted with a top surface of the components (D). The substrate layer may be used to remove the substrate and components from the handle substrate (E) and then flipped (F) so that the previous downward facing surface is oriented in an after-flipping upward orientation. Subsequent processing (G) may be performed, such as by deposition of interconnects 710 and an encapsulating layer 720. In an aspect, the interconnects may be curved or bent to facilitate device stretching and flexibility.

EXAMPLE 5

High Performance Bioresorbable/Transient Electronics on Biodegradable Polymers

Materials and fabrication approaches that allow integration of bioresorbable/transient electronics onto diverse classes of bioresorbable substrate materials are presented in this example. By first depositing, patterning and etching the materials for the electronics and then integrating them on a substrate of interest, it is possible to use nearly any type of biodegradable material for this purpose. Component and system-level studies of various devices and biodegradable polymers illustrate the capabilities and operational aspects. Dissolution studies and mechanics modeling results highlight different modes for transient behavior.

Biodegradable polymers are used extensively in medical devices. Examples include carriers for controlled drug release and scaffolds for tissue engineering.[1-7] The ability to integrate fully biodegradable, high-performance electronics and sensors with these materials could significantly expand the functional capabilities in biomedicine, with additional implications in areas such as consumer electronics and environmental sensors, where degradability could eliminate waste streams associated with recycling/disposal and practical difficulties in device collection/recovery, respectively. Work toward this goal involves strategies that range from use of ultra-miniaturized device components[8,9] to organic/bio-organic active materials.[10-12] More recent approaches exploit high performance bioresorbable semiconductors, such as ultrathin films of silicon and metal oxides, with appropriate metals and inorganic dielectrics.[13-16] Advanced schemes allow integration of fully formed device elements of this type with resorbable substrates[15]. Here, a final set of processing steps defines electrical interconnects and other features to yield completed systems. Published examples include RF harvesters, solar modules, ring oscillators and logic gates. A key challenge is that the substrate materials must have the necessary chemical resistance and temperature stability to accommodate this processing. Examples in the literature avoid these issues by, for instance, use of shadow masks, rather than photolithography and etching, to define the interconnect structures. Severe limitations in resolution and materials options associated with this approach, however, motivate the development of alternative strategies. In this example, we demonstrate one possibility and illustrate its use in various representative devices and arrays, with a range of resorbable substrate materials, including poly lactic-co-glycolic acid (PLGA), a copolymer of poly lactic acid (PLA) and poly glycolic acid (PGA), PLA, polycaprolactone (PCL) and rice paper. The resulting systems can be laminated onto various other supporting surfaces with either planar or non-planar shapes. The content begins with descriptions of these procedures and mechanical/chemical considerations in materials selections. Various demonstrations, including devices that incorporate functional arrays of hydration sensors, illustrate the capabilities.

The key to expanding the materials options is to separate deposition, etching and lithographic patterning associated with fabrication of the electronic components from the biodegradable substrates. FIG. 30a describes procedures that begin with spin casting of a sacrificial layer of poly (methylmethacrylate) (PMMA, MicroChem, USA) followed by an ultrathin layer of diluted polyimide (D-PI) (~200 nm) on a silicon (Si) wafer. Transfer printing then delivers patterned, doped silicon nanomembranes (Si NMs) or fully formed ultrathin silicon microdevices to the surface of the D-PI layer in spatial layouts that match requirements. Depositing other materials and patterning them by photolithography yield completed systems of electronics, integrated sensors and/or power supplies. For examples reported here, these steps include plasma-enhanced chemical vapor deposition (PECVD) of $SiO_2$ (~50 nm) for gate and interlayer dielectrics, and Mg (~300 nm) for source, drain, gate contacts, and interconnects. Afterward, spin casting defines another layer of D-PI, uniformly on top of the resulting set of devices. Etching openings in certain regions of the polymers (D-PI, PMMA) and, if necessary, other layers such as the $SiO_2$, exposes the PMMA at the base. Immersing a sample processed in this way in acetone removes the PMMA, to release an ultrathin circuit that can be lifted from the Si wafer onto the surface of a slab of PDMS using the techniques of transfer printing. Next, reactive ion etching ($O_2$ gas, March RIE) eliminates the exposed, bottom layer of D-PI while the structure is still on the PDMS. Transfer to a biodegradable substrate allows removal of the top layer of D-PI, using reactive ion etching again, to complete the process. The image in the left frame of FIG. 30b presents an array of transient Si n- and p-channel transistors on a coating of PLGA cast on a sheet of paper with printed text and logos. A magnified view appears in the right frame of FIG. 30b, with a microscope image of a representative device in the inset. FIG. 30c provides measurement results from a complementary metal-oxide-semiconductor (CMOS) inverter. The gain and threshold voltage ($V_{th}$) are ~50 and −1 V with $V_{dd}$=10 V, respectively. The performance is comparable to that of devices prior to transfer, and of results achieved using low resolution shadow masking techniques reported previously.[14]

The versatility of these schemes and their compatibility with nearly any class of substrate motivate consideration of desired properties in the materials. PLGA is one of the most popular biodegradable polymers because its properties can be tuned by adjusting molecular weight and the ratio of lactide to glycolide. In water, PLGA undergoes degradation via hydrolysis of its ester linkages. Increasing the lactide content increases the hydrophobicity and decreases the water absorption, thereby reducing the degradation rate. PCL, as one of earliest studied biopolymers, is also of interest, partly because of its wide commercial availability. This polymer is hydrophobic and semi-crystalline, with a degree of crystallinity that can be tuned by molecular weight and processing conditions. The advantages of PCL include adjustable degradation kinetics and availability of simple procedures for casting and shaping. Since the degradation rate of PCL is smaller than that of many other polymers, it is popular for long term implantable devices. Additional information on chemical structures and properties of biodegradable polymers appears in FIG. 34 and Table 1. Rice paper provides another option, due to its low cost availability, and suitability in ingestible device embodiments.

TABLE 1

Properties of biodegradable polymers

| Polymer | $T_g$ (° C.) | Tensile strength (MPa) | Flexural strength (MPa) | Modulus (GPa) | Elongation (%) | Degradation time (Weeks) | Swelling (water uptake) |
|---|---|---|---|---|---|---|---|
| PLA (Poly L-lactide) | 58-59 | 20-40 | 70 | 2.7-3.2 | 2.5 | 12-18 | 5-10% |
| PLGA[a] (Poly lactide co-glycolide) | 40-60 | 40-50 | 100 | 2.0 | 3-10 | 4-5 | 5-18% |
| PCL (Polycaprolactone) | −60 | 16 | 11-15 | 0.4 | 300-500 | >24 | 0.5-1.0% |

[a]Properties vary in ratios of PLA to PGA, and molecular weight.

Flexible transient electronic systems can be formed on films of these or other biopolymers, with subsequent possibility for integration onto various other supports, ranging from sheets of paper to gloves. Thin layers of PLGA can serve as adhesives in these cases. FIG. 21a presents a photograph of an array of transient CMOS inverters on a thin film of PLGA (15~20 μm thick), wrapped on a glass rod, including a magnified image in the inset. In addition to spin-casting, melt-processing can be used to form substrates of these bioresorbable polymers. FIGS. 21b and 21c show images of a transient Si CMOS inverter circuit on PCL (~1 mm thick) and PLA (~1 mm thick), respectively. Both polymers provide sufficient tackiness to facilitate release during transfer printing at elevated temperatures (150~180° C.). FIG. 21d illustrates a similar transient CMOS system on rice paper (~200 μm thick). Here, applying a small amount of water to the surface of the substrate softens the material in a way that facilitates transfer. Additional images appear in FIG. 35. FIG. 31 shows the measured electrical characteristics of a typical CMOS inverter (left) and individual p-(middle) and n-channel (right) metal-oxide-semiconductor field-effect transistors (MOSFETs). The gain and threshold voltage ($V_{th}$) are ~80 and −1 V, respectively. The negative threshold voltage of the inverters likely arises from the high negative threshold voltage (~−5 V) of the p-type MOSFETs. The mobilities, calculated from the saturation and linear regime, are ~60 $cm^2/V \cdot s$ and ~70 $cm^2/V \cdot s$ for the p-channel devices, and ~350 $cm^2/V \cdot s$ and ~400 $cm^2/V \cdot s$ for the n-channel devices, respectively. The on/off current ratios ($I_{on}/I_{off}$) are ~$10^5$ for both types of transistors.

FIG. 32 provides a set of images collected during dissolution of a system on rice paper (FIG. 21d), at various times after immersion in deionized (DI) water at 37° C. Here, rice paper rapidly absorbs water and begins to swell, thereby leading to disintegration of the array into individual devices. Each component then gradually disappears in a manner defined by the dissolution rates of various constituent materials.[13] Hydrolysis consumes the Mg electrodes in several hours. Dissolution of PECVD SiO$_2$ and Si in phosphate buffer solutions (PBS, pH 7.4) at physiological temperature occurs on a timescale of weeks. In all cases, the rates for complete disappearance depend strongly on temperature, pH, ionic content, thickness and morphology.

Potential applications of transient/bioresorbable electronics range from anti-tamper systems, green/eco-friendly electronics to implantable devices. FIG. 22 shows representative substrates that have generic relevance to these and other classes of applications: security systems (FIG. 22a), environmental sensors (FIGS. 22b and 22c) and green/compostable electronics (FIG. 22d).

To illustrate a specific example in biomedicine, consider a transient hydration sensor that might be used as an applique to monitor healing processes at the site of a wound on the skin, constructed on a PLGA substrate. FIG. 33a shows an image of a device, with a magnified view in the inset (left), and exploded-view schematic illustration (right). This system consists of eight separate channels with four measuring electrodes and four reference electrodes. The electrode geometries include circular and interdigitated designs. The device uses phosphorous doped silicon ($\sim 10^{20}$ cm$^{-3}$) for the electrodes ($\sim$300 nm), magnesium (Mg) for contacts/interconnects (200~250 nm), PECVD silicon dioxide (SiO$_2$) for the interlayer dielectrics ($\sim$100 nm) and PLGA for the substrate ($\sim$20 μm). A demonstration of operation involves applying lotion to the skin and then measuring frequency-dependent changes in the impedance as a function of time. The amplitude of the impedance measured at each channel changes monotonically with the level of skin hydration. After subtracting impedances associated with the measuring electrodes from the reference electrodes, the frequency-response of the device at different hydration levels can be obtained from circular (left) and interdigitated (right) electrode formats, as shown in FIG. 33b. As the hydration level changes from 119 to 16.7 (arbitrary units, determined by a commercial hydration meter (CMM)), the differential impedance amplitude at 15 kHz decreases steadily from $\sim$0.79 MΩ and $\sim$1.2 MΩ for circular and interdigitated electrodes, respectively. At a fixed hydration level of 16.7 , the differential impedance amplitude decreases from 0.866 MΩ at 15 kHz to 25 kΩ at 95 kHz for circular electrodes. These behaviors are similar to those observed previously in conformal, non-transient 'epidermal' sensors.[17] The changes are related to variations in the conductivity and permittivity of the skin, due likely to variations in the water and ionic content of the skin.[18-21] Experimental results in FIG. 33b can be converted into hydration levels using reference values from the CMM through least square fitting (FIG. 33c). The converted data are consistent with the CMM and with the transient hydration sensor in both electrode formats. Over a measurement period of approximately 12 minutes, deviations between the hydration levels from the CMM and calibrated values from the transient sensor are less than 14% and 7%, respectively.

FIG. 33d provides dissolution behaviors of a transient hydration sensor on PLGA substrate, at various times while submerged in phosphate buffer solution (PBS, 1M, pH 7.4 , Sigma-Aldrich, USA) at physiological temperature (37° C.). Upon immersion, the exposed magnesium (2$^{nd}$ Mg) disappears quickly, while the underlying Mg (1$^{st}$ Mg) slowly dissolves due to its encapsulation with PECVD SiO$_2$. Here, Si and PECVD SiO$_2$ will completely dissolve in days or weeks[13]; the PLGA will dissolve over some months.[1,3]

During dissolution, substrate materials such as PLGA can swell; this swelling can lead to fracture/disintegration of the supported device structures. These phenomena are important because they can disrupt device behavior, prior to dissolution of the constituent materials. Mechanics analysis can provide insights. Consider, for example, various thin film structures relevant to transient electronics (FIG. 33a): PLGA/Si/Mg/SiO$_2$/Mg, PLGA/Si/Mg/SiO$_2$, PLGA/Mg/SiO$_2$/Mg, PLGA/Mg/SiO$_2$. As a point of reference, consider also bare PLGA. Due to the high stiffness of the device layers, the system bends upward upon a swelling strain of $\epsilon_{swelling}$ in the PLGA. The bending curvature κ is related to the bending stiffness $\overline{EI}_i$ of each layered structure as $$\kappa = \frac{E'_{sub}\varepsilon_{swelling}}{\sum_{i=1}^{5}\alpha_i\overline{EI}_i}\left(\sum_{i=1}^{5}\alpha_i b_i - \frac{h_{sub}}{2}\right)h_{sub}, \quad (6)$$

where $E'_{sub}$ and $h_{sub}$ are the biaxial modulus and thickness of the PLGA substrate, $\alpha_i$ is the area percentage of each layered structure out of the total area and $b_i$ is the distance from the neutral mechanical plane (NMP) of each layered structure to the bottom surface of the PLGA. The bending induces a compressive strain above the NMP, thereby reducing the tensile strain $\epsilon_{swelling}$ from swelling to yield a strain, given by $$\varepsilon_i = \frac{E'_{sub}h_{sub}}{\overline{EA}_i}\varepsilon_{swelling} - \kappa(z - b_i), \quad (7)$$

where z is the distance measured from the bottom surface of the PLGA substrate, and $\overline{EA}_i$ is the tensile stiffness of each layered structure. For a swelling of 18% in the PLGA, the maximum strain calculated from Equation 7 is 4.90% in Si and 7.61% in SiO$_2$, which exceed the fracture strains of Si and SiO$_2$ ($\sim$1%). Fracture would therefore be expected to occur in this system. Calculations suggest that, to avoid fracture, relatively thick active layers (Si of 500 nm/Mg of 500 nm/SiO$_2$ of 400 nm/Mg of 100 nm) and thin substrates (10 μm), with swelling less than 7%, are required. Alternatively, the concepts of stretchable electronics could be exploited through appropriate structuring of the materials to allow in and out of plane mechanical buckling of the active materials, in response to swelling of the substrate. The relevant functional time period of the system could be simply defined by swelling, and associated fracture, rather than dissolution. Swelling of PLGA, for example, occurs slowly during the first few days of immersion in aqueous solution, and this rate can be adjusted by molecular weights and/or ratios of PLA to PGA.[22,23]

The concepts introduced here provide materials, manufacturing strategy and device designs for transient electronic circuits that can be integrated onto bioresorbable polymer substrates. The combined use of transient devices, comprised of inorganic materials with biopolymer substrates, provides some versatility in engineering desired behaviors. Additional considerations in mechanics and fracture can be important in determining the operating lifetimes and the system geometries.

Experimental Section

Fabrication of transient silicon complementary metal-oxide-semiconductor (CMOS) inverters: Three different doping procedures were performed on n-type silicon on insulator (SOI, top silicon ~260 nm, SOITEC, France) wafers. Boron doping at 550° C. using spin-on dopant (SOD, Filmtronics, USA) defined lightly doped regions for the p-wells (p⁻). Heavily doped p-type regions for source and drain electrodes were formed at 1050° C. for p-type transistors. Phosphorous doping at 950° C. defined highly doped areas for source and drain contacts for n-type transistors. Removal of the buried oxide by wet etching with HF released the top device silicon from the SOI, and enabled transfer printing onto a spin cast film of PMMA/D-PI on silicon carrier substrate. Doped silicon nanomembranes (Si NMs) were isolated by reactive ion etching (RIE; Plasmatherm) with sulfur hexafluoride ($SF_6$) gas. A thin layer of $SiO_2$ (~50 nm) formed by plasma-enhanced chemical vapor deposition (PE-CVD) served as the gate dielectric. Etching openings in this layer using a buffered oxide etchant (BOE, Transene Company Inc., USA) defined contact pads for source and drain electrodes. A 300 nm layer of Mg (deposited by electron beam evaporation) was used for source, drain, gate electrodes, as well as interconnects. Another thin layer of D-PI was cast on top of the Mg. Patterned etching removed certain regions of the polymer layers (D-PI, PMMA) and $SiO_2$, to create an open mesh structure that facilitated dissolution of the underlying sacrificial layer of PMMA. This process involved immersion in acetone to release an ultrathin circuit from the carrier substrate, suitable for retrieval onto the surface of a slab of PDMS. The bottom layer of D-PI was removed by reactive ion etching (RIE) using oxygen ($O_2$) gas, and the circuit was transfer printed onto a biodegradable polymer. Finally, the top layer of D-PI was removed by RIE.

Fabrication method for a transient hydration sensor: To form eight separate electrodes, doped monocrystalline silicon nanomembranes (thickness ~300 nm, p-type) were constructed on SOI wafers, using phosphorous spin-on dopant at 950° C. Approaches similar to those described in the previous section were used for device fabrication. The measuring and reference electrodes were defined by RIE. Layers of Mg and $SiO_2$ served as contacts/interconnects and interlayer dielectrics, respectively.

Electrical characterizations of a transient hydration sensor: A data acquisition system (DAQ) equipped with an impedance analyzer chip (AD5933, Analog Devices) and a multiplexer (ADG 708, Analog Devices) for switching between electrodes allowed measurements using the hydration sensor. Details appear elsewhere.[17] Briefly, an alternating current (AC) voltage (2V peak to peak) at frequencies between 15 kHz and 95 kHz was generated from the impedance analyzer and introduced to each of the electrodes of the hydration sensor through the multiplexer. The amplitude and phase of the reflected voltage from the skin was received by the common ground of the hydration sensor, and converted to impedance levels within the impedance analyzer. The hydration sensor was connected to the DAQ with anisotropic conductive film (ACF) cables. During in-vivo experiments, the sensor was attached to the skin of ventral forearm to reveal frequency dependent changes in impedance associated with application of moisturizing lotions (Intensive Rescue Moisture Body Lotion, Vaseline Inc.). A commercial moisture meter (CMM) (MoistureMeter SC Compact, Delfin Inc)[17] served as a reference to enable conversion of impedance values to hydration levels.

Supporting Information

For a design layout shown in FIG. 33a, there are four different layered structures, namely Si (300 nm)/Mg (200 nm)/$SiO_2$ (100 nm)/Mg (250 nm), Si (300 nm)/Mg (200 nm)/$SiO_2$ (100 nm), Mg (200 nm)/$SiO_2$ (100 nm)/Mg (250 nm) and Mg (200 nm)/$SiO_2$ (100 nm). As a composite, the bending stiffness of each layered structure in the device film can be calculated from $$\overline{EI}_{comp} = \sum_{i=1}^{N} E'_i h_i \left[ \left( b_{comp} - \sum_{j=1}^{i} h_j \right)^2 + \left( b_{comp} - \sum_{j=1}^{i} h_j \right) h_i + \frac{1}{3} h_i^2 \right], \quad (8)$$

where $b_{comp}$ is the distance from the neutral mechanical plane of the composite to the top surface of the PLGA substrate, and it is given as $$b_{comp} = \sum_{i=1}^{N} E'_i h_i \left( \sum_{j=1}^{i} h_j - \frac{h_i}{2} \right) \bigg/ \sum_{i=1}^{N} E'_i h_i, \quad (9)$$

with N is the number of layers, $E'_i$ and $h_i$ are the biaxial Young's modulus and thickness for each layer. For the Si/Mg/$SiO_2$/Mg structure, these parameters are given as N=4, $E'_1$=178.1 GPa, $h_1$=3200 nm for Si, $E'_2$=$E'_4$=69.23 GPa, $h_2$=200 nm, $h_4$=250 nm for Mg, and $E'_3$=113.3 GPa, $h_3$=100 nm for $SiO_2$. The effective bending stiffness $\overline{EI}_{eff}$ of the device film is averaged over four layered structures across the entire area. The tensile stiffness $\overline{EA}_{comp}$ of each layered structure is defined as $$\overline{EA}_{comp} = \sum_{i=1}^{N} E'_i h_i$$

and the effective tensile stiffness $\overline{EA}_{eff}$ is also averaged over the entire area. With the effective bending stiffness and tensile stiffness, the effective Young's modulus and thickness of the device film are obtained as $$E_{eff} = \sqrt{\overline{EA}^3_{comp} / 12 \overline{EI}_{comp}} \text{ and } h_{eff} = \sqrt{12 \overline{EI}_{comp} \sqrt{\overline{EA}_{comp}}}.$$

Subject to a swelling strain of $\epsilon_{swelling}$, the PLGA substrate together with the device film is bent upward and the curvature K is related bending stiffness EI of the system as $$\kappa = \frac{\overline{EA}_{comp} \varepsilon_{swelling}}{\overline{EI}} \left( h_{sub} - b + \frac{h_{eff}}{2} \right), \quad (10)$$

where $h_{sub}$=15 μm is the thickness of the PLGA substrate, $\overline{EI}$ can be calculated from Equation 8 with N=2, $E'_1$=$E_{sub}$, $h_1$=$h_{sub}$, $E'_2$=$E_{eff}$, $h_2$=$h_{eff}$, and b is the distance from the neutral mechanical plane (NMP) of the device/substrate system to the bottom surface of the PLGA substrate and can be calculated from Equation 9.

The strain in the device film can be calculated from a superposition of a swelling force in the device film and a compressive force in the opposite direction. The swelling force matches the device film to an isolated swelling substrate, while the compressive force introduces a compression and a bending moment at NMP in the film/substrate system. The strain at the mid surface of the effective device film consists of three components, namely the swelling strain, compressive strains from compressive force and bending moment. This leads to Equation 7 in the main text.

Table of References for Example 5

[1] X. S. Wu, N. Wang, *J. Biomater. Sci. Polymer Edn.* 2001, 12, 21.
[2] T. Ponnusamy, L. B. Lawson, L. C. Freytag, D. A. Blake, R. S. Ayyala, V. T. John, *Biomatter*, 2012, 2, 77.
[3] H. K. Makadia, S. J. Siegel, *Polymers*, 2011, 3, 1377.
[4] M. I. Sabir, X. Xu, L. Li, *J. Mater. Sci.* 2009, 44, 5713.
[5] C. X. F. Lam, M. M. Savalani, S. -H. Teoh, D. W. Hutmacher, *Biomed. Mater.* 2008, 3, 034108.
[6] M. A. Woodruff, D. W. Hutmacher, *Prog. Polym. Sci.* 2010, 35, 1217.
[7] D. W. Hutmacher, *J. Biomater. Sci. Polymer Edn.* 2001, 12, 107.
[8] D. -H. Kim, Y. -S. Kim, J. Amsden, B. Panilaitis, D. L. Kaplan, F. G. Omenetto, M. R. Zakin, J. A. Rogers, *Appl. Phys. Lett.* 2009, 95, 133701.
[9] D. -H. Kim, J. Viventi, J. Amsden, J. Xiao, L. Vigeland, Y. -S. Kim, J. A. Blanco, B. Panilaitis, E. S. Frechette, D. Contreras, D. L. Kaplan, F. G. Omenetto, Y. Huang, K.-C. Hwang, M. R. Zakin, B. Litt, J. A. Rogers, *Nat. Mater.* 2010, 9, 511.
[10] C. J. Bettinger, Z. Bao, *Adv. Mater.* 2010, 22, 651.
[11] M. Irimia-Vladu, P. A. Troshin, M. Reisinger, L. Shmygleva, Y. Kanbur, G. Schwabegger, M. Bodea, R. Schwödiauer, A. Mumyatov, J. W. Fergus, V. F. Razumov, Helmut Sitter, N. S. Sariciftci, S. Bauer, *Adv. Funct. Mater.* 2010, 20, 4069.
[12] C. Legnani, C. Vilani, V. L. Calil, H. S. Barud, W. G. Quirino, C. A. Achele, S. J. L. Ribeiro, M. Cremona, *Thin Solid Films*, 2008, 517, 1016.
[13] S. -W. Hwang, H. Tao, D. -H. Kim, H. Cheng, J. -K. Song, E. Rill, M. A. Brenckle, B. Panilaitis, S. M. Won, Y. S. -Kim. Y. M. Song, K. J. Yu, A. Ameen, R. Li, Y. Su, M. Yang, D. L. Kaplan, M. R. Zakin, M. J. Slepian, Y. Huang, F. G. Omenetto, J. A. Rogers, *Science*, 2012, 337, 1640.
[14] S. -W. Hwang, X. Huang, J. -H. Seo, J. -K. Song, S. Kim, S. Hage-Ali, H. -J. Chung, H. Tao, F. G. Omenetto, Z. Ma and J. A. Rogers, *Adv. Mater.* 2013, 25, 3526.
[15] S. -W. Hwang, D. -H. Kim, H. Tao, T. -I. Kim, S. Kim, K. J. Yu, B. Panilaitis, J. -W. Jeong, J. -K. Song, F. G. Omenetto and J. A. Rogers, *Adv. Funct. Mater.* 2013, 23, 4087.
[16] C. Dagdeviren, S. -W. Hwang, Y. Su, S. Kim, H. Cheng, O. Gur, R. Haney, F. G. Omenetto, Y. Huang, J. A. Rogers, *Small*, 2013, 9, 3398.
[17] X. Huang, W. -H. Yeo, Y. Liu, J. A. Rogers, *Biointerphases*, 2012, 7, 52.
[18] C. Gabriel, S. Gabriel and E. Corthout, *Phys. Med. Biol.* 2006, 41, 2231.
[19] C. Gabriel, A. Peyman, E. H. Grant, *Phys. Med. Biol.* 2009, 54, 4863.
[20] T. Sunaga, H. Ikehira, S. Furukawa, H. Shinkai, H. Kobayashi, Y. Matsumoto, E. Yoshitome, T. Obata, S. Tanada, H. Murata, Y. Sasaki, *Phys. Med. Biol.* 2002, 47, N11.
[21] V. Raicu, N. Kitagawa, A. Irimajiri, *Phys. Med. Biol.* 2000, 45, L1.
[22] L. K. Chiu, W. J. Chiu, Y. -L. Cheng, *Int. J. Pharm.* 1995, 126, 169.
[23] L. Solorio, A. M. Olear, J. I. Hamilton, R. B. Patel, A. C. Beiswenger, J. E. Wallace, H. Zhou, A. A. Exner, *Theranostics*, 2012, 2, 1064.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The following references relate generally to contact printing and printable components, such as semiconductor components, and each is hereby incorporated by reference in its entirety: U.S. Pat. Nos. 7,622,367, 7,557,367, 7,799,699, 7,943,491, 7,982,296, 8,039,847 and 7,521,292.

The following references relate generally to flexible and/or stretchable semiconductor materials and devices and each is hereby incorporated by reference in its entirety: U.S. patent application Ser. No. 12/778,588, filed on May 12, 2010, PCT International Application No. PCT/US05/19354, filed Jun. 2, 2005 and published under No. WO2005/122285 on Dec. 22, 2005, U.S. Provisional Patent Application No. 61/313,397, filed Mar. 12, 2010, U.S. patent application Ser. No. 11/851,182, filed Sep. 6, 2007 and published under No. 2008/0157235 on Jul. 3, 2008, and PCT International Application No. PCT/US07/77759, filed Sep. 6, 2007 and published under No. WO2008/030960 on Mar. 13, 2008.

The following references relate generally to bioresorbable substrates and methods of making bioresorbable substrates and each is hereby incorporated by reference in its entirety: PCT Patent Application PCT/US03/19968 filed Jun. 24, 2003, PCT Patent Application PCT/US04/000255 filed Jan. 7, 2004, PCT Patent Application PCT/US04/11199 filed Apr. 12, 2004, PCT Patent Application PCT/US05/20844 filed Jun. 13, 2005, and PCT Patent Application PCT/US06/029826 filed Jul. 28, 2006.

The following references relate generally to transient electronic devices, and each is hereby incorporated by reference in its entirety: U.S. patent application Ser. No. 13/624,096 filed Sep. 21, 2012 and PCT International Application No. PCT/US2012/056538 filed Sep. 21, 2012.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100 . It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

The following references relate generally to fabrication methods, structures and systems for making electronic devices, and are hereby incorporated by reference to the extent not inconsistent with the disclosure in this application:

| application Ser. No. | Filing Date | Publication No. | Publication Date | U.S. Pat. No. | Issue Date |
| --- | --- | --- | --- | --- | --- |
| 11/001,689 | Dec. 1, 2004 | 2006/0286488 | Dec. 21, 2006 | 7,704,684 | Apr. 27, 2010 |
| 11/115,954 | Apr. 27, 2005 | 2005/0238967 | Oct. 27, 2005 | 7,195,733 | Mar. 27, 2007 |

-continued

| application Ser. No. | Filing Date | Publication No. | Publication Date | U.S. Pat. No. | Issue Date |
|---|---|---|---|---|---|
| 11/145,574 | Jun. 2, 2005 | 2009/0294803 | Dec. 3, 2009 | 7,622,367 | Nov. 24, 2009 |
| 11/145,542 | Jun. 2, 2005 | 2006/0038182 | Feb. 23, 2006 | 7,557,367 | Jul. 7, 2009 |
| 11/421,654 | Jun. 1, 2006 | 2007/0032089 | Feb. 8, 2007 | 7,799,699 | Sep. 21, 2010 |
| 11/423,287 | Jun. 9, 2006 | 2006/0286785 | Dec. 21, 2006 | 7,521,292 | Apr. 21, 2009 |
| 11/423,192 | Jun. 9, 2006 | 2009/0199960 | Aug. 13, 2009 | 7,943,491 | May 17, 2011 |
| 11/465,317 | Aug. 17, 2006 | — | — | — | — |
| 11/675,659 | Feb. 16, 2007 | 2008/0055581 | Mar. 6, 2008 | — | — |
| 11/782,799 | Jul. 25, 2007 | 2008/0212102 | Sep. 4, 2008 | 7,705,280 | Apr. 27, 2010 |
| 11/851,182 | Sep. 6, 2007 | 2008/0157235 | Jul. 3, 2008 | 8,217,381 | Jul. 10, 2012 |
| 11/585,788 | Sep. 20, 2007 | 2008/0108171 | May 8, 2008 | 7,932,123 | Apr. 26, 2011 |
| 11/981,380 | Oct. 31, 2007 | 2010/0283069 | Nov. 11, 2010 | 7,972,875 | Jul. 5, 2011 |
| 12/372,605 | Feb. 17, 2009 | — | — | — | — |
| 12/398,811 | Mar. 5, 2009 | 2010/0002402 | Jan. 7, 2010 | 8,552,299 | Oct. 8, 2013 |
| 12/405,475 | Mar. 17, 2009 | 2010/0059863 | Mar. 11, 2010 | 8,198,621 | Jun. 12, 2012 |
| 12/418,071 | Apr. 3, 2009 | 2010/0052112 | Mar. 4, 2010 | 8,470,701 | Jun. 25, 2013 |
| 12/564,566 | Sep. 22, 2009 | 2010/0072577 | Mar. 25, 2010 | 7,982,296 | Jul. 19, 2011 |
| 12/669,287 | Jan. 15, 2010 | 2011/0187798 | Aug. 4, 2011 | — | — |
| 12/778,588 | May 12, 2010 | 2010/0317132 | Dec. 16, 2010 | — | — |
| 12/844,492 | Jul. 27, 2010 | 2010/0289124 | Nov. 18, 2010 | 8,039,847 | Oct. 18, 2011 |
| 12/892,001 | Sep. 28, 2010 | 2011/0230747 | Sep. 22, 2011 | 8,666,471 | Mar. 4, 2014 |
| 14/140,299 | Dec. 24, 2013 | — | — | — | — |
| 12/916,934 | Nov. 1, 2010 | 2012/0105528 | May 3, 2012 | 8,562,095 | Oct. 22, 2013 |
| 12/947,120 | Nov. 16, 2010 | 2011/0170225 | Jul. 14, 2011 | — | — |
| 12/996,924 | Dec. 8, 2010 | 2011/0147715 | Jun. 23, 2011 | — | — |
| 12/968,637 | Dec. 15, 2010 | 2012/0157804 | Jun. 21, 2012 | — | — |
| 13/046,191 | Mar. 11, 2011 | 2012/0165759 | Jun. 28, 2012 | — | — |
| 13/071,027 | Mar. 24, 2011 | 2011/0171813 | Jul. 14, 2011 | — | — |
| 13/095,502 | Apr. 27, 2011 | — | — | — | — |
| 13/100,774 | May 4, 2011 | 2011/0266561 | Nov. 3, 2011 | — | — |
| 13/113,504 | May 23, 2011 | 2011/0220890 | Sep. 15, 2011 | 8,440,546 | May 14, 2013 |
| 13/120,486 | Aug. 4, 2011 | 2011/0277813 | Nov. 17, 2011 | — | — |
| 13/228,041 | Sep. 8, 2011 | 2011/0316120 | Dec. 29, 2011 | — | — |
| 13/270,954 | Oct. 11, 2011 | 2012/0083099 | Apr. 5, 2012 | 8,394,706 | Mar. 12, 2013 |
| 13/349,336 | Jan. 12, 2012 | 2012/0261551 | Oct. 18, 2012 | — | — |
| 13/441,618 | Apr. 6, 2012 | 2013/0100618 | Apr. 25, 2013 | — | — |
| 13/441,598 | Apr. 6, 2012 | 2012/0327608 | Dec. 27, 2012 | — | — |
| 13/472,165 | May 15, 2012 | 2012/0320581 | Dec. 20, 2012 | — | — |
| 13/486,726 | Jun. 1, 2012 | 2013/0072775 | Mar. 21, 2013 | — | — |
| 13/492,636 | Jun. 8, 2012 | 2013/0041235 | Feb. 14, 2013 | — | — |
| 13/549,291 | Jul. 13, 2012 | 2013/0036928 | Feb. 14, 2013 | — | — |
| 13/596,343 | Aug. 28, 2012 | 2012/0321785 | Dec. 20, 2012 | 8,367,035 | Feb. 5, 2013 |
| 13/624,096 | Sep. 21, 2012 | 2013/0140649 | Jun. 6, 2013 | — | — |
| 13/801,868 | Mar. 13, 2013 | 2013/0320503 | Dec. 5, 2013 | — | — |
| 14/155,010 | Jan. 14, 2014 | — | — | — | — |
| 13/835,284 | Mar. 15, 2013 | — | — | — | — |
| 13/853,770 | Mar. 29, 2013 | — | — | — | — |

Every formulation or combination of components described or exemplified herein can be used to practice the invention, unless otherwise stated.

All patents and publications mentioned in the specification are indicative of the level of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

We claim:

1. A method of making a transient electronic device comprising the steps of:
fabricating one or more inorganic semiconductor components, one or more metallic conductor components or one or more inorganic semiconductor components and one or more metallic conductor components on a silicon-on-insulator (SOI) wafer; wherein the one or more inorganic semiconductor components or one or more metallic conductor components independently comprise a selectively transformable material and have a preselected transience profile;
providing a handle substrate having a receiving surface; wherein the receiving surface supports a release layer;
transfer printing the one or more inorganic semiconductor components, one or more metallic conductor components or one or more inorganic semiconductor components and one or more metallic conductor components from at least a portion of the SOI wafer to the release layer supported by the handle substrate;
removing the release layer on said handle substrate;
providing a substrate layer on top of the one or more inorganic semiconductor components, one or more metallic conductor components or one or more inorganic semiconductor components and one or more metallic conductor components;
releasing the substrate layer and the one or more inorganic semiconductor components, one or more metallic conductor components or one or more inorganic semiconductor components and one or more metallic conductor components from the handle substrate;

flipping the substrate layer and the one or more inorganic semiconductor components, one or more metallic conductor components or one or more inorganic semiconductor components and one or more metallic conductor components to access an exposed surface of said one or more inorganic semiconductor components, one or more metallic conductor components or one or more inorganic semiconductor components and one or more metallic conductor components supported by the substrate layer; and processing the exposed surface, thereby making said transient electronic device;

wherein the SOI wafer comprises: a silicon handle wafer having a <111> orientation; a buried insulator layer; and a top layer of active Si having a <100> orientation from which the one or more semiconductor components are formed.

2. The method of claim 1, wherein said step of fabricating one or more inorganic semiconductor components, one or more metallic conductor components or one or more inorganic semiconductor components and one or more metallic conductor components supported by an SOI wafer is carried out at a semiconductor foundry.

3. The method of claim 1, wherein said steps other than said step of fabricating one or more inorganic semiconductor components, one or more metallic conductor components or one or more inorganic semiconductor components and one or more metallic conductor components supported by an SOI wafer are not carried out in a semiconductor foundry.

4. The method of claim 1, wherein the processing step comprises adding a transient device component.

5. The method of claim 4, wherein the transient device component comprises an electrode, an electrical interconnect, a semiconductor, an encapsulating layer, or any combination thereof.

6. The method of claim 1, wherein the processing step further comprises modifying a physical parameter of the inorganic semiconductor component or metallic conductor component to make a corresponding transient inorganic semiconductor component or transient metal conductor component.

7. The method of claim 6, wherein the physical parameter is one or more of:
porosity, thickness, effective density, defect density, dopant concentration, composition, or morphology.

8. The method of claim 1, wherein the processing step comprises providing a transient substrate.

9. The method of claim 1, wherein the processing step comprises encapsulating at least a portion of the exposed surface with an encapsulating layer.

10. The method of claim 9, wherein the encapsulating layer comprises a selectively removable material that is at least partially removed in response to an external or internal stimulus.

11. The method of claim 10, wherein the selectively removable material of the encapsulating layer comprises a material selected from the group consisting of a polymer, a metal, a metal oxide, a glass and a ceramic.

12. The method of claim 9, wherein the encapsulating layer, the substrate and at least a portion of the one or more inorganic semiconductor components or the one or more metallic conductor components, each independently comprise a selectively transformable material.

13. The method of claim 1, wherein processing the exposed surface comprises providing one or more interconnect structures for electrically interconnecting the one or more semiconductor components, wherein the interconnect structures independently comprise a selectively transformable material and have a preselected transience profile.

14. The method of claim 1, further comprising the step of integrating a transient passive component, a transient active component, or both, with the one or more inorganic semiconductor components.

15. The method of claim 14, wherein the integrating step is carried out after the step of flipping the substrate layer.

16. The method of claim 14, wherein the integrating step is part of the fabricating step.

17. The method of claim 1 further comprising providing a protective layer between said release layer and said one or more inorganic semiconductor components, one or more metallic conductor components or one or more inorganic semiconductor components and one or more metallic conductor components.

18. The method of claim 17, wherein said protective layer allows for said removal of said release layer without substantial degradation of said one or more inorganic semiconductor components, one or more metallic conductor components or one or more inorganic semiconductor components and one or more metallic conductor components.

19. The method of claim 17 wherein said protective layer is a polymer layer in contact with said one or more inorganic semiconductor components, one or more metallic conductor components or one or more inorganic semiconductor components and one or more metallic conductor components.

20. The method of claim 1, wherein the fabricating step comprises forming a plurality of semiconductor components on the SOI wafer.

21. The method of claim 20, wherein the fabricating step further comprises undercutting the semiconductor components.

22. The method of claim 21, wherein the plurality of semiconductor components are freestanding on the SOI wafer and connected to the SOI wafer by one or more anchors.

23. The method of claim 1, further comprising the step of: etching the Si <111> handle wafer to facilitate release of the one or more semiconductor device components that comprise Si <100> from the SOI wafer.

24. The method of claim 1, wherein the SOI wafer comprises a commercial quality SOI wafer that is coated with the buried insulator layer that is an oxide layer, and the oxide layer is bonded to a bulk <111>-oriented silicon wafer.

25. The method of claim 24, wherein the oxide layer comprises silicon dioxide.

26. The method of claim 1, wherein the transfer printing comprises dry transfer contact printing.

27. The method of claim 26, wherein the dry transfer printing further comprises
contacting the one or more inorganic semiconductor components, one or more metallic conductor components or one or more inorganic semiconductor components and one or more metallic conductor components with a transfer device;
removing the transfer device and the one or more inorganic semiconductor components, one or more metallic conductor components or one or more inorganic semiconductor components and one or more metallic conductor components from the SOI wafer;
contacting the transfer device and the one or more inorganic semiconductor components, one or more metallic conductor components or one or more inorganic semiconductor components and one or more metallic conductor components to the handle substrate; and removing the transfer device without the one or more inorganic semiconductor components, one or more metallic conductor components or one or more inorganic semiconductor components and one or more metallic conductor components, thereby transferring the one or more inorganic semiconductor components, one or more metallic conductor components or one or more inorganic semiconductor components and one or more metallic conductor components to the handle substrate.

28. The method of claim 1, wherein the transfer printing is high throughput and high fidelity.

29. The method of claim 1, wherein the handle substrate comprises a Si wafer.

30. The method of claim 1, wherein the step of providing said substrate layer comprises:
spin casting; or
laminating a polymer, metal, metal oxide, ceramic or glass to a surface of the one or more metallic conductor components or one or more inorganic semiconductor components and one or more metallic conductor components.

31. The method of claim 30, wherein the polymer is an organic polymer, poly(lactic-co-glycolic acid) (PLGA), or polydimethylsiloxane (PDMS).

32. The method of claim 23, wherein providing the substrate layer is before the etching step.

33. The method of claim 23, wherein providing the substrate layer is after the etching step.

34. The method of claim 1, wherein the substrate layer comprises a selectively transformable material.

35. The method of claim 34, wherein the substrate layer has a user-selected degradation characteristic in a defined environmental setting.

36. The method of claim 35, wherein the degradation characteristic is a degradation rate that is at least partially dependent on a physical parameter of the surrounding environment.

37. The method of claim 1, wherein the step of releasing the substrate layer and the one or more inorganic semiconductor components, one or more metallic conductor components or one or more inorganic semiconductor components and one or more metallic conductor components from the handle substrate comprises applying a removal force to the substrate layer in a direction away from the handle substrate.

38. The method of claim 1, wherein the step of releasing the substrate layer and the one or more inorganic semiconductor components, one or more metallic conductor components or one or more inorganic semiconductor components and one or more metallic conductor components from the handle substrate comprises peeling the substrate layer in a direction away from the handle substrate.

39. The method of claim 1, wherein the substrate layer functions as a handle for separating the one or more inorganic semiconductor components, one or more metallic conductor components or one or more inorganic semiconductor components and one or more metallic conductor components from handle substrate.

40. The method of claim 39, wherein the substrate layer functions as a handle for transferring the one or more inorganic semiconductor components, one or more metallic conductor components or one or more inorganic semiconductor components and one or more metallic conductor components to a receiving substrate having a receiving surface.

41. The method of claim 1, wherein the release layer comprises a layer of poly(methylmethacrylate) (PMMA).

42. The method of claim 41, wherein the removing step comprises a two-step dry and wet process to facilitate removal of the substrate layer and the one or more inorganic semiconductor components, one or more metallic conductor components or one or more inorganic semiconductor components and one or more metallic conductor components from the handle wafer.

43. The method of claim 1, wherein the transience profile is selected by adjusting any one or more of:
a thickness of the semiconductor or the metallic conductor components;
a density of the semiconductor or the metallic conductor components;
a defect density of the semiconductor or the metallic conductor components;
a composition of the semiconductor or the metallic conductor components;
a porosity of the semiconductor or the metallic conductor components;
a crystallinity of the semiconductor or the metallic conductor components;
a dopant of the semiconductor or the metallic conductor components; or a morphology of the semiconductor or the metallic conductor components.

44. The method of claim 1, wherein the one or more metallic conductor components are independently selected from the group consisting of Mg, Mo, W, Fe, Zn and alloys thereof.

45. The method of claim 1 comprising fabricating a plurality of inorganic semiconductor components.

46. The method of claim 45, wherein the processing step comprises providing one or more metallic components.

47. The method of claim 46, wherein the one or more metallic components comprise interconnects that electrically interconnect one or more semiconductor components.

48. The method of claim 46, wherein the metallic components comprise electrodes in electrical communication with the one or more semiconductor components.

49. The method of claim 1, wherein the one or more inorganic semiconductor components or one or more metallic conductor components is microsized, having a lateral dimension that is greater than or equal to 5 μm and less than or equal to 500 μm.

50. The method of claim 1, wherein the transient electronic device comprises a metal-oxide semiconductor field-effect transistor (MOSFET); a complementary metal-oxide-semiconductor (CMOS), a transistor, a capacitive sensor, a diode, a photodector, or a capacitor.

51. The method of claim 1, wherein the transient electronic device is a communication system, a photonic device, a sensor, an optoelectronic device, a biomedical device, a temperature sensor, a photodetector, a photovoltaic device, a strain gauge, an imaging system, a wireless transmitter, an antenna, a battery, a nanoelectromechanical system or a microelectromechanical system.

52. The method of claim 1, comprising a plurality of semiconductor components or a plurality of metallic conductor components that are simultaneously transferred to the handle wafer, wherein the plurality is selected from a range that is greater than or equal to 2 components and less than or equal to 100,000,000 components.

53. The method of claim 1, wherein the one or more inorganic semiconductor components or the one or more metallic conductor components independently comprise one or more thin film structures.

54. The method of claim 53, wherein the one or more thin film structures each independently have a thickness selected over a range that is greater than or equal to 10 nm and less than or equal to 100 μm.

55. The method of claim 1, wherein the transient electronic device degrades in response to an environmental signal.

56. The method of claim 1, wherein the transient electronic device degrades in response to a user-initiated signal.

57. The method of claim 1, wherein the selectively transformable material has an electrical dissolution rate selected from the range of 0.01 nm/day to 100 μm/s.

58. The method of claim 1, wherein the preselected transience profile is characterized by one or more of:
- a transformation of 0.01% to 100% of said one or more inorganic semiconductor components or said one or more metallic conductor components over a time interval selected from the range of 1 ms to 5 years;
- a decrease in average thickness of said one or more inorganic semiconductor components or said one or more metallic conductor components at a rate selected over the range of 0.01 nm/day to 100 microns $s^{-1}$;
- a decrease in electrical conductivity of said one or more inorganic semiconductor components or said one or more metallic conductor components at a rate selected over the range of $10^{10}$ $S \cdot m^{-1}$ $s^{-1}$ to 1 $S \cdot m^{-1}$ $s^{-1}$;
- a change in morphology of said one or more inorganic semiconductor components or said one or more metallic conductor components, said change in morphology selected from the group consisting of pitting, flaking, cracking and uniform degradation;
- a percentage decrease in density of said one or more inorganic semiconductor components or said one or more metallic conductor components selected over the range of 0.01% to 99.9%; or
- a percentage increase in porosity of said one or more inorganic semiconductor components or said one or more metallic conductor components selected over the range of 0.01% to 99.9%.

* * * * *